(12) United States Patent
Heightman et al.

(10) Patent No.: US 11,786,600 B2
(45) Date of Patent: Oct. 17, 2023

(54) CLIPTAC COMPOSITION

(71) Applicant: OTSUKA PHARMACEUTICAL CO., LTD., Tokyo (JP)

(72) Inventors: Thomas Daniel Heightman, Harpenden (GB); Honorine Lebraud, Cambridge (GB)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 1349 days.

(21) Appl. No.: 16/308,140

(22) PCT Filed: Jun. 9, 2017

(86) PCT No.: PCT/IB2017/000701
§ 371 (c)(1),
(2) Date: Dec. 7, 2018

(87) PCT Pub. No.: WO2017/212329
PCT Pub. Date: Dec. 14, 2017

(65) Prior Publication Data
US 2019/0275161 A1     Sep. 12, 2019

(30) Foreign Application Priority Data
Jun. 10, 2016 (GB) .................... 1610156

(51) Int. Cl.
*A61K 47/54* (2017.01)
*A61K 47/68* (2017.01)

(52) U.S. Cl.
CPC ........ *A61K 47/555* (2017.08); *A61K 47/6871* (2017.08)

(58) Field of Classification Search
None
See application file for complete search history.

(56) References Cited

U.S. PATENT DOCUMENTS

2002/0068063 A1   6/2002   Deshaies et al.
2004/0038358 A1   2/2004   Dashaies et al.
(Continued)

FOREIGN PATENT DOCUMENTS

CN   105085620 A   11/2015
WO   00/47220 A1   8/2000
(Continued)

OTHER PUBLICATIONS

Bondeson et al., Nature Chemical Biology 2015, vol. 11, pp. 634-635 (Year: 2015).*
(Continued)

*Primary Examiner* — Karl J Puttlitz
(74) *Attorney, Agent, or Firm* — Heslin Rothenberg Farley & Mesiti P.C.

(57) ABSTRACT

The invention provides a CLIPTAC comprising: (a) a first portion comprising a ligand for an intracellular target protein; (b) a second portion comprising a ligand for an E3 ubiquitin ligase; and (c) a linker portion covalently coupling the first and second portions; wherein the linker comprises a covalent bond produced by a bioorthogonal click reaction between a compatible pair of reactive moieties. CLIPTAC precursor compositions and CLIPTAC precursors are also provided, together with pharmaceutical compositions comprising the CLIPTAC, CLIPTAC precursor compositions and CLIPTAC precursors, and methods of treatment using the same.

25 Claims, 8 Drawing Sheets

(56) References Cited

U.S. PATENT DOCUMENTS

Figure 1:
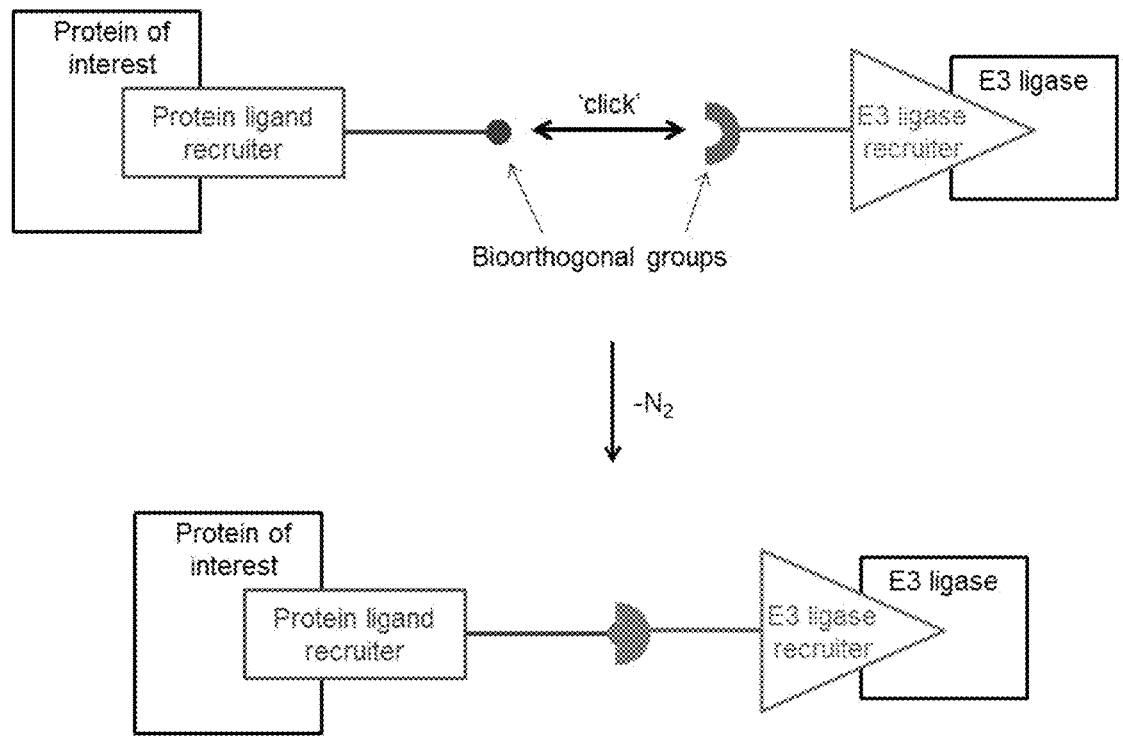

| | | |
|---|---|---|
| 2009/0068738 A1 | 3/2009 | Bertozzi et al. |
| 2015/0291562 A1 | 10/2015 | Crew et al. |
| 2016/0022642 A1 | 1/2016 | Crews et al. |
| 2016/0045607 A1 | 2/2016 | Crew et al. |
| 2016/0058872 A1 | 3/2016 | Crew et al. |

FOREIGN PATENT DOCUMENTS

| | | | |
|---|---|---|---|
| WO | 2010/051530 A2 | | 5/2010 |
| WO | 2012/003281 A2 | | 1/2012 |
| WO | 2012/078559 A2 | | 6/2012 |
| WO | 2012/106671 A1 | | 8/2012 |
| WO | 2012/135284 A2 | | 10/2012 |
| WO | 2013/009869 A2 | | 1/2013 |
| WO | 2013/106643 A2 | | 7/2013 |
| WO | 2013106643 | * | 7/2013 |
| WO | 2013/170147 A1 | | 11/2013 |
| WO | 2014/063061 A1 | | 4/2014 |
| WO | 2014/065860 A1 | | 5/2014 |
| WO | 2014/108452 A1 | | 7/2014 |
| WO | 2015/000867 A1 | | 1/2015 |
| WO | 2015/000868 A1 | | 1/2015 |
| WO | 2015/038933 A1 | | 3/2015 |
| WO | 2015/164604 A1 | | 10/2015 |
| WO | 2015/171543 A1 | | 11/2015 |

OTHER PUBLICATIONS

Lu et al., Chemistry and Biology 2015, vol. 22, No. 6, pp. 755-763 (Year: 2015).*
Winter et al., Science 2015, vol. 348, No. 6241, pp. 1376-1381 (Year: 2015).*
Lebraud et al., ACS Cent. Sci. 2016, 2, 927-934 (Year: 2016).*
Cook et al., Biochemical Society Transactions (2020) 48 1859-1875 (Year: 2020).*
Dekker et al., Drug Discovery Today, vol. 19, No. 5, May 2014 (Year: 2014).*
Morera et al. Clinical Epigenetics (2016) 8:57 (Year: 2016).*
Jambhekar et al., Cold Spring Harb Perspect Med 2017;7:a026484 (Year: 2017).*
James et al., Abstract, Nature Chemical Biology 9, 184-191 at (2013) downloaded from https://www.nature.com/articles/nchembio.1157 and https://www.thesgc.org/chemical-probes/UNC1215. (Year: 2013).*
Copeland, Phil. Trans. R. Soc. B 373: 20170080, 2018, http://dx.doi.org/10.1098/rstb.2017.0080 (Year: 2018).*
Chu et al. (2016) Specific Knockdown of Endogenous Tau Protein by Peptide-Directed Ubiquitin-Proteasome Degradation Cell Chemical Biology 23: 453-461 (Year: 2016).*
Chowdhury et al., Pharmaceut Fronts 2019;1:e22-e32 (Year: 2019).*
Akgun, B., et al., "Fast and Tight Boronate Formation for Click Bioorthogonal Conjugation", Angew. Chem. Int. Ed., vol. 55, No. 12, pp. 3909-3913 (2016).
Blackman, M.L., et al., "Tetrazine Ligation: Fast Bioconjugation Based on Inverse-Electron-Demand Diels-Alder Reactivity", J. Am. Chem. Soc., vol. 130, pp. 13518-13519 (2008).
Bondeson, D.P., et al., "Catalytic in vivo protein knockdown by small-molecule PROTACs", Nature Chemical Biology, Vo. 11, pp. 611-617 (2015).
Chu, T., et al., "Specific Knockdown of Endogenous Tau Protein by Peptide-Directed Ubiquitin-Proteasome Degradation", Chemical Cell Biology, vol. 23, pp. 453-461 (2016).
Cyrus, K., et al., "Impact of linker length on the activity of PROTACs", Molecular BioSystems, vol. 7, pp. 359-364 (2010).
Deshaies, R.J., et al., "Prime time for PROTACs", Nature Chemical Biology, vol. 11, pp. 634-635 (2015).
Devaraj, N.K., et al., "Tetrazine-Based Cycloadditions: Application of Pretargeted Live Cell Imaging", Bioconjugate Chem., vol. 19, pp. 2297-2299 (2008).
Galdeano, C., et al., "Structure-Guided Design and Optimization of Small Molecules Targeting the Protein-Protein Interaction between the von Hippel-Lindau (VHL) E3 Upiquitin Ligase and the Hypoxia Inducible Factor (HIF) Alpha Subunit with in the Vitro Nanomolar Affinities", Journal of Medicinal Chemistry, vol. 57, pp. 8657-8663 (2014).
Ito, T., et al., "Identification of a Primary Target of Thalidomide Teratogenicity", Science, Vo. 327, pp. 1345-1350 (2010).
Keinänen, O., et al., "A New Highly Reactive and Low Lipophilicity Fluorine-18 Labeled Tetrazine Derivative for Pretargeted PET Imaging", ACS Medicinal Chemistry Letters, vol. 7, pp. 62-66 (2016).
Köhn, M., et al., "The Staudinger Ligation—A Gift to Chemical Biology", Angew. Chem. Int. Ed., vol. 43, pp. 3106-3116 (2004).
Lebraud, H., et al., "Protein Degradation by In-Cell Self-Assembly of Proteolysis Targeting Chimeras", ACS Cent. Sci., vol. 2, No. 12, pp. 927-934 (2016).
Li, Z., et al., "Tetrazole Photoclick Chemistry: Reinvestigating Its Suitability as a Bioortogonal Reaction and Potential Applications", Angew. Chem. Int. Ed., vol. 55, No. 6, pp. 2002-2006 (2016).
Lu, J., et al., "Hijacking the E3 Ubiquitin Ligase Cereblon to Efficiently Target BRD4", Chemistry & Biology, vol. 22, No. 6, pp. 755-763 (2015).
McKay, C.S., et al., "Click Chemistry in Complex Mixtures: Bioorthogonal Bioconjugation", Chemistry & Biology, vol. 21, No. 9, pp. 1075-1101 (2014).
Patterson, D.M., et al, "Finding the Right (Bioorthogonal) Chemistry", ACS Chemical Biology, vol. 9, pp. 592-605 (2014).
Reiner, T., et al., "Bioorthogonal Small-Molecule Ligands for PARP1 Imaging in Living Cells", ChemBioChem, vol. 11, pp. 2374-2377 (2010).
Rostovtsev, V.V., et al., "A Stepwise Huisgen Cycloadditionl Process: Copper(I)-Catalyzed Regioselective "Ligation" of Azides and Terminal Alkynes", Angew. Chem. Int. Ed., vol. 41, No. 14, pp. 2596-2599 (2002).
Sakamoto, K.M., et al., "Protacs: Chimeric molecules that target proteins to the Skp1-Cullin-F box complex and for ubiquitination and degradation", PNAS, vol. 98, No. 15, pp. 8554-8559 (2001).
Saxon, E., et al., "Cell Surface Engineering by a Modified Staudinger Reaction", Science, vol. 287, pp. 2007-2010 (2000).
Selvaraj, R., et al., "trans-Cyclooctene—a stable, voracious dienophile for biorthogonal labeling", Current Opinion in Chemical Biology, vol. 17, pp. 753-760 (2013).
Sletten, E.M., et al., "Bioorthogonal Chemistry: Fishing for Selectivity in a Sea of Functionality", Angew. Chem. Int. Ed., vol. 48, pp. 6974-6998 (2009).
Tsai, Y., et al., "Selective, rapid and optically switchable regulation of protein function in live mammalian cells", Nature Chemistry, vol. 7, pp. 554-561 (2015).
Winter, G.E., "Phthalimide conjugation as a strategy for in vivo target protein degradation", Science, vol. 348, No. 6241, pp. 1376-1381 (2015).
Wu, H., et al., "In Situ Synthesis of Alkenyl Tetrazines for Highly Fluorogenic Bioorthogonal Live-Cell Imaging Probes", Angew. Chem. Int. Ed., vol. 126, pp. 5915-5919 (2014).
Yang, J., et al., "Metal-Catalyzed One-Pot Syntesis of Tetrazines Directly from Aliphatic Nitriles and Hydrazine", Angew. Chem. Int. Ed., vol. 51, pp. 5222-5225 (2012).
Yang, K.S., et al., "Bioorthogonal Imaging of Aurora Kinase A in Live Cells", Angew. Chem. Int. Ed., vol. 51, pp. 6598-6603 (2012).
Yang, J., et al., "Synthesis and Reactivity Comparisons of 1-Methyl-3-Substituted Cyclopropene Mini-tags for Tetrazine Bioorthogonal Reactions", Chem. Eur. J., vol. 20, pp. 3365-3375 (2014).
Zengerle, M., et al., "Selective Small Molecule Induced Degradation of the BET Bromodomain Protein BRD4", ACS Chemical Biology, vol. 10, pp. 1770-1777 (2015).
International Search Report and Written Opinion of the International Searching Authority for PCT/IB2017/000701 dated Oct. 18, 2017.
Search Report for Great Britain Application No. GB1610156.0 dated Mar. 27, 2017.

(56) References Cited

OTHER PUBLICATIONS

Lai, A.C., et al., "Modular PROTAC Design for the Degradation of Oncogenic BCR-ABL", Angew. Chem. Int. Ed., vol. 55, pp. 807-810 (2016).

* cited by examiner

CLIPTAC COMPOSITION

CROSS REFERENCE TO RELATED APPLICATIONS

This application is a national stage filing under section 371 of International Application No. PCT/IB2017/000701, filed on Jun. 9, 2017, and published on Dec. 14, 2017 as WO 2017/212329, which claims priority to Great Britain Application No. 1610156.0, filed on Jun. 10, 2016. The entire contents of WO 2017/212329 are hereby incorporated herein by reference.

TECHNICAL FIELD

This invention relates to proteolysis targeting chimeric molecules formed from the intracellular self-assembly of precursors via bioorthogonal click chemistry (CLIPTACs), as well as related precursor compositions, methods and therapeutic applications.

BACKGROUND OF THE INVENTION

PROteolysis Targeting Chimeras (PROTACs)

Selective degradation of intracellular proteins using proteolysis targeting chimeras (PROTACs) is emerging as a promising potential alternative to protein inhibition for therapeutic intervention (Sakamoto et al. (2001) Protacs: Chimeric molecules that target proteins to the Skp1-Cullin-F box complex for ubiquitination and degradation. *P. Natl. Acad. Sci.* 98: 8554-8559).

PROTACs offer important advantages over small molecule inhibition of therapeutic targets. While small molecule inhibitors act via target occupancy, PROTACs offer a long lasting effect by eliminating the target until re-synthesis, which can take hours or days. Moreover, by triggering the degradation of the protein target, all functional sites are removed, abolishing all target protein functions. Such 'knockdown' is not feasible with small molecule inhibitor drugs, which typically interact with only one site on the target, leaving the others to function normally. In addition, developing small molecule inhibitor drugs is challenging: many intracellular target proteins of great clinical importance are currently classed as "poorly druggable". PROTACs are expected to be particularly useful in such circumstances, since the target protein ligand does not need to be a functional inhibitor.

Current PROTAC molecules incorporate a ligand for the intracellular target protein and an E3 ubiquitin ligase recruiting group, joined by a linker of a length appropriate to bring together target protein and ubiquitinating machinery and thereby elicit the ubiquitination of the protein of interest and its subsequent degradation in the proteasome.

Various ligands for E3 ligases have been identified. Initial studies used natural peptide substrate sequences as ligands to recruit the Skp1-Cullin-F box complex or the von-Hippel-Lindau (VHL) E3 ubiquitin ligases. Such ligands impose obvious limitations on the cell permeability of the resulting bifunctional molecules and there is currently much interest in the design of more 'drug-like' PROTACs.

Non-peptidic VHL ligands have been identified which have improved physicochemical properties (Galdeano et al. (2014) Structure-Guided Design and Optimization of Small Molecules Targeting the Protein-Protein Interaction between the von Hippel-Lindau (VHL) E3 Ubiquitin Ligase and the Hypoxia Inducible Factor (HIF) Alpha Subunit with in Vitro Nanomolar Affinities. *J. Med. Chem.* 57: 8657-8663), while the phthalimide immunomodulatory drug thalidomide has been identified as a ligand of the E3 ubiquitin ligase cereblon (CRBN) (Ito et al. (2010) Identification of a Primary Target of Thalidomide Teratogenicity. *Science* 327: 1345-1350). These discoveries have enabled several groups to design PROTACs targeting the efficient degradation of various intracellular target proteins, including BRD4 (Winter et al. (2015) Phthalimide conjugation as a strategy for in vivo target protein degradation. *Science* 348: 1376-1381; Lu et al. (2015) Hijacking the E3 Ubiquitin Ligase Cereblon to Efficiently Target BRD4. *Chem. Biol.* 22: 755-763; Zengerle et al. (2015) Selective Small Molecule Induced Degradation of the BET Bromodomain Protein BRD4. *ACS Chem. Biol.* 10: 1770-1777), BCR-ABL (Lai et al. (2016) Modular PROTAC Design for the Degradation of Oncogenic BCR-ABL. *Angew. Chem. Int. Ed.* 55: 807-810), ERRα and RIPK2 (Bondeson et al. (2015) Catalytic in vivo protein knockdown by small-molecule PROTACs. *Nat. Chem. Biol.* 11: 611-617).

Of the reported PROTACs eliciting the degradation of BRD4, two (dBET1 and ARV-825) contain the BRD4 ligand JQ1 and the ligase recruiter thalidomide. These PROTACs differ only in the nature and length of their linker, which affects the efficiency of BRD4 degradation. The third, MZ1, uses VHL-1 as the ligase recruiter and JQ1 as the BRD4 ligand. Targeted BRD4 proteolytic knock-down has therefore emerged as a useful model system for PROTAC development and validation.

However, as heterobifunctional molecules, even the more recently described 'drug-like' PROTACs possess a relatively high molecular weight, which can limit cellular permeation and solubility, and compromise bioavailability and pharmacokinetics (Deshaies (2015) Protein degradation: Prime time for PROTACs. *Nat. Chem. Biol.* 11: 634-635).

Bioorthocional Click Chemistry

"Click chemistry" is a term introduced by Sharpless in 2002 to describe reactions that are high yielding, wide in scope, create only by-products that can be removed without chromatography, are stereospecific, simple to perform and can be conducted in easily removable or benign solvents (Rostovtsev et al. (2002) A Stepwise Huisgen Cycloaddition Process: Copper(I)-Catalyzed Regioselective "Ligation" of Azides and Terminal Alkynes. *Angew. Chem. Int. Ed.* 41: 2596-2599). It has since been implemented in many different forms, with wide applications in both chemistry and biology.

A subclass of click reactions involve reactants which are inert to the surrounding biological milieu. Such click reactions are termed bioorthogonal (Sletten et al. (2009) Bioorthogonal Chemistry: Fishing for Selectivity in a Sea of Functionality. *Angew. Chem. Int. Ed.* 48: 6974-6998). Bioorthogonal reactant pairs suitable for bioorthogonal click chemistry are molecular groups with the following properties: (1) they are mutually reactive but do not significantly cross-react or interact with cellular biochemical systems in the intracellular milieu; (2) they and their products and byproducts are stable and nontoxic in physiological settings; and (3) their reaction is highly specific and fast.

The present invention addresses the above-described limitations of PROTACs by providing them in the form of relatively low molecular weight precursors which can be individually delivered to a cell more effectively. Once in the cell, the precursors self-assemble by a bioorthogonal click reaction to form an active PROTAC. The invention therefore provides a novel class of PROTACs referenced herein as CLIckable Proteolysis TArgeting Chimeras (CLIPTACs).

SUMMARY OF THE INVENTION

According to a first aspect of the invention there is provided a CLIPTAC as defined in claim 1.

In a second aspect of the invention there is provided a self-assembling CLIPTAC precursor composition as defined in claim 30.

In a third aspect of the invention there is provided a CLIPTAC precursor as defined in claim 48 or claim 53.

Other aspects of the invention are defined in the claims set out below.

DETAILED DESCRIPTION OF THE INVENTION

All publications, patents, patent applications and other references mentioned herein are hereby incorporated by reference in their entireties for all purposes as if each individual publication, patent or patent application were specifically and individually indicated to be incorporated by reference and the content thereof recited in full.

Definitions

Where used herein and unless specifically indicated otherwise, the following terms are intended to have the following meanings in addition to any broader (or narrower) meanings the terms might enjoy in the art:

Unless otherwise required by context, the use herein of the singular is to be read to include the plural and vice versa. The term "a" or "an" used in relation to an entity is to be read to refer to one or more of that entity. As such, the terms "a" (or "an"), "one or more," and "at least one" are used interchangeably herein.

As used herein, the term "CLIPTAC" defines a proteolysis targeting chimeric molecule (PROTAC) formed from the intracellular self-assembly of precursors via bioorthogonal click chemistry (CLIckable Proteolysis TArgeting Chimera chimeric molecule).

As used herein, the term "comprise," or variations thereof such as "comprises" or "comprising," are to be read to indicate the inclusion of any recited integer (e.g. a feature, element, characteristic, property, method/process step or limitation) or group of integers (e.g. features, element, characteristics, properties, method/process steps or limitations) but not the exclusion of any other integer or group of integers. Thus, as used herein the term "comprising" is inclusive or open-ended and does not exclude additional, unrecited integers or method/process steps.

The phrase "consisting essentially of" is used herein to require the specified integer(s) or steps as well as those which do not materially affect the character or function of the claimed invention.

As used herein, the term "consisting" is used to indicate the presence of the recited integer (e.g. a feature, element, characteristic, property, method/process step or limitation) or group of integers (e.g. features, element, characteristics, properties, method/process steps or limitations) alone.

As used herein, the term "disease" is used to define any abnormal condition that impairs physiological function and is associated with specific symptoms. The term is used broadly to encompass any disorder, illness, abnormality, pathology, sickness, condition or syndrome in which physiological function is impaired irrespective of the nature of the aetiology (or indeed whether the aetiological basis for the disease is established). It therefore encompasses conditions arising from infection, trauma, injury, surgery, radiological ablation, poisoning or nutritional deficiencies.

As used herein, the term "treatment" or "treating" refers to an intervention (e.g. the administration of an agent to a subject) which cures, ameliorates or lessens the symptoms of a disease or removes (or lessens the impact of) its cause(s) (for example, pathological variegated states). In this case, the term is used synonymously with the term "therapy".

Additionally, the terms "treatment" or "treating" refers to an intervention (e.g. the administration of an agent to a subject) which prevents or delays the onset or progression of a disease or reduces (or eradicates) its incidence within a treated population. In this case, the term treatment is used synonymously with the term "prophylaxis".

The term "subject" (which is to be read to include "individual", "animal", "patient" or "mammal" where context permits) defines any subject, particularly a mammalian subject, for whom treatment is indicated. Mammalian subjects include, but are not limited to, humans, domestic animals, farm animals, zoo animals, sport animals and pet animals. In preferred embodiments, the subject is a human.

As used herein, an "effective amount" of a compound or composition defines an amount that can be administered to a subject without excessive toxicity, irritation, allergic response, or other problem or complication, commensurate with a reasonable benefit/risk ratio, but one that is sufficient to provide the desired effect, e.g. the treatment or prophylaxis manifested by a permanent or temporary improvement in the subject's condition. The amount will vary from subject to subject, depending on the age and general condition of the individual, mode of administration and other factors. Thus, while it is not possible to specify an exact effective amount, those skilled in the art will be able to determine an appropriate "effective" amount in any individual case using routine experimentation and background general knowledge. A therapeutic result in this context includes eradication or lessening of symptoms, reduced pain or discomfort, prolonged survival, improved mobility and other markers of clinical improvement. A therapeutic result need not be a complete cure.

As used herein, the term "antibody" defines whole antibodies (including polyclonal antibodies and monoclonal antibodies (mAbs)). The term is also used herein to refer to antibody fragments, including F(ab), F(ab'), F(ab')2, Fv, Fc3 and single chain antibodies (and combinations thereof), which may be produced by recombinant DNA techniques or by enzymatic or chemical cleavage of intact antibodies. The term "antibody" is also used herein to cover bispecific or bifunctional antibodies which are synthetic hybrid antibodies having two different heavy/light chain pairs and two different binding sites. Bispecific antibodies can be produced by a variety of methods including fusion of hybridomas or linking of Fab' fragments. Also covered by the term "antibody" are chimaeric antibodies (antibodies having a human constant antibody immunoglobulin domain coupled to one or more non-human variable antibody immunoglobulin domain, or fragments thereof). Such chimaeric antibodies therefore include "humanized" antibodies. Also covered by the term "antibody" are minibodies (see WO 94/09817), single chain Fv-Fc fusions and human antibodies produced by transgenic animals The term "antibody" also includes multimeric antibodies and higher-order complexes of proteins (e.g. heterodimeric antibodies).

As used herein, the term "peptide" defines organic compounds comprising two or more amino acids covalently joined by peptide bonds. The corresponding adjectival term "peptidic" is to be interpreted accordingly. Peptides may be referred to with respect to the number of constituent amino acids, i.e., a dipeptide contains two amino acid residues, a tripeptide contains three, etc. Peptides containing ten or fewer amino acids may be referred to as oligopeptides, while those with more than ten amino acid residues are polypeptides. Such peptides may also include any of the modifications and additional amino and carboxy groups.

As used herein, the term "proteostasis" is the regulation of the concentration, conformation (tertiary structure), binding interactions (quaternary structure) and location of the individual proteins that constitute the proteome of an organism. Proteostasis is therefore essential for maintaining normal cellular function and so ultimately determines the health status of the organism as a whole.

As used herein, the term "proteostatic disease" is used to define a set of diseases mediated, at least in part, by deficiencies in proteostasis. The term therefore covers aggregative and misfolding proteostatic diseases, including in particular neurodegenerative disorders (e.g. Parkinson's disease, Alzheimer's disease and Huntington's disease).

As used herein, the term "combination", as applied to two or more components, is intended to define material in which the two or more components are associated. The terms "combined" and "combining" in this context are to be interpreted accordingly.

The association of the two or more components in a combination may be physical or non-physical. Examples of physically associated combined components include:
 compositions (e.g. unitary formulations) comprising the two or more components in admixture (for example within the same unit dose);
 compositions comprising material in which the two or more component are chemically/physicochemically linked (for example by crosslinking, molecular agglomeration or binding to a common vehicle moiety);
 compositions comprising material in which the two or more component are chemically/physicochemically co-packaged (for example, disposed on or within lipid vesicles, particles (e.g. micro- or nanoparticles) or emulsion droplets);
 pharmaceutical kits, pharmaceutical packs or patient packs in which the two or more component are co-packaged or co-presented (e.g. as part of an array of unit doses);

Examples of non-physically associated combined components include:
 material (e.g. a non-unitary formulation) comprising at least one of the two or more components together with instructions for the extemporaneous association of at least one compound/agent to form a physical association of the two or more compounds/agents;
 material (e.g. a non-unitary formulation) comprising at least one of the two or more components together with instructions for combination therapy with the two or more components;
 material comprising at least one of the two or more components together with instructions for administration to a patient population in which the other(s) of the two or more components have been (or are being) administered;
 material comprising at least one of the two or more components in an amount or in a form which is specifically adapted for use in combination with the other(s) of the two or more components.

As used herein, the term "combination therapy" is intended to define therapies which comprise the use of a combination of two or more components (as defined above). Thus, references to "combination therapy", "combinations" and the use of components "in combination" in this application may refer to components that are administered as part of the same overall treatment regimen. As such, the posology of each of the two or more components may differ: each may be administered at the same time or at different times. It will therefore be appreciated that the components of the combination may be administered sequentially (e.g. before or after) or simultaneously, either in the same pharmaceutical formulation (i.e. together), or in different pharmaceutical formulations (i.e. separately). Simultaneously in the same formulation is as a unitary formulation whereas simultaneously in different pharmaceutical formulations is non-unitary. The posologies of each of the two or more components in a combination therapy may also differ with respect to the route of administration.

As used herein, the term "pharmaceutical kit" defines an array of one or more unit doses of a pharmaceutical composition together with dosing means (e.g. measuring device) and/or delivery means (e.g. inhaler or syringe), optionally all contained within common outer packaging. In pharmaceutical kits comprising a combination of two or more components, the individual components may be unitary or non-unitary formulations. The unit dose(s) may be contained within a blister pack. The pharmaceutical kit may optionally further comprise instructions for use.

As used herein, the term "pharmaceutical pack" defines an array of one or more unit doses of a pharmaceutical composition, optionally contained within common outer packaging. In pharmaceutical packs comprising a combination of two or more compounds/agents, the individual compounds/agents may be unitary or non-unitary formulations. The unit dose(s) may be contained within a blister pack. The pharmaceutical pack may optionally further comprise instructions for use.

As used herein, the term "patient pack" defines a package, prescribed to a patient, which contains pharmaceutical compositions for the whole course of treatment. Patient packs usually contain one or more blister pack(s). Patient packs have an advantage over traditional prescriptions, where a pharmacist divides a patient's supply of a pharmaceutical from a bulk supply, in that the patient always has access to the package insert contained in the patient pack, normally missing in patient prescriptions. The inclusion of a package insert has been shown to improve patient compliance with the physician's instructions.

The combinations of the invention may produce a therapeutically efficacious effect relative to the therapeutic effect of the individual compounds/agents when administered separately.

A "pharmaceutical composition" is a solid or liquid composition in a form, concentration and level of purity suitable for administration to a patient (e.g. a human or animal patient) upon which administration it can elicit the desired physiological changes. Pharmaceutical compositions are typically sterile and/or non-pyrogenic. The term non-pyrogenic as applied to the pharmaceutical compositions of the invention defines compositions which do not elicit undesirable inflammatory responses when administered to a patient. The pharmaceutical compositions of the invention preferably comprise a pharmaceutically acceptable carrier, pharmaceutically acceptable excipient, physiologically acceptable carrier or physiologically acceptable excipient.

As used herein, and unless otherwise specified, the term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid or solid filler, diluent, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, *Remington: The Science and Practice of Pharmacy,* 21st Edition, Lippincott Williams & Wilkins: Philadelphia, Pa., 2005; *Handbook of Pharmaceutical Excipients,* 5th Edition, Rowe et al., Eds., The Pharmaceutical Press and the American Pharmaceutical Association: 2005; *Handbook of Pharmaceutical Additives,* 3rd Edition, Ash and Ash Eds., Gower Publishing Company: 2007; and *Pharmaceutical Preformulation and Formulation,* 2nd Edition, Gibson Ed., CRC Press LLC: Boca Raton, Fla., 2009.

As used herein, and unless otherwise specified, the term "therapeutically effective amount" is meant to include the amount of a compound or composition that, when administered, is sufficient to prevent development of, or alleviate to some extent, one or more of the symptoms of the disorder, disease, or condition being treated.

The term "bioisostere" (or simply isostere) is a term of art used to define drug analogues in which one or more atoms (or groups of atoms) have been substituted with replacement atoms (or groups of atoms) having similar steric and/or electronic features to those atoms which they replace. The substitution of a hydrogen atom or a hydroxyl group with a fluorine atom is a commonly employed bioisosteric replacement. Sila-substitution (C/Si-exchange) is a relatively recent technique for producing isosteres. This approach involves the replacement of one or more specific carbon atoms in a compound with silicon (for a review, see Tacke and Zilch (1986) Endeavour, New Series 10: 191-197). The sila-substituted isosteres (silicon isosteres) may exhibit improved pharmacological properties, and may for example be better tolerated, have a longer half-life or exhibit increased potency (see for example Englebienne (2005) Med. Chem., 1(3): 215-226). Similarly, replacement of an atom by one of its isotopes, for example hydrogen by deuterium, may also lead to improved pharmacological properties, for example leading to longer half-life (see for example Kushner et al (1999) Can J Physiol Pharmacol. 77(2):79-88). In its broadest aspect, the present invention contemplates all bioisosteres (and specifically, all silicon bioisosteres) of the compounds of the invention.

In the general formulae of the present invention, the bond orders of the specified rings may vary when the various possible heteroatom(s) imply specific requirements in order to satisfy aromaticity, prevent antiaromaticity and stabilize tautomeric forms due to localization. In such cases, the appropriate bond orders of the ring structures in the structural formulae of the present invention are contemplated herein.

In its broadest aspect, the present invention contemplates all optical isomers, racemic forms and diastereoisomers of the compounds described herein. Those skilled in the art will appreciate that, owing to the asymmetrically substituted carbon atoms present in the compounds of the invention, the compounds may be produced in optically active and racemic forms. If a chiral centre or another form of isomeric centre is present in a compound of the present invention, all forms of such isomer or isomers, including enantiomers and diastereoisomers, are intended to be covered herein. Compounds of the invention containing a chiral centre (or multiple chiral centres) may be used as a racemic mixture, an enantiomerically enriched mixture, or the racemic mixture may be separated using well-known techniques and an individual enantiomer may be used alone. Thus, references to particular compounds of the present invention encompass the products as a mixture of diastereoisomers, as individual diastereoisomers, as a mixture of enantiomers as well as in the form of individual enantiomers.

Therefore, the present invention contemplates all optical isomers and racemic forms thereof of the compounds of the invention, and unless indicated otherwise (e.g. by use of dash-wedge structural formulae) the compounds shown herein are intended to encompass all possible optical isomers of the compounds so depicted. In cases where the stereochemical form of the compound is important for pharmaceutical utility, the invention contemplates use of an isolated eutomer.

The term "pharmaceutically acceptable derivative" as applied to the compounds of the invention define compounds which are obtained (or obtainable) by chemical derivatization of the parent compounds of the invention. The pharmaceutically acceptable derivatives are therefore suitable for administration to or use in contact with mammalian tissues without undue toxicity, irritation or allergic response (i.e. commensurate with a reasonable benefit/risk ratio). Preferred derivatives are those obtained (or obtainable) by alkylation, esterification or acylation of the parent compounds of the invention. The derivatives may be active per se, or may be inactive until processed in vivo. In the latter case, the derivatives of the invention act as prodrugs. Particularly preferred prodrugs are ester derivatives which are esterified at one or more of the free hydroxyls and which are activated by hydrolysis in vivo. Other preferred prodrugs are covalently bonded compounds which release the active parent drug according to general formula (I) or (Ia) after cleavage of the covalent bond(s) in vivo.

The term "pharmaceutically acceptable salt" as applied to the compounds of the invention defines any non-toxic organic or inorganic acid addition salt of the free base which are suitable for use in contact with the tissues of humans and lower animals without undue toxicity, irritation, allergic response and which are commensurate with a reasonable benefit/risk ratio. Suitable pharmaceutically acceptable salts are well known in the art. Examples are the salts with inorganic acids (for example hydrochloric, hydrobromic, sulphuric and phosphoric acids), organic carboxylic acids (for example acetic, propionic, glycolic, lactic, pyruvic, malonic, succinic, fumaric, malic, tartaric, citric, ascorbic, maleic, hydroxymaleic, dihydroxymaleic, benzoic, phenylacetic, 4-aminobenzoic, 4-hydroxybenzoic, anthranilic, cinnamic, salicylic, 2-phenoxybenzoic, 2-acetoxybenzoic and mandelic acid) and organic sulfonic acids (for example methanesulfonic acid and p-toluenesulfonic acid). Salt forms may be selected and prepared according to methods described in Pharmaceutical Salts: Properties, Selection, and Use, P. Heinrich Stahl (Editor), Camille G. Wermuth (Editor), ISBN: 3-90639-026-8, Hardcover, 388 pages, August 2002.

The term "ligand" as used herein to define a binding partner for a biological target molecule in vivo (for example, an enzyme or receptor). The ligands for use according to the invention are preferably small molecules that can be functionalized by the addition of a bioorthogonal click reactive moiety via a linker.

As used herein, the term "small molecule" means any molecule having a molecular weight of 1000 Da or less, for example less than 900 Da, less than 800 Da or less than 600 Da.

Bioorthocional Click Reactions and Compatible Reactant Pairs Therefor

The invention exploits a bioorthogonal click reaction between a compatible pair of reactive moieties located on CLIPTAC precursor components (as shown schematically in FIG. 1). The reactive moieties (also referred to herein as bioorthogonal click reactants) are therefore selected by reference to the particular click chemistry employed, and so any of a wide range of compatible pairs of bioorthogonal click reactants known to those skilled in the art may be used according to the invention.

One member of the compatible pair of reactive moieties forms part of a first component comprising a ligand for an intracellular target protein, while the other forms part of a second component comprising a ligand for an E3 ubiquitin ligase.

In general, either of the reactive moieties may be chosen for the aforementioned components, provided that the resultant functionalized components bear reactive moieties which are compatible (in the sense that they undergo a bioorthogonal click chemical reaction to assemble into a functional PROTAC as described herein).

Exemplary bioorthogonal click chemistries and the corresponding compatible bioorthogonal reactant pairs suitable for use in the invention are described in more detail below:

Inverse Electron Demand Diels-Alder Cycloaddition Reaction (IEDDA)

One of the most efficient bioorthogonal reactions is the Inverse Electron Demand Diels-Alder (IEDDA) cycloaddition (Devaraj et al. (2008) Tetrazine-Based Cycloadditions: Application to Pretargeted Live Cell Imaging. *Bioconjug. Chem.* 19: 2297-2299; Blackman et al. (2008) Tetrazine Ligation: Fast Bioconjugation Based on Inverse-Electron-Demand Diels-Alder Reactivity. *J. Am. Chem. Soc.* 130: 13518-13519). It is based on the inverse electron demand [4+2] Diels-Alder (IEDDA) cycloaddition between a 1,2,4, 5-tetrazine and a strained alkene dienophile. This reaction is selective, high-yielding, clean, biocompatible and bioorthogonal.

The reaction proceeds in two steps: first, the tetrazine and dienophile undergo an IEDDA cycloaddition to form a tricyclic species with a dinitrogen bridge, and this intermediate then undergoes a retro-Diels-Alder reaction driven by the release of dinitrogen to form a stable dihydropyridazine product. The rapidity of the ligation is governed largely by the identity of the two click reactants. Early work used derivatives of norbornene as the dienophile: this has since been superseded by dienophiles based on trans-cyclooctene (TCO). The reaction between tetrazine and trans-cyclooctene (TCO) was shown to be fast and high yielding (Selvaraj et al. (2013) trans-Cyclooctene—a stable, voracious dienophile for bioorthogonal labeling. *Curr. Opin. Chem. Biol.* 17: 753-760), and does not require the presence of a catalyst (Patterson et al. (2014) Finding the Right (Bioorthogonal) Chemistry. *ACS Chem. Biol.* 9: 592-605). The IEDDA has found numerous biological applications, especially in the imaging field (Tsai et al. (2015) Selective, rapid and optically switchable regulation of protein function in live mammalian cells. *Nat. Chem.* 7: 554-561; Yang et al. (2012) Bioorthogonal Imaging of Aurora Kinase A in Live Cells. *Angew. Chem. Int. Ed.* 51: 6598-6603; Reiner et al. (2010) Bioorthogonal Small-Molecule Ligands for PARP1 Imaging in Living Cells. *Chem Bio Chem* 11: 2374-2377; Keinänen et al. (2016) A New Highly Reactive and Low Lipophilicity Fluorine-18 Labeled Tetrazine Derivative for Pretargeted PET Imaging. *ACS Med. Chem. Lett.* 7: 62-66).

A number of different 1,2,4,5-tetrazines have also been tested for their influence on reaction kinetics, revealing rate constants with trans-cyclooctene ranging from 210 $M^{-1}$ $s^{-1}$ to almost 30,000 $M^{-1}$ $s^{-1}$. The more stable tetrazines generally react less rapidly, while the less stable compounds generally react more quickly.

Thus, any suitable compatible diene and dienophile pair may be used as compatible reactive moieties in embodiments where the bioorthogonal click reaction is an IEDDA cycloaddition, as described in more detail below.

Diene Reactive Groups

Dienes useful in the present disclosure include but are not limited to aromatic ring systems that contain two adjacent nitrogen atoms, for example, tetrazines, pyridazines, substituted or unsubstituted 1,2-diazines. Other 1,2-diazines can include 1,2-diazines annelated to a second rr-electron-deficient aromatic ring such as pyrido[3,4-d]pyridazines, pyridazino[4,5-d]pyridazines and 1,2,4-triazines. Pyridazines can also be fused with a five-membered heterocycle such as imidazo[4,5-d]pyridazines and 1,2,3-triazolo [4,5-d]pyridazines.

Thus, in some embodiments, the diene group comprises a heteroaromatic ring system possessing at least two adjacent nitrogens. In such cases, the diene group may be selected from: pyridazines, substituted or unsubstituted 1,2-diazines, pyrido[3,4-d]pyridazines, pyridazino[4,5-d]pyridazines, triazines, imidazo[4,5-d]pyridazines and 1,2,3-triazolo[4,5-d] pyridazines.

In other preferred embodiments, the diene group may comprise a tetrazine, for example an asymmetrical tetrazine (e.g. 3-(p-benzylamino)-1,2,4,5-tetrazine) or a functionalized 1,2,4,5-tetrazine. A wide variety of suitable functionalized tetrazines are described in WO2010/051530 and WO2014/065860 (the contents of which relating to tetrazine reactive groups for IEDDA are specifically incorporated herein by reference).

Other suitable dienes may be readily synthesised according to the methods described in the literature, including for example Wu et al. (2014) *In situ synthesis of alkenyl tetrazines for highly fluorogenic bioorthogonal live-cell imaging probes. Angew. Chem. Int. Ed. Engl.* 53: 5805-5809; Yang et al. (2012) *Metal-catalyzed one-pot synthesis of tetrazines directly from aliphatic nitriles and hydrazine. Angew. Chem. Int. Ed. Engl.* 51: 5222-5225; and Yang et al. (2014) *Synthesis and reactivity comparisons of 1-methyl-3-substituted cyclopropene minitags for tetrazine bioorthogonal reactions. Chemistry* 20: 3365-3375 (the contents of which relating to the synthesis of tetrazine reactive groups for IEDDA are specifically incorporated herein by reference).

Dienophile Reactive Groups

Dienophiles useful in the present methods and compositions include but are not limited to carbon containing dienophiles such as alkenes or alkynes, or compounds containing nitroso, carbonyl or imine groups. In some embodiments, the dienophile is a strained dienophile. As used herein, a "strained" dienophile has a dihedral angle that deviates from the idealized 180 degree dihedral angle. Alternatively, non-strained dienophiles (e.g. styrenes) and/ or electron rich electrophiles (e.g. eneamines or vinyl ethers), can also be used with nitroso compounds. Alkenes in this context includes alkyl groups having one or more double carbon-carbon bonds such as an ethylene, propylene, as well as cyclic, ring-strained alkenes such as trans-cyclooctene or norbomene carrying a double bond which induces significant ring strain (and which is therefore activated towards cycloaddition). Alkenes can also include more complex structures such as indoles, azaindoles and electron rich enamines. Heterodienophiles containing carbonyl, nitroso or imine groups can also be used. In some preferred embodiments, the dienophile is a trans-cyclooctenol, e.g., (E)-cyclooct-4-enol.

Thus, suitable dienophile groups include alkenes, for example a straight chain alkenes such as ethylene or propylene. Other suitable dienophile groups include alkynes, such as an internal alkyne, terminal alkyne or cyclic alkyne.

In some embodiments, the dienophile group comprises a strained alkene or strained alkyne. In such cases, the dienophile group comprises a strained alkene selected from norbornene, trans-cyclooctene (TCO), cyclopropene and vinyl.

Another suitable dienophile group comprises bicyclo [6.1.0]non-4-yn-9-ylmethanol (BCN).

Other suitable dienophile reactive groups are described in McKay and Finn (2014) *Click Chemistry in Complex Mixtures: Bioorthogonal Bioconjugation*. Chemistry & Biology 21(9): 1075-1101 (see in particular Table 5), the contents of which relating to dienophile reactive groups for IEDDA are specifically incorporated herein by reference.

Strain-Promoted Alkyne Azide Cycloaddition (SPAAC)

"Strain-Promoted Alkyne-Azide Cycloaddition" (SPAAC) reactions (reviewed in McKay and Finn, op. cit.) have been used effectively in a variety of in vivo contexts, including in mammalian cells and animals. Here, the reactive moieties are an azide group and a strained alkyne group which individually are inert to biological functionalities (such as amines, thiols, acids and carbonyls) but which undergo rapid and irreversible cycloaddition leading to a stable triazole product.

Application of SPAAC was initially limited by the availability of strained alkyne reactants, but following intense efforts a wide range of substituted cyclooctynes have been developed. These include the cyclic alkynes described in US 2009/0068738 (the contents of which relating to reactive groups for SPAAC are specifically incorporated herein by reference) and cyclooctynes such as azadibenzocyclooctyne (ADIBO, DIBAC or DBCO), tetramethyldibenzocyclooctyne (TMDIBO), cyclooctyne (OCT), aryl-less cyclooctyne (ALO), monofluorocyclooctyne (MOFO), difluorocyclooctyne (DIFO), dibenzocyclooctyne (DIBO), dimethoxyazacyclooctyne (DIMAC), biarylazacyclooctynone (BARAC), bicyclononyne (BCN), tetramethylthiepinium (TMTI, TMTH), difluorobenzocyclooctyne (DIFBO), oxa-dibenzocyclooctyne (ODIBO), carboxymethylmonobenzocyclooctyne (COMBO) and benzocyclononyne.

Staudinger Ligation

The Staudinger-inspired reaction ("Staudinger ligation") between azides and phosphanes to yield amide linkages developed by Bertozzi and coworkers is a modification of the classical Staudinger reaction that is an established bioorthogonal process and remains extremely useful (Saxon and Bertozzi (2000) Science: 287, 2007-2010).

The classical Staudinger reaction is a chemical reaction in which the combination of an azide with a phosphine or phosphite produces an aza-ylide intermediate, which upon hydrolysis yields a phosphine oxide and an amine. The Staudinger ligation introduced by Saxon and Bertozzi exploits the smooth reaction between an azide and a phosphane to form a phospha-aza-ylide. This ylide can be trapped by an acyl group with formation of a stable amide bond. The Staudinger reaction is a mild method of reducing an azide to an amine; and triphenylphosphine is commonly used as the reducing agent. In a Staudinger ligation, an electrophilic trap (usually a methyl ester) is appropriately placed on the aryl group of a triarylphosphine (usually ortho to the phosphorus atom) and reacted with the azide, to yield an aza-ylide intermediate, which rearranges in aqueous media to produce a compound with amide group and a phosphine oxide function. The by-product phosphane oxide can remain attached to, or can be released from, the final product.

The Staudinger ligation is so named because it ligates (attaches/covalently links) the two starting molecules together, whereas in the classical Staudinger reaction, the two products are not covalently linked after hydrolysis. This reaction has been reviewed in Köhn and Breinbauer (2004) *The Staudinger Ligation—A Gift to Chemical Biology Angew. Chem. Int. Ed.* 43: 3106-3116.

Any suitable azide and phosphane group may be used as compatible reactive moieties in embodiments where the bioorthogonal click reaction is a Staudinger ligation. Both nontraceless and traceless Staudinger reactions may be employed (as described in Köhn and Breinbauer, op. cit.). In certain embodiments, the phosphane can be a di- or triarylphosphane to stabilize the phosphine. The phosphanes used in the Staudinger ligation methods described herein therefore include, but are not limited to, cyclic or acyclic, halogenated, bisphosphorus and polymeric phosphanes. The azides may for example be selected from alkyl, aryl, acyl or phosphoryl azides.

Other bioorthogonal click chemistries and the corresponding compatible bioorthogonal reactant pairs suitable for use in the invention include: (a) ligations based on rigid cyclic diol (nopoldiol) and 2-methyl-5-carboxymethylphenylboronic acid (Akgun and Hall (2016) *Fast and Tight Boronate Formation for Click Bioorthogonal Conjugation Angewandte Chemie, International Edition* 55(12): 3909-3913); and (b) the click ligations described in Li et al. (2016) *Tetrazole Photoclick Chemistry: Reinvestigating Its Suitability as a Bioorthogonal Reaction and Potential Applications* Angewandte Chemie, International Edition (2016): 55(6): 2002-2006.

Linkers

The CLIPTACs of the invention comprise a linker portion covalently coupling the first and second portions and containing a covalent bond produced by a bioorthogonal click reaction between a compatible pair of reactive moieties.

In the CLIPTAC precursor compositions of the invention, the first and/or second reactive moieties may be located on a linker portion of the first and/or second components, respectively. In such cases, the linker portion of the first and/or second components may be such that a linker as described below is formed after self-assembly.

When present on a CLIPTAC precursor of the invention, the linker portion is solvent proximal when the ligand portion of the precursor is bound to its target, so that the reactive moiety is available for bioorthogonal click reaction with its compatible counterpart.

In preferred embodiments, compatible pairs of CLIPTAC precursors both comprise a linker portion bearing a bioorthogonal click reactive moiety.

The linker may take any form, provided that it does not significantly interfere with binding of the ligand to the target, or with the bioorthogonal click reaction. In some embodiments, the linker is constituted by those parts of the ligand which are exposed to solvent when the ligand is bound to the target. In other embodiments, the linker may be a series of stable covalent bonds incorporating one or more (e.g. 1-500) non-hydrogen atoms selected from the group consisting of C, N, O, S and P.

Exemplary linkers therefore include moieties comprising —C(O)NH—, —C(O)O—, —NH—, —S— and —O— groups. Other suitable linkers may also be comprised of the atoms or groups including (but not limited to), carbon, amino, alkylamino, oxygen, sulfur, sulfoxide, sulfonyl, carbonyl and imine. The linker chain may also comprise part of a saturated, unsaturated or aromatic ring, including polycyclic and heteroaromatic rings wherein the heteroaromatic ring is an aryl group containing from one to four heteroatoms, N, O or S. Specific examples include, but are not limited to, saturated alkanes, unsaturated alkanes, polyethylene glycols and dextran polymers.

The click reaction of the reactive moieties therefore effects covalent bonding of the two ligands via a linker moiety which comprises, consists, or consists essentially of the covalent bond(s) produced by the bioorthogonal click reaction between the compatible pair of reactive moieties. Thus, in the case of IEDDA-based click chemistry, the linker moiety formed on self-assembly of the CLIPTAC in vivo may comprise a dihydropyrazine group (in cases where the dienophile is an alkene) or a pyrazine group (in cases where the dienophile is an alkyne), though it should be noted that the dihydropyrazine reaction product in the first case may undergo an additional oxidation step in vivo to yield the corresponding pyrazine. In the case of SPAAC-based click chemistry, the linker moiety formed on self-assembly of the CLIPTAC in vivo may comprise a triazole moiety.

The linker is of a length appropriate to bring together target protein and ubiquitinating machinery and thereby elicit the ubiquitination of the protein of interest and its subsequent degradation in the proteasome. It is therefore to be understood that the linker of the CLIPTAC of the invention serves as a spacer, physically separating the target and ligase ligands to a degree sufficient to ensure that binding with their respective targets when self-assembled as a CLIPTAC is not rendered mutually exclusive as a result of steric inhibition. In the absence of a linker, or if the linker is too short, the interaction between the target and ligase ligands of the self-assembled CLIPTAC and their respective targets could be disrupted.

However, it will also be understood that the linker should also not be too long, since in such cases the bound E3 ligase might not be in sufficiently close spatial proximity to the target protein to trigger its ubiquitination.

Those skilled in the art will therefore appreciate that the length of the linker is preferably optimized by reference inter alia to target and E3 ligase binding efficiency as well as target protein ubiquitination.

In some embodiments, the linker may be 1-21 bonds in length, for example 1-20, 1-19, 1-18, 1-17, 1-16, 1-15, 1-14, 1-13, 1-12, 1-11, 1-10, 1-9, 1-8, 1-7, 1-6, 1-5, 1-4, 1-3 or 1-2 bonds in length. In other embodiments, the linker may be 2-21 bonds in length, for example 3-21, 4-21, 5-21, 6-21, 7-21, 8-21, 9-21, 10-21, 11-21, 12-21, 13-21, 14-21, 15-21, 16-21, 17-21, 18-21, 18-21, 19-21 or 20-21 bonds in length.

Methods for the Preparation of CLIPTAC and CLIPTAC PRECURSORS

Described below is the synthesis of a tetrazine tagged thalidomide (Tz-thalidomide), a component of a self-assembling CLIPTAC that can 'click' with a TCO-tagged inhibitor and then recruit the E3 ligase CRBN to the protein of interest for ubiquitination and then degradation (FIG. 1).

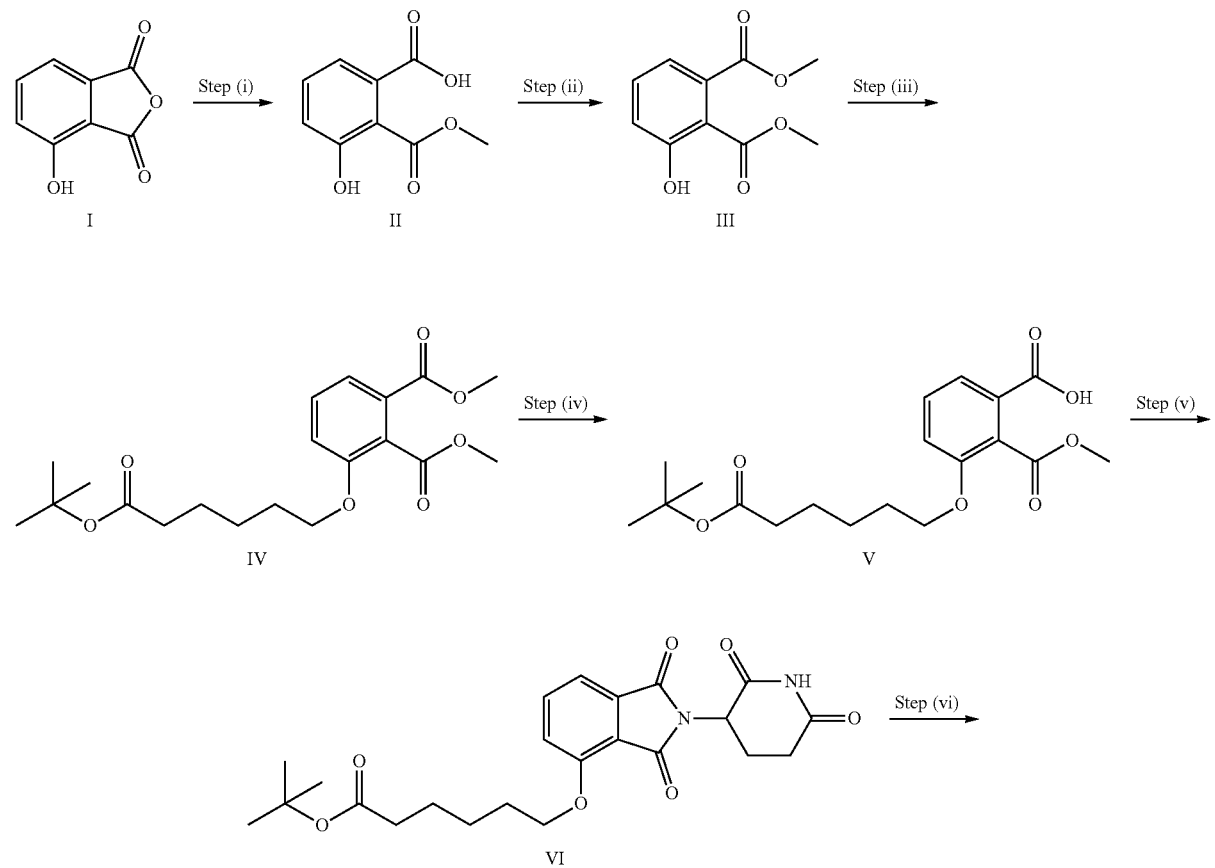

Scheme 1

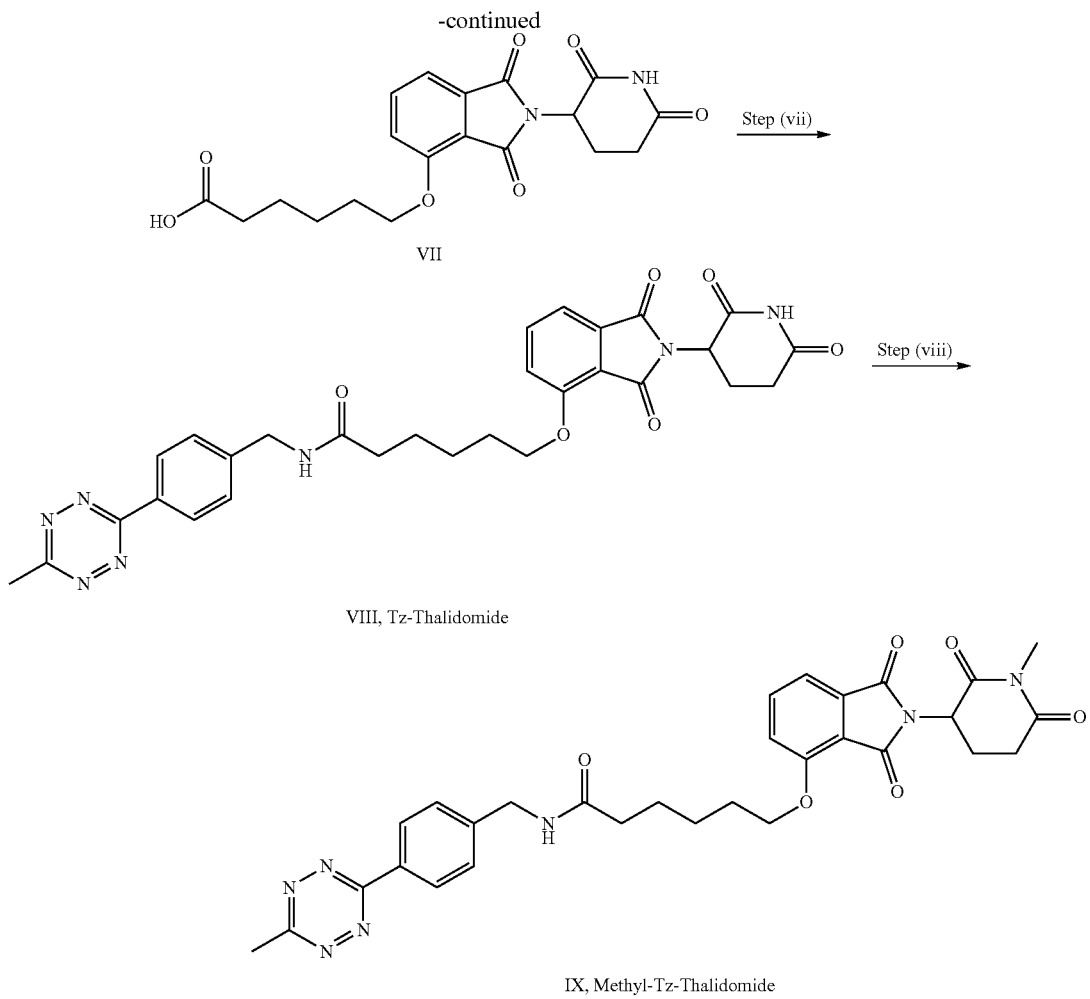

VIII, Tz-Thalidomide

IX, Methyl-Tz-Thalidomide

Step (i) of Scheme 1 typically comprises stirring a compound of formula (I) in methanol for a suitable period such a 3 hours. Such process may be carried out at elevated temperature e.g. 65° C. An example procedure for step (i) is shown herein in Preparation 1.

Step (ii) of Scheme 1 typically comprises stirring a compound of formula (II) with a suitable base such as sodium bicarbonate in a suitable solvent such as N,N-dimethylformamide, followed by treatment with a suitable alkylating agent such as methyl iodide. Such a process may be carried out at elevated temperature e.g. 55° C. for a suitable period such as 3 hours. An example procedure for step (ii) is shown herein in Preparation 1.

Step (iii) of Scheme 1 typically comprises stirring a compound of formula (III) with tert-butyl 6-hydroxyhexanoate in the presence of a phosphine ligand such as triphenylphosphine, and a compound of formula R$^1$O(CO)N=N(CO)OR$^1$, wherein R$^1$ is an alkyl group such as ethyl, isopropyl or butyl, in a suitable solvent such as tetrahydrofuran for a suitable period such as 18 hours. Such a process may be carried out at ambient temperature. An example procedure for step (iii) is shown herein in Preparation 2.

Step (iv) of Scheme 1 typically comprises stirring a compound of formula (IV) with a suitable base such as sodium hydroxide in a suitable solvent such as a mixture of tetrahydrofuran and methanol for a suitable period such as 2 hours. Such a process may be carried out at ambient temperature. An example procedure for step (iv) is shown herein in Preparation 3.

Step (v) of Scheme 1 typically comprises stirring a compound of formula (V) with 3-aminopiperidine-2,6-dione in a suitable solvent such as pyridine for a suitable period such as 17 hours. Such a process may be carried out at elevated temperature e.g. 110° C. An example procedure for step (v) is shown herein in Preparation 4.

Step (vi) of Scheme 1 typically comprises stirring a compound of formula (VI) with a suitable acid such as trifluoroacetic acid for a suitable period such as 3 hours. Such a process may be carried out at ambient temperature. An example procedure for step (vi) is shown herein in Preparation 4.

Step (vii) of Scheme 1 typically comprises stirring a compound of formula (VII) with [4-(6-methyl-1,2,4,5-tetrazin-3-yl)phenyl]methanamine, a suitable base such as N,N-diisopropylethylamine, and a coupling agent such as HATU in a suitable solvent such as N,N-dimethylformamide for a suitable period such as 2 hours. Such a process may be carried out at ambient temperature. An example procedure for step (vii) is shown herein in Example 1.

Step (viii) of Scheme 1 typically comprises stirring a compound of formula (VIII) with a suitable base such as sodium hydride in a suitable solvent such as tetrahydrofuran for a suitable period such as 30 min, followed by treatment with a suitable alkylating agent such as methyl iodide. Such a process may be carried out at 0° C. followed by ambient temperature. An example procedure for step (viii) is shown herein in Example 2.

Described below is the synthesis of a TCO-tagged inhibitor of BRD4, which is a component of a self-assembling CLIPTAC that can 'click' with a tetrazine-tagged E3 ligase recruiter to target BRD4 for ubiquitination and then degradation.

in a suitable solvent such as N,N-dimethylformamide for a suitable period such as 16 hours. Such a process may be carried out at ambient temperature. An example procedure for step (ii) is shown herein in Example 3.

Described below is the synthesis of a TCO-tagged inactive enantiomer of an inhibitor of BRD4, which can be used as a negative control in experiments to study self-assembling CLIPTACs that can 'click' with a tetrazine-tagged E3 ligase recruiter to target BRD4 for ubiquitination and then degradation.

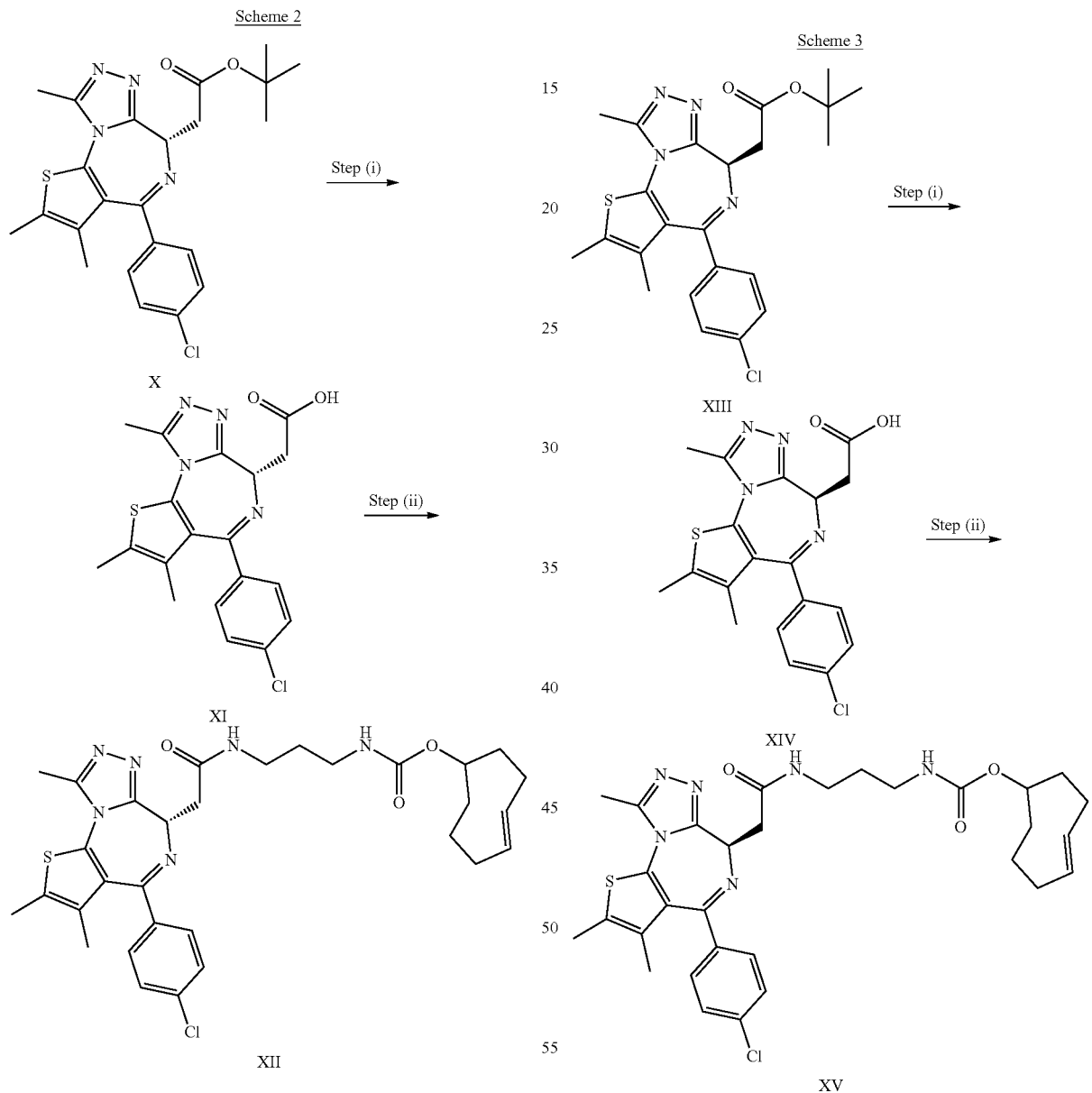

Step (i) of Scheme 2 typically comprises stirring a compound of formula (X) with a suitable acid such as trifluoroacetic acid in a suitable solvent such as dichloromethane for a suitable time period such as 3 hours. Such a process may be carried out at ambient temperature. An example procedure for step (i) is shown herein in Preparation 5.

Step (ii) of Scheme 2 typically comprises stirring a compound of formula (XI) with trans-cyclooct-4-en-1-yl N-(3-aminopropyl)carbamate, a suitable base such as N,N-diisopropylethylamine, and a coupling agent such as HATU Step (i) of Scheme 3 typically comprises stirring a compound of formula (XIII) with a suitable acid such as trifluoroacetic acid in a suitable solvent such as dichloromethane for a suitable time period such as 3 hours. Such a process may be carried out at ambient temperature. An example procedure for step (i) is shown herein in Preparation 6.

Step (ii) of Scheme 3 typically comprises stirring a compound of formula (XIV) with trans-cyclooct-4-en-1-yl N-(3-aminopropyl)carbamate a suitable base such as N,N- diisopropylethylamine, and a coupling agent such as HATU in a suitable solvent such as N,N-dimethylformamide for a suitable period such as 16 hours. Such a process may be carried out at ambient temperature. An example procedure for step (ii) is shown herein in Example 4.

Described below and shown in Schemes 4-6 is the synthesis of a TCO-tagged inhibitor of ERK1/2, which is a component of a self-assembling CLIPTAC that can 'click' with a tetrazine-tagged E3 ligase recruiter to target ERK1/2 for ubiquitination and then degradation.

Scheme 4

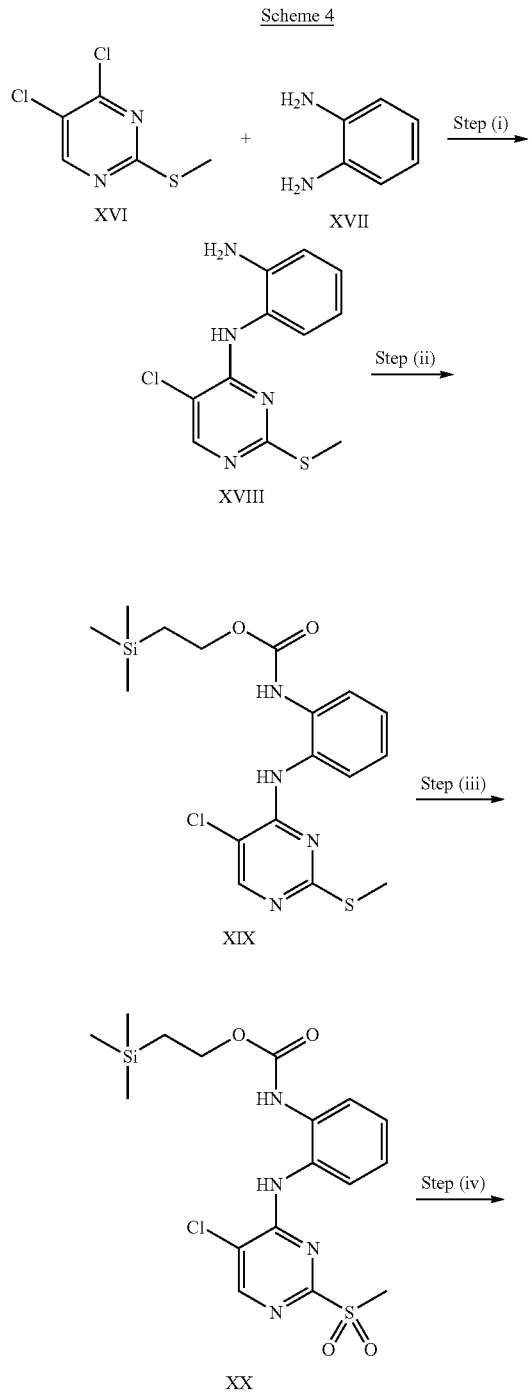

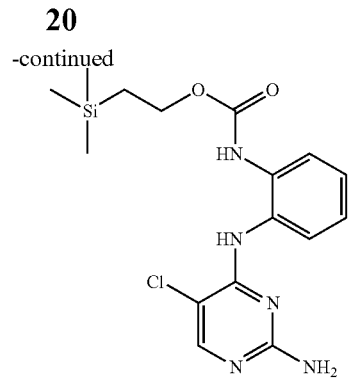

XXI

Step (i) of Scheme 4 typically comprises stirring a compound of formula (XVI) and a compound of formula (XVII) with a suitable base such as N,N-diisopropylethylamine in a suitable solvent such as n-butanol for a suitable period such as 3 hours. Such a process may be carried out at elevated temperature e.g. 110° C. An example procedure for step (i) is shown herein in Preparation 7.

Step (ii) of Scheme 4 typically comprises stirring a compound of formula (XVIII) with a suitable base such as triethylamine and an activated carbamate such as 2-(trimethylsilyl)ethyl N-{2-[(2-amino-5-chloropyrimidin-4-yl)amino]phenyl} carbamate in a suitable solvent such as a mixture of acetonitrile and tetrahydrofuran for a suitable period such as 5 hours. Such a process may be carried out at elevated temperature e.g. 70° C. An example procedure for step (ii) is shown herein in Preparation 8.

Step (iii) of Scheme 4 typically comprises stirring a compound of formula (XIX) with a suitable oxidising agent such as 3-chloroperoxybenzoic acid in a suitable solvent such as dichloromethane for a suitable period such as 2 hours. Such a process may be carried out at ambient temperature. An example procedure for step (iii) is shown herein in Preparation 9.

Step (iv) of Scheme 4 typically comprises stirring a compound of formula (XX) with a suitable base such as ammonium hydroxide in a suitable solvent such as dioxan for a suitable period such as 20 hours. Such a process may be carried out at elevated temperature e.g. 80° C. An example procedure for step (iv) is shown herein in Preparation 10.

Scheme 5

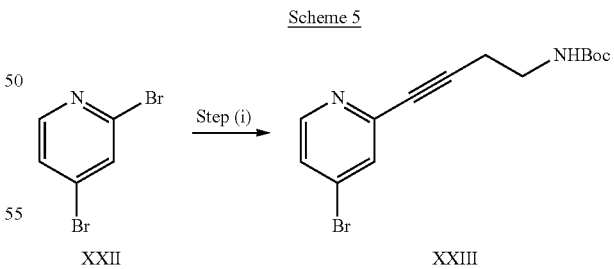

Step (i) of Scheme 5 typically comprises stirring a compound of formula (MI) with tert-butyl but-3-ynylcarbamate in presence of a suitable catalyst such as Pd(PPh$_3$)$_2$Cl$_2$ and Cu(I)I and a suitable base such as N,N-diisopropylethylamine in a suitable solvent such as tetrahydrofuran in an inert atmosphere for a suitable period such as 24 hours. Such a process may be carried out at ambient temperature. An example procedure for step (i) is shown herein in Preparation 11.

Scheme 6
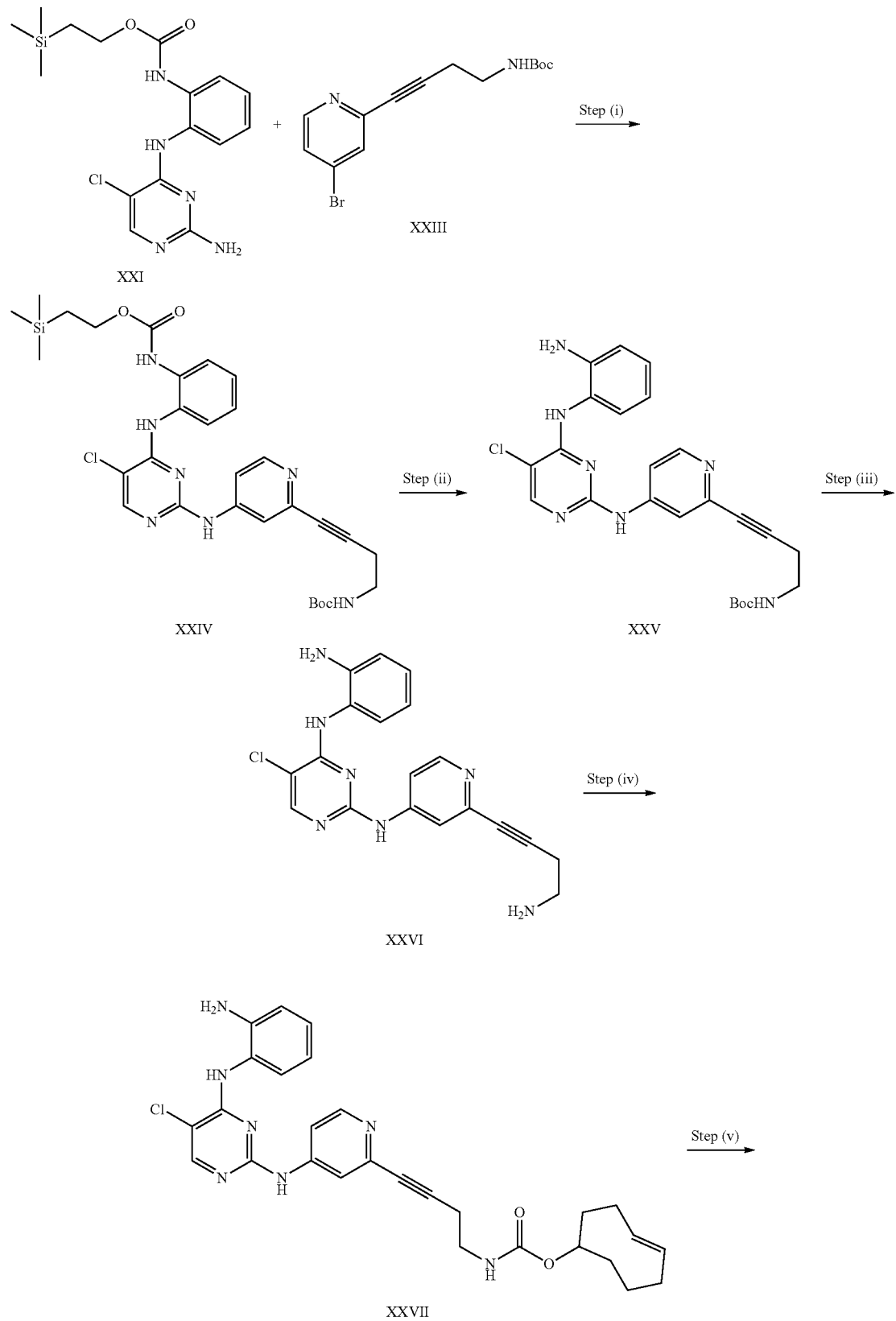

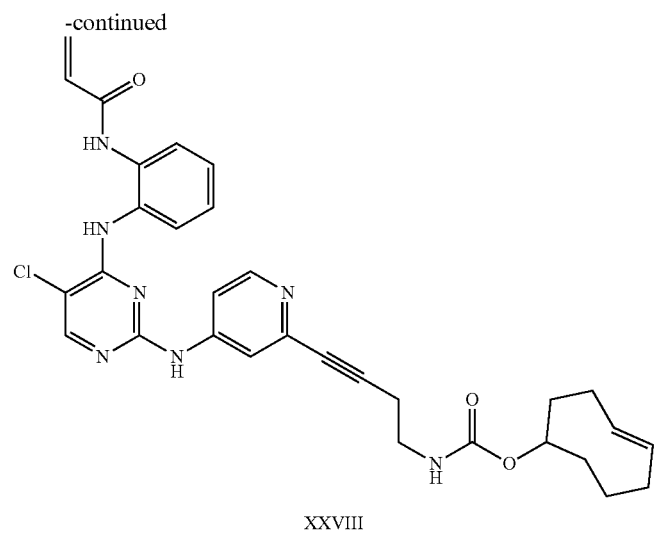

XXVIII

Step (i) of Scheme 6 typically comprises stirring a compound of formula (XXI) and a compound of formula (XXII) with a suitable catalyst such as Pd(dba)₂, a suitable ligand such as XPhos and a suitable base such as potassium carbonate in a suitable solvent solvent such as acetonitrile in an inert atmosphere for a suitable period such as 18 hours. Such a process may be carried out at elevated temperature e.g. 80° C. An example procedure for step (i) is shown herein in Preparation 12.

Step (ii) of Scheme 6 typically comprises stirring a compound of formula (XXIV) with tetrabutylammonium fluoride in a suitable solvent such as tetrahydrofuran for a suitable period such as 2 hours. Such a process may be carried out at elevated temperature e.g. 40° C. An example procedure for step (ii) is shown herein in Preparation 13.

Step (iii) of Scheme 6 typically comprises stirring a compound of formula (XXV) with a suitable acid such as hydrogen chloride in a suitable solvent such as a mixture of dichloromethane and methanol for a suitable period such as 18 hours. Such a process may be carried out at ambient temperature. An example procedure for step (iii) is shown herein in Preparation 14.

Step (iv) of Scheme 6 typically comprises stirring a compound of formula (XXVI) with a suitable base such as N,N-diisopropylethylamine and trans-cyclooct-4-en-1-yl 2,5-dioxopyrrolidin-1-yl carbonate in a suitable solvent such as N,N-dimethylformamide for a suitable period such as 30 min. Such a process may be carried out at ambient temperature. An example procedure for step (iv) is shown herein in Preparation 14.

Step (v) of Scheme 6 typically comprises stirring a compound of formula (XXVII) with acryloyl chloride with a suitable base such as N,N-diisopropylethylamine in a suitable solvent such as tetrahydrofuran for a suitable period such as 30 min. Such a process may be carried out at 0° C. An example procedure for step (v) is shown herein in Example 5.

Described below in Schemes 7-10 are the syntheses of tetrazine tagged thalidomide (Tz-thalidomide) CLIPTAC precursors with alternative linker lengths connecting the tetrazine moiety to the thalidomide-based recruiter of the E3 ligase CRBN, which can 'click' with a TCO-tagged inhibitor and then recruit the E3 ligase CRBN to the protein of interest for ubiquitination and then degradation.

Scheme 7

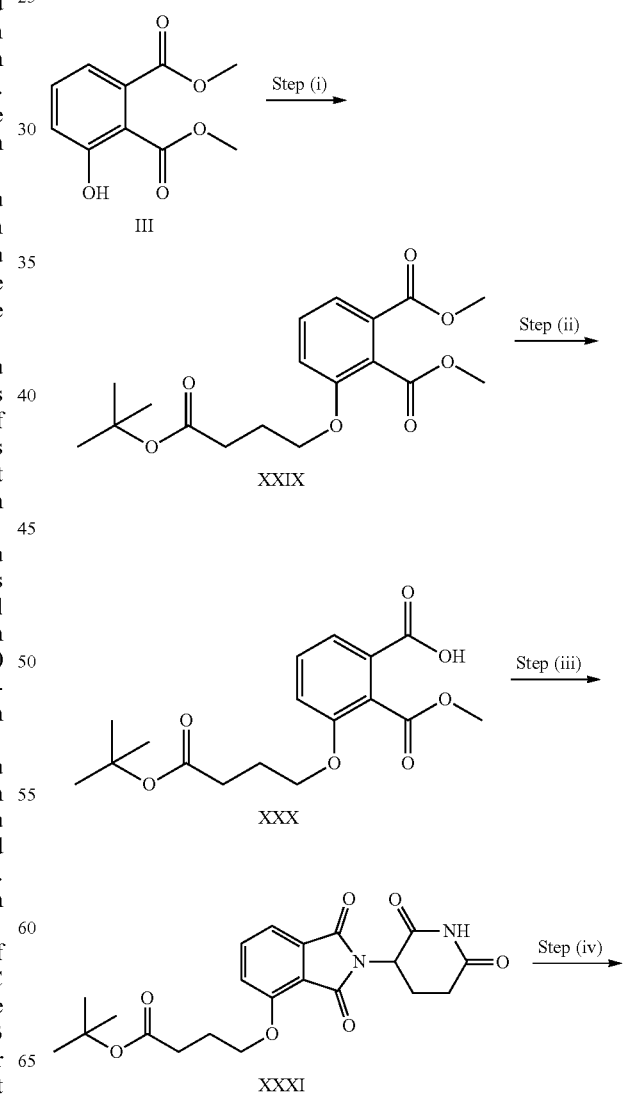

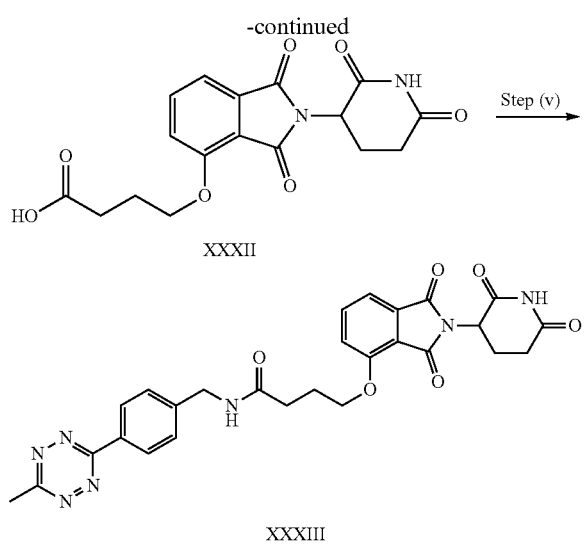

Step (i) of Scheme 7 typically comprises stirring a compound of formula (III) with tert-butyl 4-bromobutanoate with a suitable base such as potassium carbonate in a suitable solvent such as N,N-dimethylformamide for a suitable period such as 18 hours. Such a process may be carried out at elevated temperature e.g. 50° C. An example procedure for step (i) is shown herein in Preparation 15.

Step (ii) of Scheme 7 typically comprises stirring a compound of formula (XXIX) with a suitable base such as sodium hydroxide in a suitable solvent such as a mixture of tetrahydrofuran and methanol for a suitable period such as 2 hours. Such a process may be carried out at ambient temperature. An example procedure for step (ii) is shown herein in Preparation 16.

Step (iii) of Scheme 7 typically comprises stirring a compound of formula (XXX) with 3-aminopiperidine-2,6-dione in a suitable solvent such as pyridine for a suitable period such as 17 hours. Such a process may be carried out at elevated temperature e.g. 110° C. An example procedure for step (iii) is shown herein in Preparation 17.

Step (iv) of Scheme 7 typically comprises stirring a compound of formula (XXXI) with a suitable acid such as trifluoroacetic acid for a suitable period such as 3 hours. Such a process may be carried out at ambient temperature. An example procedure for step (iv) is shown herein in Preparation 17.

Step (v) of Scheme 7 typically comprises stirring a compound of formula (XXXII) with [4-(6-methyl-1,2,4,5-tetrazin-3-yl)phenyl]methanamine, a suitable base such as N,N-diisopropylethylamine, and a coupling agent such as HATU in a suitable solvent such as N,N-dimethylformamide for a suitable period such as 1 hour. Such a process may be carried out at ambient temperature. An example procedure for step (v) is shown herein in Example 6.

Scheme 8

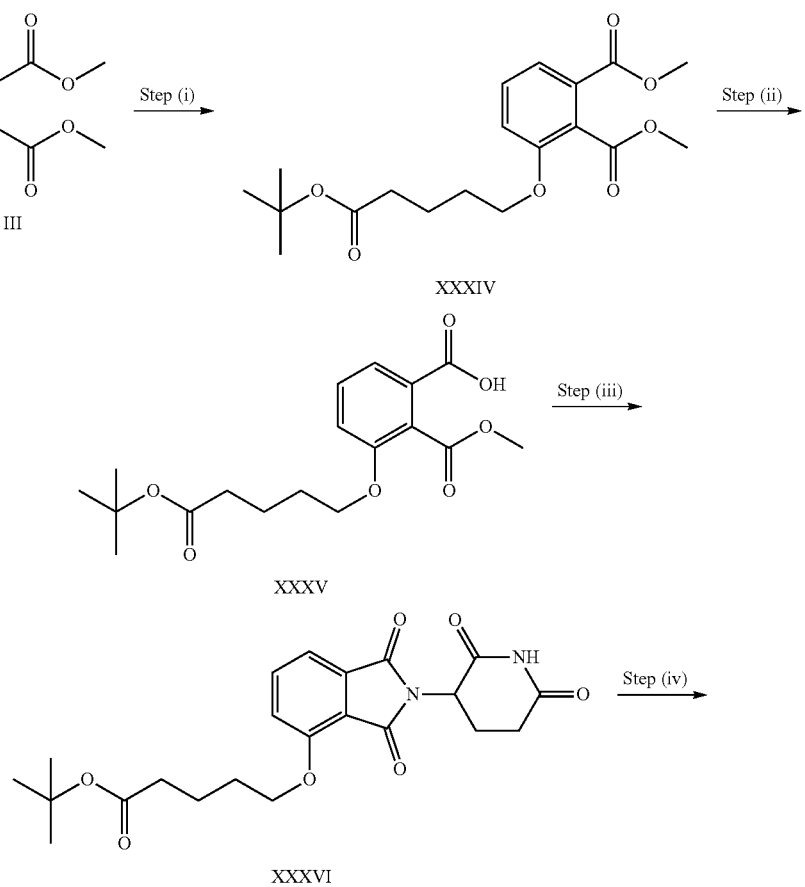

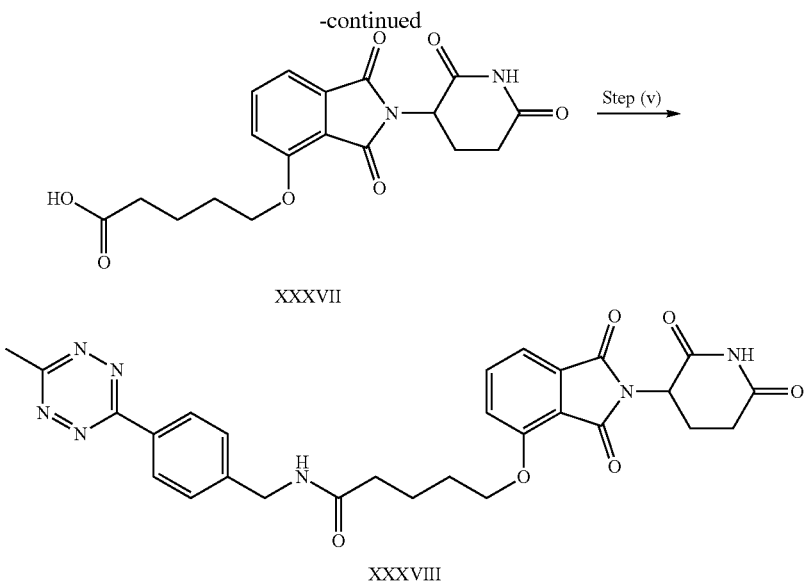

XXXVII

XXXVIII

Step (i) of Scheme 8 typically comprises stirring a compound of formula (III) with tert-butyl 5-bromopentanoate with a suitable base such as potassium carbonate in a suitable solvent such as N,N-dimethylformamide for a suitable period such as 18 hours. Such a process may be carried out at elevated temperature e.g. 50° C. An example procedure for step (i) is shown herein in Preparation 18.

Step (ii) of Scheme 8 typically comprises stirring a compound of formula (XXXIV) with a suitable base such as sodium hydroxide in a suitable solvent such as a mixture of tetrahydrofuran and methanol for a suitable period such as 2 hours. Such a process may be carried out at ambient temperature. An example procedure for step (ii) is shown herein in Preparation 19.

Step (iii) of Scheme 8 typically comprises stirring a compound of formula (XXXV) with 3-aminopiperidine-2,6-dione in a suitable solvent such as pyridine for a suitable period such as 17 hours. Such a process may be carried out at elevated temperature e.g. 110° C. An example procedure for step (iii) is shown herein in Preparation 20.

Step (iv) of Scheme 8 typically comprises stirring a compound of formula (XXXVI) with a suitable acid such as trifluoroacetic acid for a suitable period such as 3 hours. Such a process may be carried out at ambient temperature. An example procedure for step (iv) is shown herein in Preparation 20.

Step (v) of Scheme 8 typically comprises stirring a compound of formula (XXXVII) with [4-(6-methyl-1,2,4,5-tetrazin-3-yl)phenyl]methanamine, a suitable base such as N,N-diisopropylethylamine, and a coupling agent such as HATU in a suitable solvent such as N,N-dimethylformamide for a suitable period such as 1 hour. Such a process may be carried out at ambient temperature. An example procedure for step (v) is shown herein in Example 7.

Scheme 9

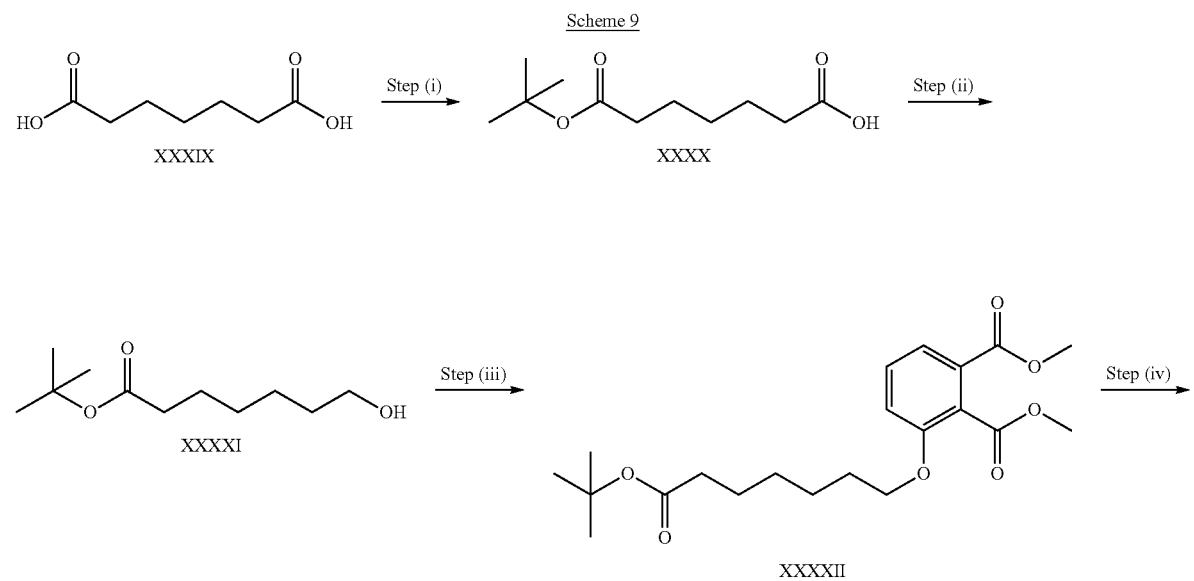

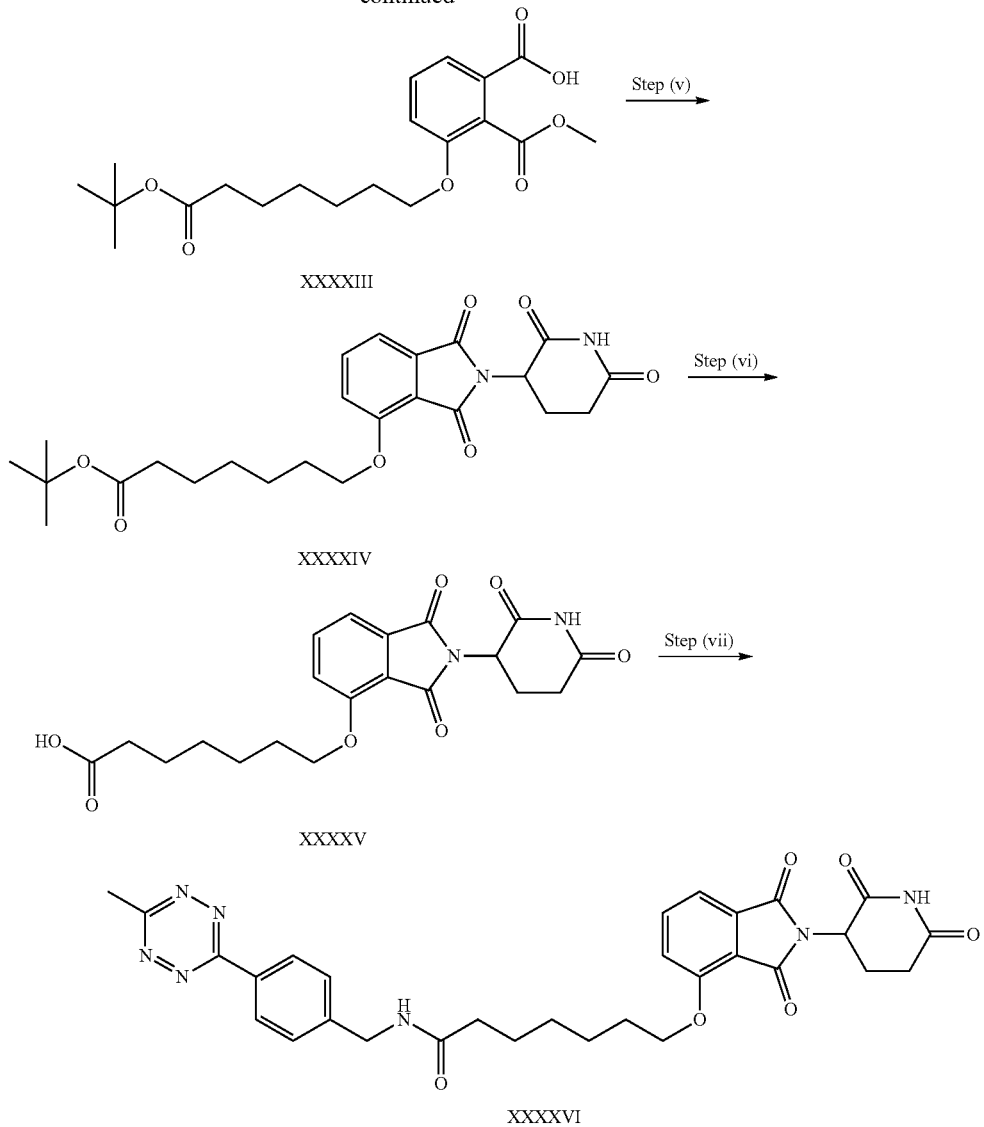

Step (i) of Scheme 9 typically comprises stirring a compound of formula (XXXIX) with 2-methyl-2-propanol, a catalyst such as DMAP and a coupling agent such as EDCl in a suitable solvent such as dichloromethane for a suitable period such as 18 hours. Such a process may be carried out at room temperature. An example procedure for step (i) is shown herein in Preparation 21.

Step (ii) of Scheme 9 typically comprises stirring a compound of formula (XXXX) with a reducing agent such as borane dimethyl sulfide in a suitable solvent such as tetrahydrofuran for a suitable period such as 24 hours. Such a process may be carried out at room temperature. An example procedure for step (ii) is shown herein in Preparation 22.

Step (iii) of Scheme 9 typically comprises stirring a compound of formula (XXXXI) with 1,2-dimethyl 3-hydroxybenzene-1,2-dicarboxylate in the presence of a phosphine ligand such as triphenylphosphine, and a compound of formula $R^1O(CO)N=N(CO)OR^1$, wherein $R^1$ is an alkyl group such as ethyl, isopropyl or butyl, in a suitable solvent such as tetrahydrofuran for a suitable period such as 18 hours. Such a process may be carried out at ambient temperature. An example procedure for step (iii) is shown herein in Preparation 23.

Step (iv) of Scheme 9 typically comprises stirring a compound of formula (XXXXII) with a suitable base such as sodium hydroxide in a suitable solvent such as a mixture of tetrahydrofuran and methanol for a suitable period such as 2 hours. Such a process may be carried out at ambient temperature. An example procedure for step (iv) is shown herein in Preparation 23.

Step (v) of Scheme 9 typically comprises stirring a compound of formula (XXXXIII) with 3-aminopiperidine-2,6-dione in a suitable solvent such as pyridine for a suitable period such as 17 hours. Such a process may be carried out at elevated temperature e.g. 110° C. An example procedure for step (v) is shown herein in Preparation 24.

Step (vi) of Scheme 9 typically comprises stirring a compound of formula (XXXXV) with a suitable acid such as trifluoroacetic acid for a suitable period such as 3 hours. Such a process may be carried out at ambient temperature. An example procedure for step (vi) is shown herein in Preparation 24.

Step (vii) of Scheme 9 typically comprises stirring a compound of formula (XXXXV) with [4-(6-methyl-1,2,4,5-tetrazin-3-yl)phenyl]methanamine, a suitable base such as N,N-diisopropylethylamine, and a coupling agent such as HATU in a suitable solvent such as N,N-dimethylformamide for a suitable period such as 1 hour. Such a process may be carried out at ambient temperature. An example procedure for step (vii) is shown herein in Example 8.

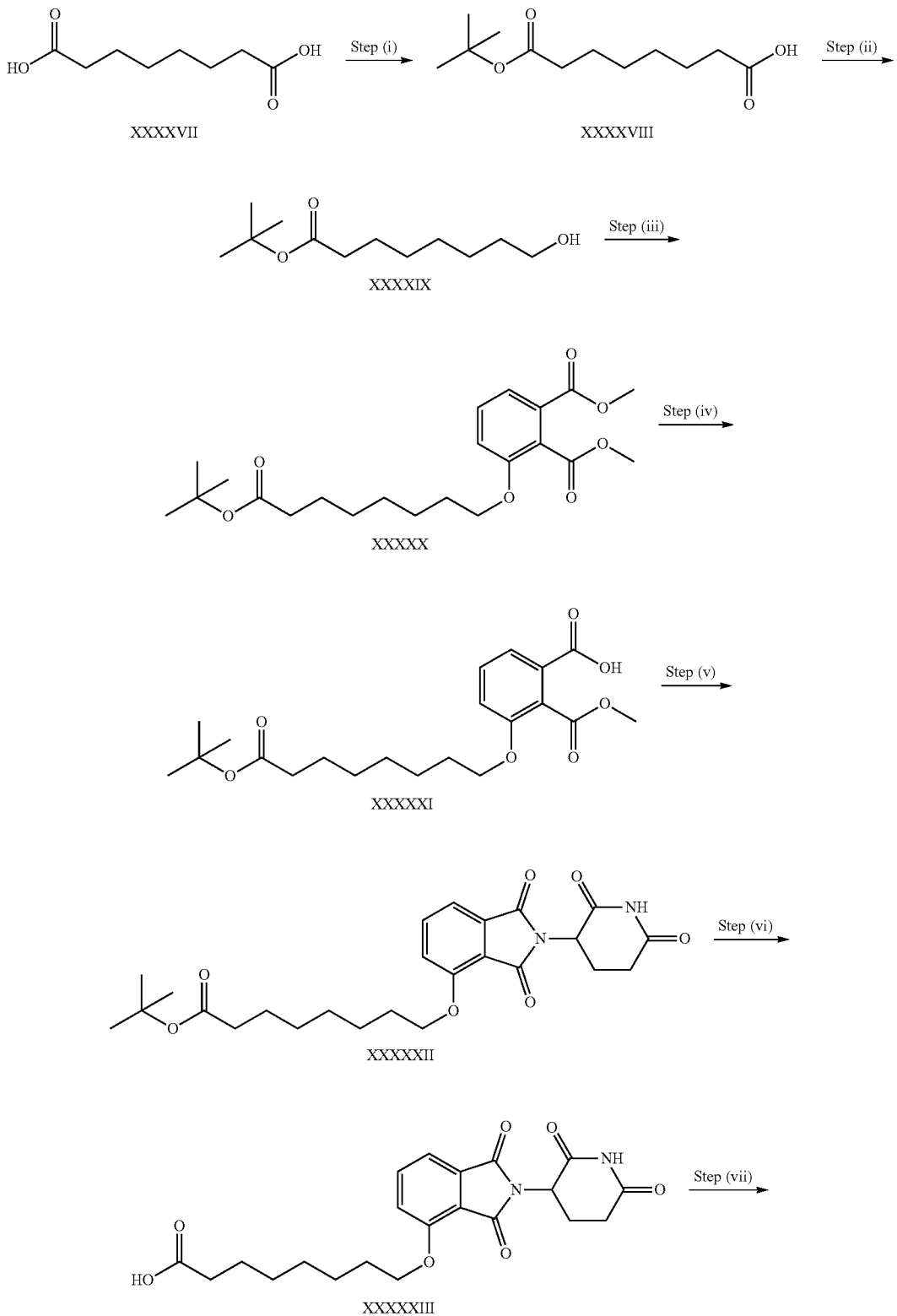

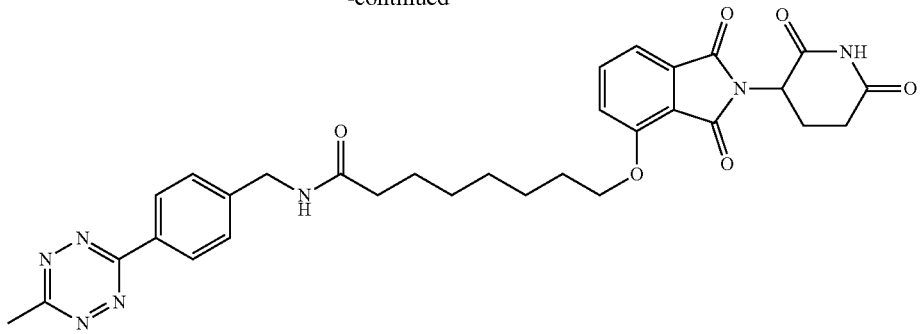

XXXXXIV

Step (i) of Scheme 10 typically comprises stirring a compound of formula (XXXXVII) with 2-methyl-2-propanol, a catalyst such as DMAP and a coupling agent such as EDCl in a suitable solvent such as dichloromethane for a suitable period such as 5 hours. Such a process may be carried out at room temperature. An example procedure for step (i) is shown herein in Preparation 25.

Step (ii) of Scheme 10 typically comprises stirring a compound of formula (XXXXVIII) with a reducing agent such as borane dimethyl sulfide in a suitable solvent such as tetrahydrofuran for a suitable period such as 24 hours. Such a process may be carried out at room temperature. An example procedure for step (ii) is shown herein in Preparation 26.

Step (iii) of Scheme 10 typically comprises stirring a compound of formula (XXXXIX) with 1,2-dimethyl 3-hydroxybenzene-1,2-dicarboxylate in the presence of a phosphine ligand such as triphenylphosphine, and a compound of formula $R^1O(CO)N=N(CO)OR^1$, wherein $R^1$ is an alkyl group such as ethyl, isopropyl or butyl, in a suitable solvent such as tetrahydrofuran for a suitable period such as 96 hours. Such a process may be carried out at ambient temperature. An example procedure for step (iii) is shown herein in Preparation 27.

Step (iv) of Scheme 10 typically comprises stirring a compound of formula (XXXXX) with a suitable base such as sodium hydroxide in a suitable solvent such as a mixture of tetrahydrofuran and methanol for a suitable period such as 2 hours. Such a process may be carried out at ambient temperature. An example procedure for step (iv) is shown herein in Preparation 27.

Step (v) of Scheme 10 typically comprises stirring a compound of formula (XXXXXI) with 3-aminopiperidine-2,6-dione in a suitable solvent such as pyridine for a suitable period such as 17 hours. Such a process may be carried out at elevated temperature e.g. 110° C. An example procedure for step (v) is shown herein in Preparation 27.

Step (vi) of Scheme 10 typically comprises stirring a compound of formula (XXXXII) with a suitable acid such as trifluoroacetic acid for a suitable period such as 3 hours. Such a process may be carried out at ambient temperature. An example procedure for step (vi) is shown herein in Preparation 27.

Step (vii) of Scheme 10 typically comprises stirring a compound of formula (XXXXVIII) with [4-(6-methyl-1,2,4,5-tetrazin-3-yl)phenyl]methanamine, a suitable base such as N,N-diisopropylethylamine, and a coupling agent such as HATU in a suitable solvent such as N,N-dimethylformamide for a suitable period such as 2 hours. Such a process may be carried out at ambient temperature. An example procedure for step (vii) is shown herein in Example 9.

Degradation by Self-Assembling CLIPTACs

Also described is the degradation of BRD4 and ERK1/2 using a TCO tagged JQ1 and a TCO tagged covalent ERK1/2 inhibitor, respectively. The potential of self-assembling CLIPTACs to overcome solubility and cell permeability problems of PROTACs was also studied.

As shown herein, the self-assembling CLIPTAC approach of the invention was successfully applied to the intracellular degradation of the two key oncology targets BRD4 and ERK1/2, demonstrating the potential of this approach as an alternative to pre-formed PROTACs. A series of negative control experiments validate the self-assembling CLIPTAC approach, including perturbation of the binding to CRBN using a methylated analogue of Tz-thalidomide, perturbation of binding to BRD4 using the inactive enantiomer of JQ1-TCO, and perturbation of the IEDDA cycloaddition. In addition, experiments performed in which cells were pretreated with the proteasome inhibitor carfilzomib confirm that the observed protein degradation occurs via proteasomal catabolism.

BRD4 Degradation Background

BRD4 is a member of the Bromo- and Extra-terminal (BET) family which is involved in transcriptional regulation. BRD4 recognizes acetylated lysine residues on chromatin via its two conserved N-terminal bromodomains (BD1 and BD2) and recruits transcriptional regulatory complexes (Shi et al. (2014) The Mechanisms behind the Therapeutic Activity of BET Bromodomain Inhibition. *Mol. Cell* 54: 728-736). The recent discovery of small molecule BET inhibitors such as JQ1 (Filippakopoulos et al. (2010) Selective inhibition of BET bromodomains. *Nature* 468: 1067-1073) and I-BET (Nicodeme et al. (2010) Suppression of inflammation by a synthetic histone mimic. *Nature* 468: 1119-1123) has enabled validation of BET inhibition as an effective therapeutic strategy for several hematologic malignancies (Dawson et al. (2011) Inhibition of BET recruitment to chromatin as an effective treatment for MLL-fusion leukaemia. *Nature* 478: 529-533; Delmore et al. BET Bromodomain Inhibition as a Therapeutic Strategy to Target c-Myc. *Cell* 146: 904-917; Zuber et al. (2011) RNAi screen identifies Brd4 as a therapeutic target in acute myeloid leukaemia. *Nature* 478: 524-528) and solid tumours (Lockwood et al. (2012) Sensitivity of human lung adenocarcinoma cell lines to targeted inhibition of BET epigenetic signaling proteins. *P. Natl. Acad. Sci.* 109: 19408-19413; Puissant et al. (2013) Targeting MYCN in Neuroblastoma by BET Bromodomain Inhibition. *Cancer Discov.* 3: 308-323), and as an anti-inflammatory approach (Nicodeme, et al.

(2010) Suppression of inflammation by a synthetic histone mimic. *Nature* 468: 1119-1123). Protein degradation provides an alternative approach to target the BET family. BRD4 degradation using PROTACs has been shown to be successful when recruiting either CRBN (Winter, et al. (2015) Phthalimide conjugation as a strategy for in vivo target protein degradation. *Science* 348: 1376-1381; Lu, et al. (2015) Hijacking the E3 Ubiquitin Ligase Cereblon to Efficiently Target BRD4. *Chem. Biol.* 22: 755-763) or VHL (Zengerle, et al. (2015) Selective Small Molecule Induced Degradation of the BET Bromodomain Protein BRD4. *ACS Chem. Biol.* 10: 1770-1777) ubiquitin ligases.

As explained above, non-peptidic VHL ligands have been identified which have improved physicochemical properties (Galdeano et al. (2014) Structure-Guided Design and Optimization of Small Molecules Targeting the Protein-Protein Interaction between the von Hippel-Lindau (VHL) E3 Ubiquitin Ligase and the Hypoxia Inducible Factor (HIF) Alpha Subunit with in Vitro Nanomolar Affinities. *J. Med. Chem.* 57: 8657-8663), while the phthalimide immunomodulatory drug thalidomide has been identified as a ligand of the E3 ubiquitin ligase cereblon (CRBN) (Ito et al. (2010) Identification of a Primary Target of Thalidomide Teratogenicity. *Science* 327: 1345-1350) and PROTACs targeting the efficient degradation of various intracellular target proteins, including BRD4 (Winter et al. (2015) Phthalimide conjugation as a strategy for in vivo target protein degradation. *Science* 348: 1376-1381; Lu et al. (2015) Hijacking the E3 Ubiquitin Ligase Cereblon to Efficiently Target BRD4. *Chem. Biol.* 22: 755-763; Zengerle et al. (2015) Selective Small Molecule Induced Degradation of the BET Bromodomain Protein BRD4. *ACS Chem. Biol.* 10: 1770-1777), BCR-ABL (Lai et al. (2016) Modular PROTAC Design for the Degradation of Oncogenic BCR-ABL. *Angew. Chem. Int. Ed.* 55: 807-810), ERRα and RIPK2 (Bondeson et al. (2015) Catalytic in vivo protein knockdown by small-molecule PROTACs. *Nat. Chem. Biol.* 11: 611-617) have been described.

BRD4 Degradation by Self-Assembling CLIPTACs

For the first time, the degradation of BRD4 was elicited using self-assembling CLIPTACs, a new technology based on the bioorthogonal reaction between Tz-thalidomide and a TCO-ligand.

Figure 2:
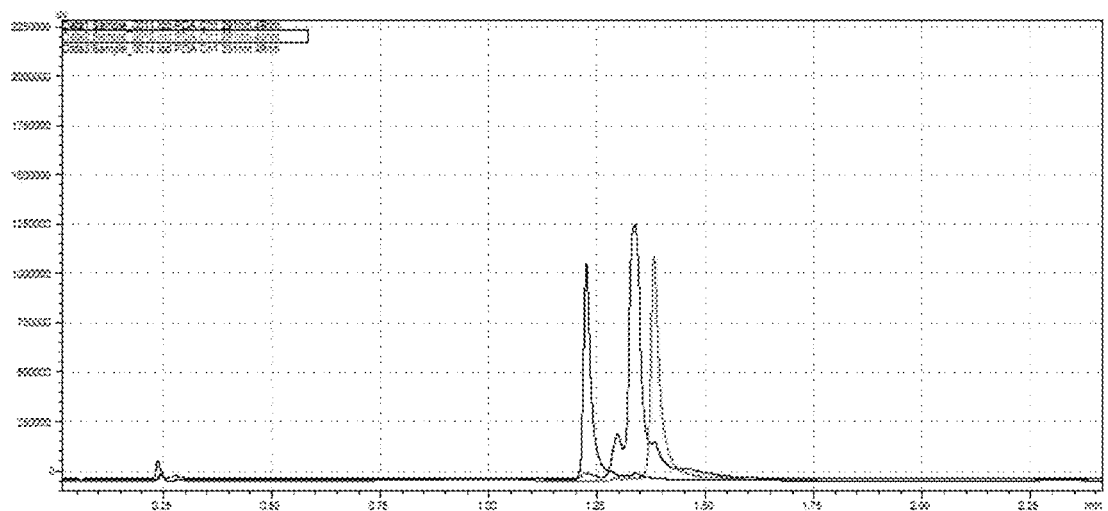

The bioorthogonal reaction between Tz-thalidomide and JQ1-TCO was investigated by LC-MS. By mixing the two reagents in a 1:1 ratio, the reaction was shown to be complete after 15 min in DMSO (FIG. 2).

The enzymatic activity of JQ1-TCO, JQ1-CLICK and (−)JQ1-TCO was evaluated against both domains of BRD4, BRD4-1 and BRD4-2. As expected from the design, the insertion of the TCO tag did not affect the binding affinity to BRD4 (FIG. 3a) as JQ1-TCO potency against BRD4 ($IC_{50}$ (BRD4-1)=0.016±0.003 µM and $IC_{50}$ (BRD4-2)= 0.063±0.002 µM) was found close to the activity exhibited by JQ1 ($IC_{50}$ (BRD4-1)=0.023 µM and $IC_{50}$ (BRD4-2)= 0.044 µM). Furthermore, when JQ1-TCO is clicked with Tz-thalidomide, the clicked complex (JQ1-CLICK) remains active against BRD4 ($IC_{50}$ (BRD4-1)=0.009±0.001 µM and $IC_{50}$ (BRD4-2)=0.019±0.001 µM, FIG. 3a).

These results support the use of JQ1-TCO as self-assembling CLIPTACs. In the same assay, (−)JQ1-TCO was found much less active against BRD4 ($IC_{50}$ (BRD4-1)=13.55±0.21 µM and $IC_{50}$ (BRD4-2)=24.25±0.92 µM) which validates its use as control compound (FIG. 3a).

Figure 3:
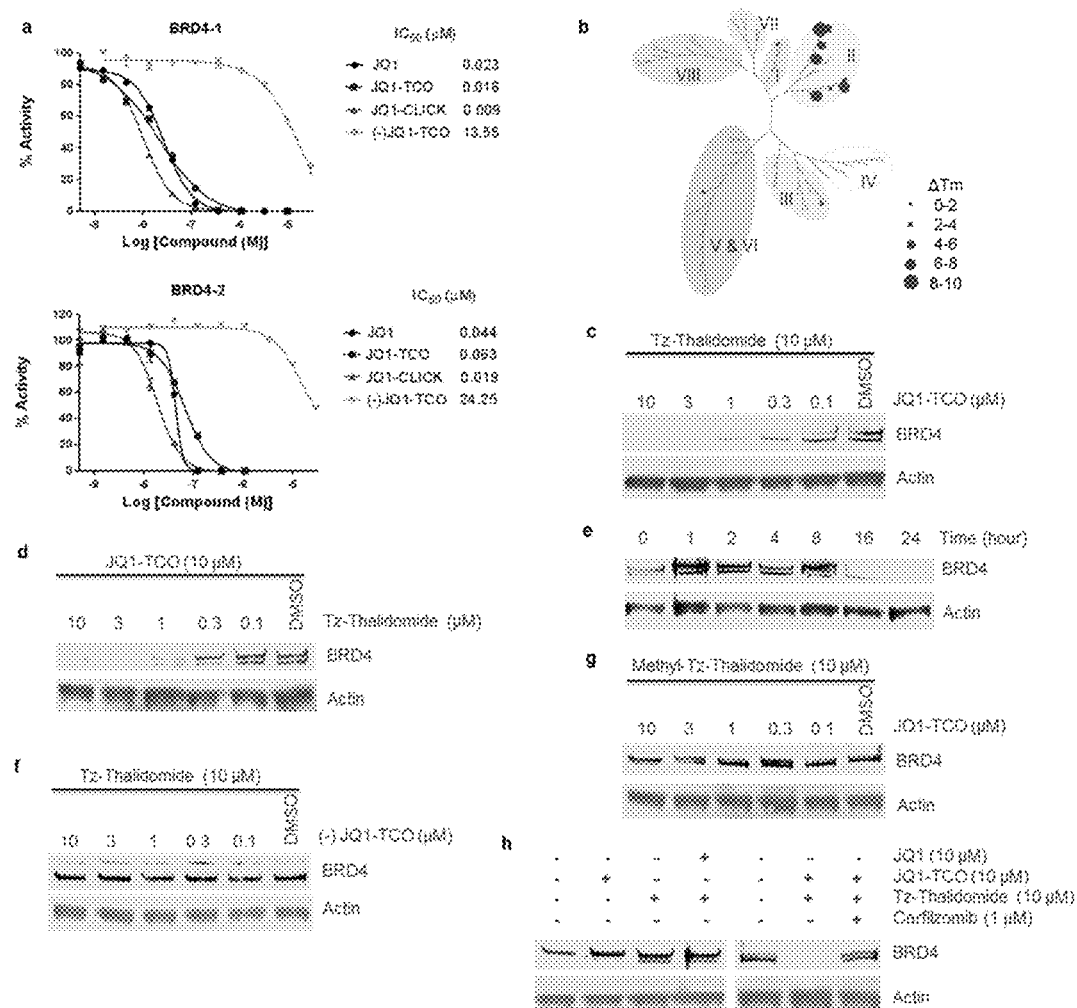
Figure 4:
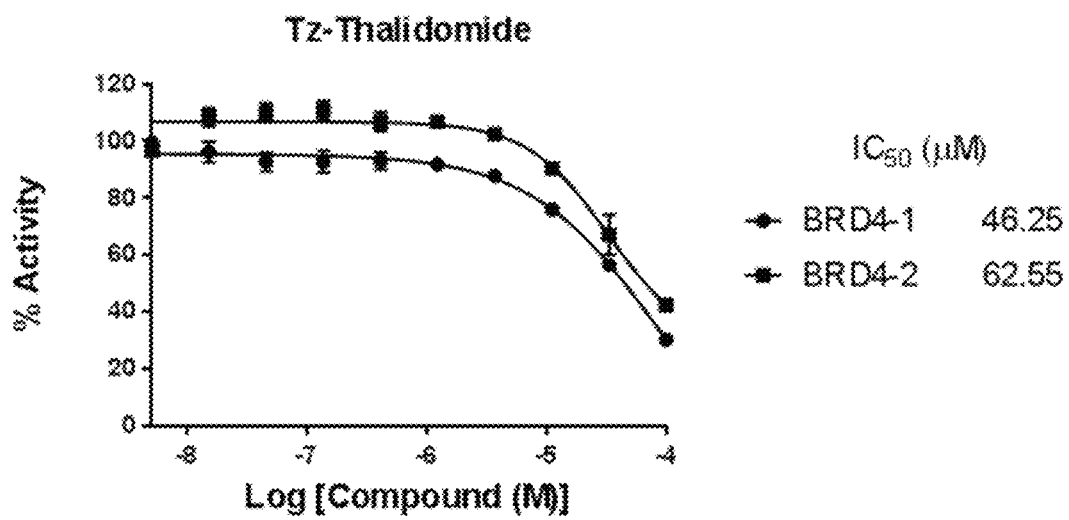

Tz-Thalidomide showed negligible activity against BRD4 ($IC_{50}$ (BRD4-1)=46.25±1.91 µM and $IC_{50}$ (BRD4-2)= 62.55±5.73 µM, FIG. 4), indicating that this CLIPTAC precursor is unlikely to significantly bind to BRD4 in cells. Finally, the selectivity profile of JQ1-TCO against the BET family was determined by thermal shift assay. As expected, JQ1-TCO was found to bind selectively to subfamily II demonstrating that the insertion of the TCO tag did not compromise the selectivity of the compound (FIG. 3b). (Liu et al. (2012) ChromoHub: a data hub for navigators of chromatin-mediated signalling. *Bioinformatics* 28: 2205-2206)

To elicit protein degradation using the self-assembling CLIPTACs, HeLa cells were first treated with JQ1-TCO for 18 hours followed by Tz-thalidomide for a further 18 hours. BRD4 presence was assessed by SDS-PAGE followed by Western Blot using a specific BRD4 antibody. At a fixed concentration of Tz-thalidomide, JQ1-TCO elicited concentration dependent degradation of BRD4, with complete degradation at 10 and 3 µM and partial degradation at 1 and 0.3 µM (FIG. 3c). Quantitation of the band intensities allowed calculation of a 50% degradation concentration ($DC_{50}$) of 420 nM, similar to the published value for dBET (Winter, et al. (2015) Phthalimide conjugation as a strategy for in vivo target protein degradation. *Science* 348: 1376-1381). Alternatively, at a fixed concentration of JQ1-TCO (10 µM), Tz-thalidomide showed a concentration dependent degradation of BRD4, which was completely degraded at high concentrations of Tz-thalidomide (10 and 3 µM) and partially at lower concentrations (FIG. 3d). These two experiments demonstrate that BRD4 degradation is dependent on the concentrations of both self-assembling CLIPTAC precursors (JQ1-TCO and Tz-thalidomide).

To determine the time required for BRD4 degradation with the self-assembling CLIPTACs approach, a time-course experiment was performed in which HeLa cells were treated with JQ1-TCO (10 µM) followed by Tz-thalidomide (10 µM) for the indicated time (FIG. 3e). The immunodetection signal indicated unchanged BRD4 levels up to 8 hours following the addition of Tz-thalidomide. After 16 hours, BRD4 was still detected but the abundance of protein had clearly dropped compared to untreated cells. After 24 hours, BRD4 had disappeared indicating complete degradation. This time course experiment shows that the effect of self-assembling CLIPTACs on BRD4 level is visible after 16 hours.

To confirm that degradation of BRD4 occurs according to the proposed mechanism, experiments were performed in which the interaction with BRD4 or CRBN was perturbed. Interfering with the self-assembling CLIPTACs binding to BRD4 or to CRBN would prevent the spatial proximity between the two proteins, essential for ubiquitination, and therefore, should block protein degradation. HeLa cells were treated with (−)JQ1-TCO followed by Tz-thalidomide (10 µM). No BRD4 degradation was observed at any of the concentrations of (−) JQ1-TCO tested (FIG. 3f), confirming that binding of the CLIPTAC to BRD4 is required for protein degradation. The HeLa cells were then treated with JQ1-TCO (10 µM) followed by methyl-Tz-thalidomide (10 µM). The level of BRD4 remained unchanged across the experiment (FIG. 3g) confirming that interfering with the binding to CRBN blocks BRD4 degradation. These two findings, confirm that degradation of BRD4 is dependent on the self-assembling CLIPTAC binding to both BRD4 and CRBN which in order to promote spatial proximity between the two proteins.

Additional control experiments show that the level of BRD4 was unaffected by either JQ1-TCO or Tz-thalidomide alone (FIG. 3h). Further, treatment of the HeLa cells with untagged JQ1 (10 µM) followed by Tz-thalidomide (10 µM)

(FIG. 3h) did not significantly change BRD4 levels as compared with untreated cells. In this experiment JQ1 binds to BRD4 but is unable to 'click' with Tz-thalidomide, preventing spatial proximity between BRD4 and CRBN, confirming the importance of the bioorthogonal reaction in the self-assembling CLIPTAC technology. In a final control experiment a protease inhibitor, Carfilzomib, was used. Under these conditions, the level of BRD4 remained the same as in untreated cells (FIG. 3h), confirming that the degradation of BRD4 by CLIPTAC proceeds via proteasomal action.

ERK1/2 Degradation by Self-Assembling CLIPTACs

To validate the broader application of the self-assembling CLIPTAC method, the degradation of an additional target from a different protein family was investigated. ERK1/2 are serine/threonine kinases and are part of the RAS/RAF/MEK/ERK cascade which is implicated in several biological processes (Roskoski Jr (2012) ERK1/2 MAP kinases: Structure, function, and regulation. *Pharmacol. Res.* 66: 105-143). This signalling pathway has been highly targeted in cancer research (Samatar et al. (2014) Targeting RAS-ERK signalling in cancer: promises and challenges. *Nat. Rev. Drug Discov.* 13: 928-942) as exemplified by the number of ERK1/2 inhibitors developed (Deng et al. (2014) Discovery of Novel, Dual Mechanism ERK Inhibitors by Affinity Selection Screening of an Inactive Kinase. *J. Med. Chem.* 57: 8817-8826; Bagdanoff et al. (2015) Tetrahydropyrrolodiazepenones as inhibitors of ERK2 kinase. *Bioorg. Med. Chem. Lett.* 25: 3788-3792; Ren et al. (2015) Discovery of Highly Potent, Selective, and Efficacious Small Molecule Inhibitors of ERK1/2. *J. Med. Chem.* 58: 1976-1991; Ward et al. (2015) Structure-Guided Design of Highly Selective and Potent Covalent Inhibitors of ERK1/2. *J. Med. Chem.* 58: 4790-4801). ERK1/2 degradation, on the other hand, has never been exploited as a potential therapeutic strategy and could represent an alternative to protein inhibition for targeting the RAS/RAF/MEK/ERK cascade in cancer.

The covalent ERK1/2 TCO-inhibitor Probe 1 (FIG. 5a) shows submicromolar activity in A375 cells ($GI_{50}$=0.47±0.14 µM) and was used to study the degradation of ERK1/2 by self-assembling CLIPTAC. First, the bioorthogonal reaction between Probe 1 and Tz-thalidomide was investigated by LC-MS and found to be complete after 15 min (FIG. 6).

Figure 7:
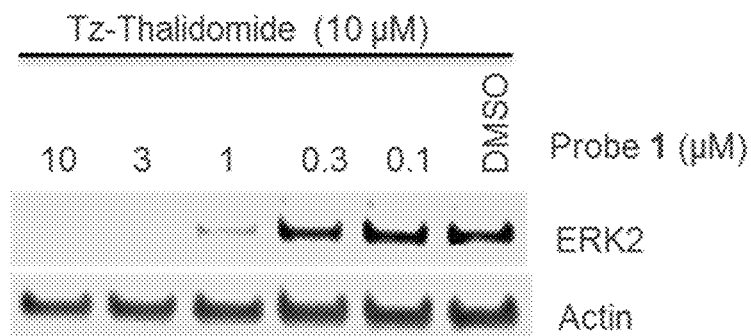
Figure 10:
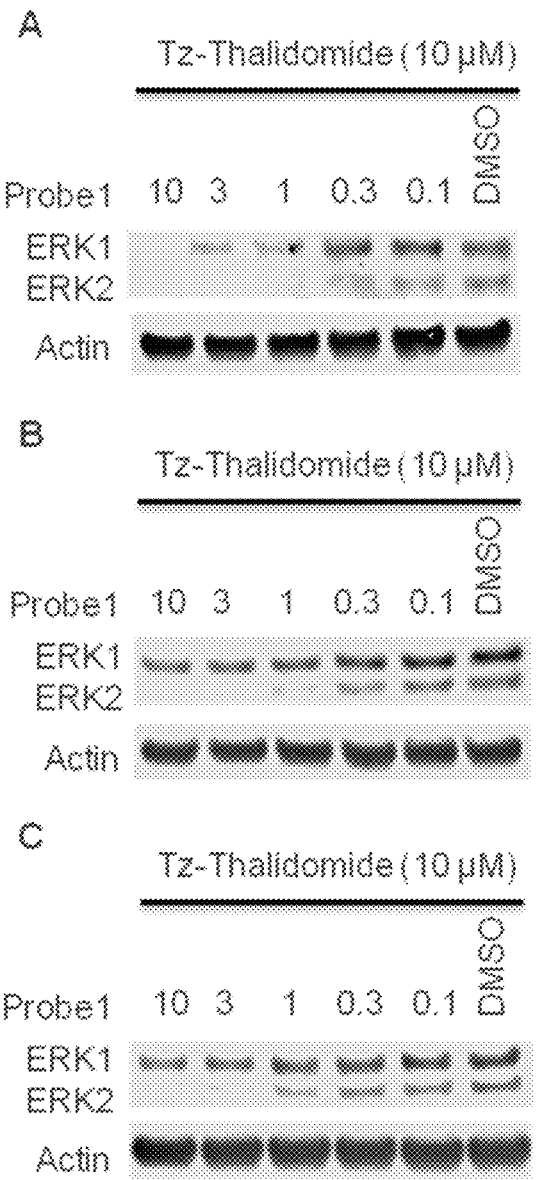

To explore the potential of the self-assembling CLIPTAC methodology to recruit CRBN and degrade ERK1 and 2 in cell lines where the RAS/RAF/MEK/ERK cascade is upregulated, A375 cells, a $BRAF^{V600E}$ mutant melanoma cell line, were treated with Probe 1 for 18 hours followed by Tz-thalidomide (10 µM) for a further 18 hours. ERK1 and 2 levels were assessed by SDS-PAGE followed by Western Blot using a total ERK1/2 antibody. The immunodetection signal revealed that ERK1/2 abundance was dependent on Probe 1 concentration (FIG. 5b). At low concentration (0.1 µM), the level of ERK1/2 was unchanged. Partial degradation was observed at 0.3 and 1 µM and at higher concentrations ERK1/2 suppression appeared complete. Quantitation of the signal intensities allowed calculation of a DC50 of 490 nM. A similar degradation profile was obtained when the cells were pre-treated with Probe 1 for a shorter period of 8 or 4 hours followed by treatment with Tz-thalidomide (FIG. 10). This experiment was also performed in HCT116 cells, a KRAS mutant colorectal cell line, and complete degradation of ERK2 was also observed at high concentrations of Probe 1 (FIG. 7).

Figure 11:
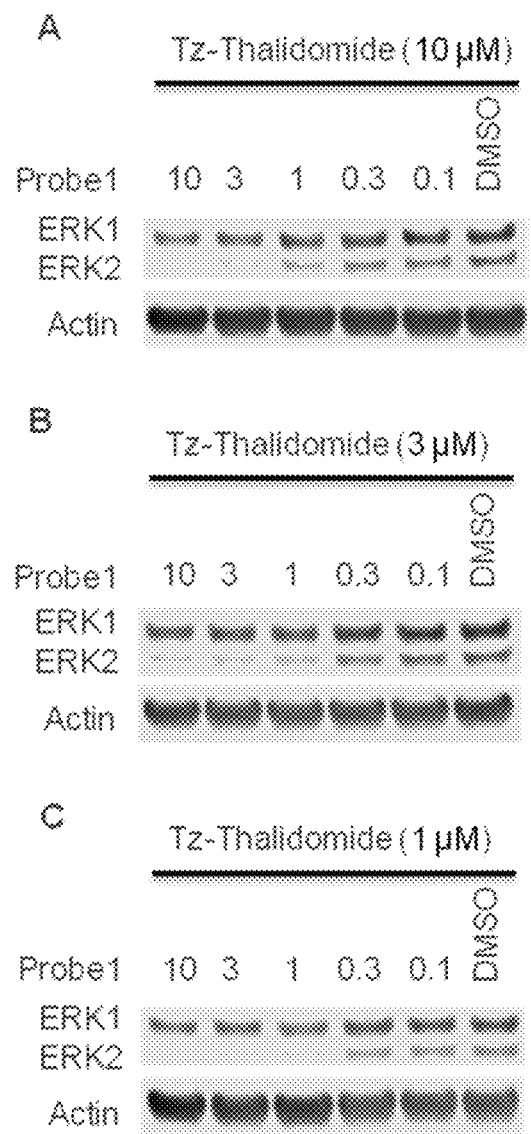

Degradation was retained with lower concentrations of Tz-thalidomide, and treating A375 cells with 1 µM Probe 1 for 4 hours followed by Tz-thalidomide (1 µM) for 18 hours led to the best degradation profile. At lower concentrations of Tz-thalidomide (0.1 and 0.3 µM), ERK1/2 degradation was not observed (FIG. 11).

ERK1/2 degradation was then studied in a time-course experiment in which A375 cells were treated with Probe 1 (10 µM) followed by Tz-thalidomide (10 µM) for the indicated time. From the immunodetection signal, ERK1/2 degradation is observed partially after 8 hours and is complete after 16 hours (FIG. 5c).

Figure 12:
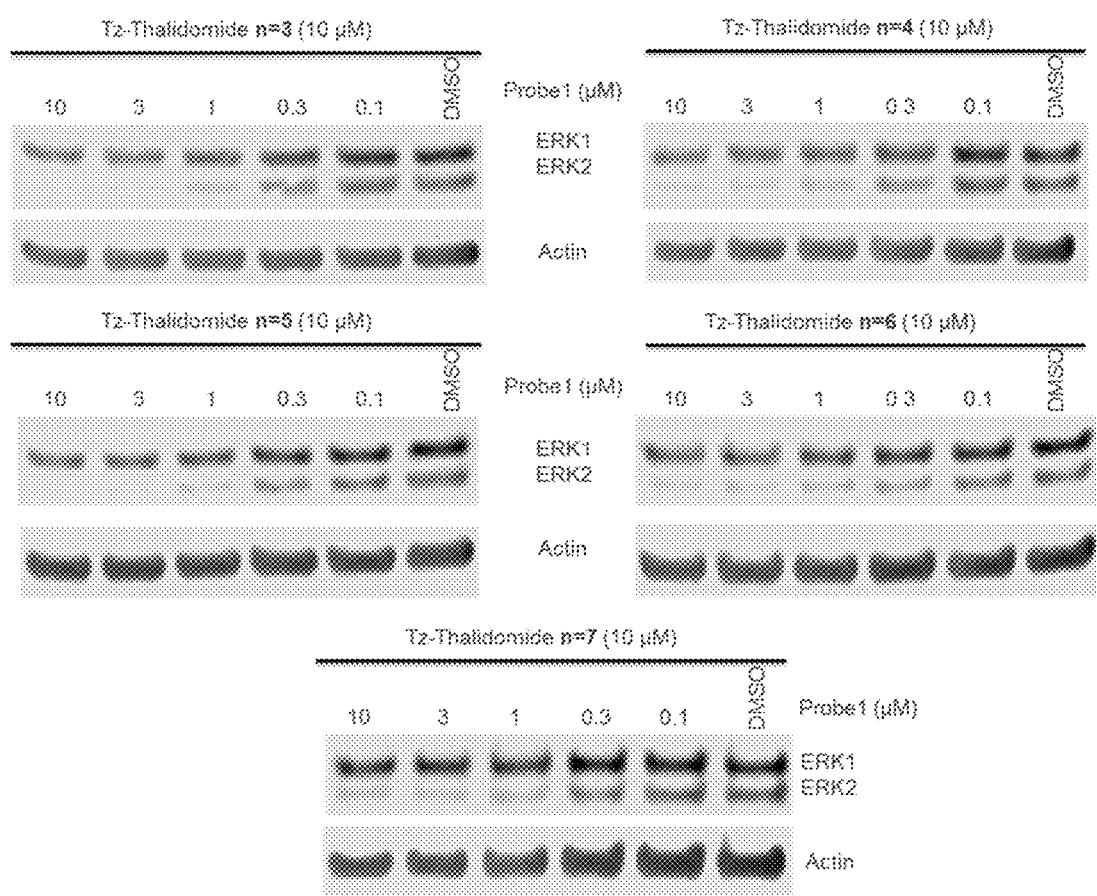

The influence of the linker length between the tetrazine group and the thalidomide moiety of the Tz-thalidomide reagent on ERK1/2 degradation was investigated. Four reagents were synthesised with the linker being 3, 4, 6 or 7 carbons. A375 cells were treated with Probe 1 for 8 hours followed by the indicated Tz-thalidomide (10 µM) for 18 hours. From the Western Blot analysis, the best degradation profile was obtained for n=3 and 5 (FIG. 12).

Figure 8:
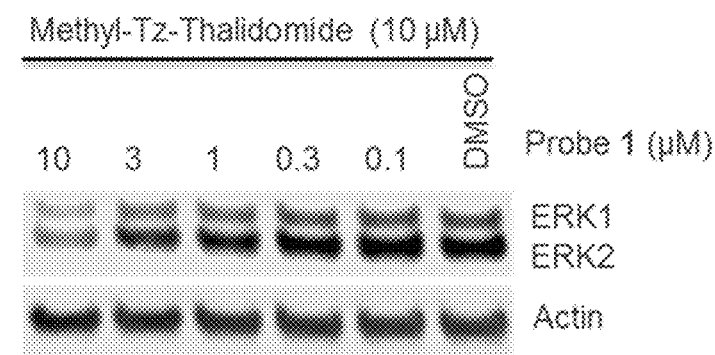

To confirm that degradation of ERK1/2 occurs according to the proposed mechanism, experiments were performed in which the interaction with CRBN was perturbed. A375 cells were treated with Probe 1 followed by methyl-Tz-thalidomide (10 µM), which binds less avidly to CRBN than Tz-thalidomide. The immunodetection level revealed downregulation of ERK1/2 in a concentration-dependent manner (FIG. 5d). However, ERK1/2 degradation was found far less effective with methyl-Tz-thalidomide than with Tz-thalidomide. The same experiment was carried out in HCT116 cells and the same ERK1/2 downregulation was observed (FIG. 8). These experiments suggest that inserting a methyl group on the diacetamide moiety of thalidomide affects the binding affinity to CRBN but does not abolish the interaction between thalidomide and CRBN. From these results, binding to CRBN appears crucial to induce spatial proximity and therefore degradation.

Finally, it was shown that the level of ERK1/2 was unmodified when A375 cells were treated with Probe 1 or Tz-thalidomide alone (FIG. 5e). When the bioorthogonal reaction between Tz-thalidomide and the TCO ligand was suppressed using the untagged covalent ERK1/2 inhibitor, no protein degradation was observed (FIG. 5e). It was also demonstrated that ERK1/2 degradation was rescued when Carfilzomib was added in the experiment (FIG. 5e), confirming that proteasomal action is required to elicit the degradation of ERK1/2 by CLIPTAC.

The Benefits of Self-Assembling CLIPTACs

Figure 9:
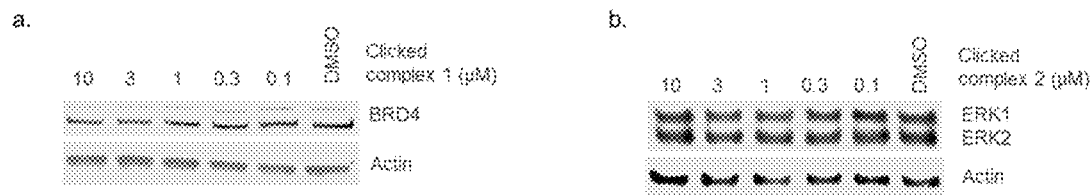

To confirm that the observed protein degradation arises from in-cell click formation of the heterobifunctional molecule, we performed analogous experiments in which the CLIPTAC was pre-formed by reaction of the two click partners prior to addition to cells. We mixed Tz-thalidomide and JQ1-TCO or Probe 1 in a 1:1 ratio to form the clicked complex 1 (JQ1-CLICK) or 2, respectively. HeLa and A375 cells were treated with clicked complex 1 or 2, respectively, for 18 hours (FIG. 9). The immunodetection signal was identical across the experiments indicating no degradation of BRD4 or ERK1/2 respectively. These results are consistent with a lack of cell permeability of the clicked heterobifunctional PROTAC, and confirm that the observed protein degradation results from click formation of the PROTAC from the two CLIPTAC partner molecules subsequent to their entry into cells.

PROTACs offer important advantages over small molecule inhibition of therapeutic targets. While small molecule inhibitors act via target occupancy, PROTACs offer a long lasting effect by eliminating the target until re-synthesis, which can take hours or days. Moreover, by triggering the degradation of the protein target, all functional sites are removed, abolishing all target protein functions. Such 'knockdown' is not feasible with small molecule inhibitor drugs, which typically interact with only one site on the target, leaving the others to function normally. In addition, developing small molecule inhibitor drugs is challenging: many intracellular target proteins of great clinical importance are currently classed as "poorly druggable". PROTACs are expected to be particularly useful in such circumstances, since the target protein ligand does not need to be a functional inhibitor. However, the need for PROTACs to enter cells in order to elicit protein degradation means that their physicochemical properties are of paramount importance.

Of the reported PROTACs eliciting the degradation of BRD4 described above, two (dBET1 and ARV-825) contain the BRD4 ligand JQ1 and the ligase recruiter thalidomide. These PROTACs differ only in the nature and length of their linker, which affects the efficiency of BRD4 degradation. The third, MZ1, uses VHL-1 as the ligase recruiter and JQ1 as the BRD4 ligand. Targeted BRD4 proteolytic knockdown has therefore emerged as a useful model system for PROTAC development and validation. These PROTACs show molecular weights in a significantly higher range than Lipinski guidelines—for example the three recently published BRD4-targeting PROTACs range from 785-1002 (Table 1).

In addition, these molecules possess a high polar surface area (PSA) that is normally associated with poor cellular penetration (range 194-211). However, as heterobifunctional molecules, even the more recently described 'drug-like' PROTACs possess a relatively high molecular weight, which can limit cellular permeation and solubility, and compromise bioavailability and pharmacokinetics (Deshaies (2015) Protein degradation: Prime time for PROTACs. Nat. Chem. Biol. 11: 634-635).

A comparison of physicochemical properties of the published BRD4 PROTACs with the CLIPTACs described herein indicates that MW and PSA have indeed been significantly reduced (Table 1). The successful degradation of BRD4 and ERK1/2 in three different cell lines and the accompanying control experiments confirm that PROTACs can be formed in cells from the click reaction between Tz-thalidomide and TCO-ligand, and that the observed degradation occurs through proteasomal action following the binding of the PROTAC to CRBN and the protein of interest.

prophylaxis involving the administration of the compounds as described herein as well as pharmaceutical compositions comprising the compounds as described herein.

The CLIPTAC and CLIPTAC precursors of the invention find particular application in the treatment of a wide range of diseases where protein knockdown is indicated. Such diseases include proteostatic diseases (as herein defined) and diseases arising from undesired intracellular protein activity (for example, in the treatment of cancer, where the target protein may be an oncoprotein).

Thus, the invention may find application in the treatment of diseases selected from connective tissue disorders (for example, achondrogenesis type II, lysyl-hydroxylase deficiency), dwarfism (for example, kniest dysplasia, achondroplasia, thanatophoric dyslplasia, spondyloepimetaphyseal dysplasia (Strudwick type), spondyloepimetaphyseal dysplasia (congenital type), Nance-Insley syndrome), congenital disorders (for example, Gunther disease (congenital erythropoietic porphyria (CEP)), Noonan syndrome, apert syndrome, congenital heart disease, Cayler cardiofacial syndrome (BAVD) (asymmetric crying facies (ACF)), Weissenbacher-Zweymüller syndrome (WZS), congenital hyperthyroidism, conotruncal anomaly face syndrome (CTAF), osteogenesis imperfecta (brittle bone disease), congenital absence of the vas deferens (CAVD), Treacher Collins syndrome (TCS), acrocephaly (oxycephaly), broad thumb-hallux syndrome (Rubinstein-Taybi Syndrome), congenital methemoglobinemia, Benjamin syndrome), genetic or chromosomal disorders (for example, Gaucher disease type 2, aceruloplasminemia, angiokeratoma corporis diffusum, incontinentia pigmenti (Bloch-Sulzberger disease), hypochondroplasia, familial dysautonomia (FD) (Riley-Day syndrome), Wolf-Hirschhorn syndrome (Pitt syndrome), Smith-Lemli-Opitz syndrome, Alström syndrome, Stickler syndrome, fragile X syndrome, Osler-Weber-Rendu syndrome (hereditary hemorrhagic telangiectasia), hereditary spastic paraplegias, muscular dystrophy (Duchenne and Becker types), autosomal recessive familial amyotrophic lateral sclerosis (RFALS), adrenogenital syndrome, adrenoleukodystrophy (ALD), Sandhoff Disease, campomelic dysplasia (CMD), Lesch-Nyhan syndrome, Hutchinson-Gilford progeria syndrome (progeria), infantile-onset ascending hereditary spastic paralysis, severe achondroplasia with developmental delay and acanthosis nigricans (SADDAN), xeroderma pigmentosum, Joubert syndrome, Cowden syndrome (Multiple hamartoma syndrome), Birt-Hogg-Dubé syndrome (BHD), Bloom syndrome, Wilson's disease, Cof-

TABLE 1

Properties of the published PROTACs targeting BRD4 for degradation versus the self-assembling CLIPTAC precursors of the invention

|  |  | dBET1 | ARV-825 | MZ1 | Tz-thalidomide | JQ1-TCO | Probe 1 |
|---|---|---|---|---|---|---|---|
| MW |  | 785.34 | 923.52 | 1002.75 | 571.65 | 609.25 | 586.15 |
| ClogP |  | 2.486 | 4.755 | 4.899 | 1.195 | 5.86 | 6.52 |
| PSA |  | 194.05 | 204.67 | 211.49 | 173.44 | 110.5 | 130.16 |
| $IC_{50}$ | BRD4-1 | 0.020 | 0.090 | 0.38 | 46.25 | 0.016 |  |
| (µM) | BRD4-2 |  | 0.028 | 0.12 | 62.55 | 0.063 |  |

Target Proteins and Associated Medical Uses

The CLIPTAC and CLIPTAC precursors of the invention find application in the treatment of a wide range of diseases. Thus, the invention contemplates the compounds as described herein for use in medicine (e.g. for use in treatment or prophylaxis), methods of medical treatment or fin-Lowry syndrome, Jackson-Weiss syndrome, alpha-1-antitrypsin deficiency, androgen insensitivity syndrome (AIS), Factor V Leiden Thrombophilia, micro syndrome (Warburg-Sjo-Fledelius syndrome), McCune-Albright syndrome, polycystic kidney disease, Pseudoxanthoma elasticum (Grönblad-Strandberg syndrome), cystic fibrosis, Otospondylomegaepiphyseal dysplasia (OSMED), Beare-Stevenson cutis gyrate syndrome, X-linked severe combined immunodeficiency (X-SCID), Bonnevie-Ullrich syndrome (Turners syndrome), Anderson-Fabry disease, Cri du Chat Syndrome (Lejeune's Syndrome), Down's Syndrome (Trisomy 21), Klinefelter syndrome, Von Hippel-Lindau disease, Cockayne syndrome (CS) (Neill-Dingwall Syndrome), Triple X syndrome (Trisomy X), Roussy-Lévy syndrome, Peutz-Jeghers syndrome, chondrodystrophy syndrome, Familial Mediterranean Fever (FMF), Insley-Astley syndrome, Muenke syndrome (FGFR3-related craniosynostosis), Lynch syndrome (hereditary nonpolyposis colorectal cancer (HNPCC)), Marfan syndrome, Neurofibromatosis (NF) (types 1, 2 and Schwannomatosis), Hemochromatosis (Bronze Diabetes/Bronzed Cirrhosis), Waardenburg syndrome, Noack syndrome (Pfeiffer syndrome), Mowat-Wilson syndrome, Ehlers-Danlos syndrome, Usher syndrome (Hallgren syndrome), Li-Fraumeni syndrome (SBLA), Prader-Willi syndrome, Crouzon Syndrome (craniofacial dysarthtosis), Bourneville Disease (tuberous sclerosis), fibrocystic disease of the pancreas, Shprintzen-Goldberg syndrome, familial adenomatous polyposis (FAP), chronic granulomatous disease (CGD), Hyperandrogenism, Menkes Disease (MNK), Adenomatous Polyposis coli (APC)), metabolic disorders (for example, galactosemia, adenylosuccinate lyase deficiency, sphingolipidosis, porphyria cutanea tarda (PCT), Niemann-Pick disease, alkaptonuria, alkaptonuroc ochronosis, variegate porphyria (South African genetic porphyria), erythropoietic protoporphyria, erythropoietic porphyria, tetrahydrobiopterin deficiency (THBD) (BH4D), acute intermittent porphyria, aminolevulinic acid dehydratase deficiency porphyria (ALA dehydratase deficiency), ALAD Deficiency Porphyria (ADP), hyperoxaluria, primary hyperoxaluria, propionic academia, Burger-Grutz syndrome, Tay-Sachs disease, hepatoerythropoietic porphyria (HEP)), neurological, neurodegenerative diseases and central nervous system disorders (for example, Parkinson's disease, Alzheimer's disease, myotonic dystrophy (type 1 and type 2), dyskinesias, prion disease, schizophrenia, bipolar disorder, Krabbe disease (globoid cell leukodystrophy), Dejerome-Sottas disease, lacunar dementia, vascular dementia, Machado-Joseph disease (MJD), Huntington's disease, Alexander disease, progressive chorea, muscular atrophy, progressive muscular atrophy (PMA), bulbospinal muscular atrophy (Kennedy's disease), Friedreich's ataxia, spinal muscular atrophy, distal spinal muscular atrophy, canavan disease, primary senile degenerative dementia, hereditary neuropathy with liability to pressure palsy (HNPP) (tomaculous neuropathy), Creutzfeldt-Jakob disease, spinocerebellar ataxia, ataxia telangiectasia (Louis-Bar syndrome), amyotrophic lateral sclerosis (ALS), stroke, Rett syndrome, De Grouchy syndrome, motor neuron disease, ADHD, autism and major depressive disorder (MDD)), diseases of the lung (for example, emphysema), dental diseases (for example, amelogenesis imperfecta), diseases or disorders of the blood (for example, haemochromatosis, anemia, beta thalassemia (Cooley's anemia), haemophilia, sickle-cell anaemia, hypochromic anemia, hereditary coproporphyria (HCP), X-linked sideroblastic anemia, methemoglobinemia, primary pulmonary hypertension (PPH), pulmonary arterial hypertension (PAH), ischemia, acute and chronic CNS injury ischemia), eye diseases (for example, angiomatosis retinae, retinoblastoma (Rb), retinal degeneration), heart diseases (for example, cardiomyopathy, myocardial infarction), liver diseases (for example, neonatal hemochromatosis), inflammatory disorders (for example, hepatitis, inflammatory bowel disease (IBD), ulcerative colitis and gastritis), autoimmune diseases (for example, multiple sclerosis (MS), and type I diabetes), kidney diseases (for example, autosomal dominant polycystic kidney disease (ADPKD)), lung diseases, movement disorders, skin pigmentation disorders, speech and communication disorders, and thyroid diseases.

The invention may also find application in the treatment of conditions or diseases selected from inflammation, hepatitis, ulcerative colitis, gastritis, autoimmunity, inflammation, restenosis, stroke, heart failure, neurodegenerative conditions such as Alzheimers' disease, Parkinson's disease, Huntington's disease, myotonic dystrophy, and amyotrophic lateral sclerosis, AIDS, ischemia such as traumatic brain injury, spinal cord injury, cerebral ischemia, cerebral ischemia/reperfusion (I/R) injury, acute and chronic CNS injury ischemia, stroke or myocardial infarction, degenerative diseases of the musculoskeletal system such as osteoporosis, autoimmune diseases such as multiple sclerosis (MS) and Type I diabetes, and eye diseases such as retinal degeneration which result from loss of control of programmed cell death.

Cancers which can be treated by the CLIPTAC and CLIPTAC precursors of the invention may be selected from primary tumours (i.e. cancer cells at the originating site), local invasion (cancer cells which penetrate and infiltrate surrounding normal tissues in the local area), and metastatic (or secondary) tumours ie. tumours that have formed from malignant cells which have circulated through the bloodstream (haematogenous spread) or via lymphatics or across body cavities (trans-coelomic) to other sites and tissues in the body. Examples of cancers (and their benign counterparts) which may be treated (or inhibited) include, but are not limited to tumours of epithelial origin (adenomas and carcinomas of various types including adenocarcinomas, squamous carcinomas, transitional cell carcinomas and other carcinomas) such as carcinomas of the bladder and urinary tract, breast, gastrointestinal tract (including the esophagus, stomach (gastric), small intestine, bowel, colon, rectum and anus), liver (hepatocellular carcinoma), gall bladder and biliary system, exocrine pancreas, kidney (renal cell carcinoma), lung (for example adenocarcinomas, small cell lung carcinomas, non-small cell lung carcinomas, bronchioalveolar carcinomas and mesotheliomas), head and neck (for example cancers of the tongue, buccal cavity, larynx, pharynx, nasopharynx, tonsil, salivary glands, nasal cavity and paranasal sinuses), ovary, fallopian tubes, peritoneum, vagina, vulva, penis, cervix, myometrium, endometrium, thyroid (for example thyroid follicular carcinoma), adrenal, prostate, skin and adnexae (for example melanoma, basal cell carcinoma, squamous cell carcinoma, keratoacanthoma, dysplastic naevus); haematological malignancies (i.e. leukemias, lymphomas) and premalignant haematological disorders and disorders of borderline malignancy including haematological malignancies and related conditions of lymphoid lineage (for example acute lymphocytic leukemia (ALL), chronic lymphocytic leukemia (CLL), chronic myeloid leukaemia (CML), B-cell lymphomas such as diffuse large B-cell lymphoma (DLBCL), Pre-B acute lymphoblastic leukaemia, Pre-B lymphomas, Large B-cell lymphomas, B-Cell acute lymphoblastic leukaemia, Philadelphia chromosome positive acute lymphoblastic leukaemia, Philadelphia chromosome positive chronic myeloid leukaemia, follicular lymphoma, Burkitt's lymphoma, mantle cell lymphoma, T-cell lymphomas and leukaemias, T-lineage acute lymphoblastic leukaemia (T-ALL), T-lineage lymphoblastic lymphoma (T-LL), peripheral T-cell lymphoma, adult T-cell leukaemia, natural killer (NK) cell lymphomas, Hodgkin's lymphomas, Non-Hodgkin's lymphomas, hairy cell leukaemia, monoclonal gammopathy of uncertain significance, plasmacytoma, multiple myeloma, and post-transplant lymphoproliferative disorders), and haematological malignancies and related conditions of myeloid lineage (for example acute myelogenous leukemia (AML), chronic myelogenous leukemia (CML), chronic myelomonocytic leukemia (CMML), hypereosinophilic syndrome, myeloproliferative disorders such as polycythaemia vera, essential thrombocythaemia and primary myelofibrosis, myeloproliferative syndrome, myelodysplastic syndrome, and promyelocytic leukemia); tumours of mesenchymal origin (for example sarcomas of soft tissue, bone or cartilage such as osteosarcomas, fibrosarcomas, chondrosarcomas, rhabdomyosarcomas, leiomyosarcomas, liposarcomas, angiosarcomas, myosarcoma, Kaposi's sarcoma, Ewing's sarcoma, synovial sarcomas, epithelioid sarcomas, gastrointestinal stromal tumours, benign and malignant histiocytomas, and dermatofibrosarcoma protuberans; neural crest cell-derived tumours including melanocytic tumours (for example, malignant melanoma or uveal melanoma), tumours of peripheral and cranial nerves, peripheral neuroblastic tumours (for example, neuroblastoma), embryonal tumors of the CNS, paraganglioma; tumours of the central or peripheral nervous system (for example, astrocytomas, gliomas and glioblastomas, gangliogliomas, ganglioneuromas, oligodendroglioma, meningiomas, ependymomas, pineal tumours and schwannomas); endocrine tumours (for example, pituitary tumours, adrenal tumours, islet cell tumours, parathyroid tumours, carcinoid tumours and medullary carcinoma of the thyroid); ocular and adnexal tumours (for example, retinoblastoma); germ cell and trophoblastic tumours (for example, teratomas, seminomas, dysgerminomas, hydatidiform moles and choriocarcinomas); and paediatric and embryonal tumours (for example medulloblastoma, neuroblastoma, Wilms tumour, and primitive neuroectodermal tumours); or syndromes, congenital or otherwise, which leave the patient susceptible to malignancy (for example, Xeroderma Pigmentosum).

Specific types of cancers or malignant tumours, either primary or secondary, that can be treated using this invention include breast cancer, skin cancer, bone cancer, prostate cancer, liver cancer, lung cancer, brain cancer, cancer of the larynx, gall bladder, pancreas, rectum, parathyroid, thyroid, adrenal, neural tissue, head and neck, colon, stomach, bronchi, kidneys, basal cell carcinoma, squamous cell carcinoma of both ulcerating and papillary type, metastatic skin carcinoma, osteo sarcoma, Ewing's sarcoma, veticulum cell sarcoma, myeloma, giant cell tumour, small-cell lung tumour, gallstones, islet cell tumour, primary brain tumour, acute and chronic lymphocytic and granulocytic tumours, hairy-cell tumour, adenoma, hyperplasia, medullary carcinoma, pheochromocytoma, mucosal neuronms, intestinal ganglioneuromas, hyperplastic corneal nerve tumour, marfanoid habitus tumour, Wilm's tumour, seminoma, ovarian tumor, leiomyomater, cervical dysplasia and in situ carcinoma, neuroblastoma, retinoblastoma, soft tissue sarcoma, malignant carcinoid, topical skin lesion, mycosis fimgoide, rhabdomyosarcoma, Kaposi's sarcoma, osteogenic and other sarcoma, malignant hypercalcemia, renal cell tumour, polycythemia vera, adenocarcinoma, glioblastoma multiforma, leukemias, lymphomas, malignant melanomas, epidermoid carcinomas, and other carcinomas and sarcomas.

Non-limiting examples of target intracellular proteins that may be targeted by the target ligand of the CLIPTAC and CLIPTAC precursors of the invention include eukaryotic, prokaryotic, fungal and viral proteins. The target proteins therefore include, but are not limited to, transport (nuclear, carrier, ion, channel, electron, protein), behavioural, receptor, cell death, cell differentiation, cell surface, structural proteins, cell adhesion, cell communication, cell motility, enzymes, cellular function (helicase, biosynthesis, motor, antioxidant, catalytic, metabolic, proteolytic), membrane fusion, development, proteins regulating biological processes, proteins with signal transducer activity, receptor activity, isomerase activity, enzyme regulator activity, chaperone regulator, binding activity, transcription regulator activity, translation regulator activity, structural molecule activity, ligase activity, extracellular organisation activity, kinase activity, biogenesis activity, ligase activity, and nucleic acid binding activity.

Target proteins may be selected from, and are therefore not limited to, DNA methyl transferases, AKT pathway proteins, MAPK/ERK pathway proteins, tyrosine kinases, epithelial growth factor receptors (EGFRs), fibroblast growth factor receptors (FGFRs), vascular endothelial growth factor receptors (VEGFRs), erythropoietin-producing human hepatocellular receptors (Ephs), tropomyosin receptor kinases, tumor necrosis factors, apoptosis regulator Bcl-2 family proteins, Aurora kinases, chromatin, G-protein coupled receptors (GPCRs), NF-κB pathway, HCV proteins, HIV proteins, Aspartyl proteases, Histone deacetylases (HDACs), glycosidases, lipases, histone acetyltransferase (HAT), cytokines and hormones.

Specific target proteins may be selected from ERK1/2, ERK5, A-Raf, B-Raf, C-Raf, c-Mos, Tpl2/Cot, MEK, MKK1, MKK2, MKK3, MKK4, MKK5, MKK6, MKK7, TYK2, JNK1, JNK2, JNK3, MEKK1, MEKK2, MEKK3, MEKK4, ASK1, ASK2, MLK1, MLK2, MLK3, p38 α, p38 β, p38 γ, p38 δ, BRD2, BRD3, BRD4, phosphatidyl inositol-3 kinase (PI3K), AKT, Protein kinase A (PKA), Protein Kinase B (PKB), Protein kinase C (PKC), mTOR, PDK-1, p70 S6 kinase, forkhead translocation factor, MELK, elF4E, Hsp90, Hsp70, Hsp60, topoisomerase type I, topoisomerase type II, DNMT1, DNMT3A, DNMT3B, Cdk11, Cdk2, Cdk3, Cdk4, Cdk5, Cdk6, Cdk7, α-tubulin, β-tubulin, γ-tubulin, δ-tubulin, ε-Tubulin, Janus Kinases (JAK1, JAK2, JAK3), ABL1, ABL2, EGFR, EPHA1, EPHA2, EPHA3, EPHA4, EPHA5, EPHA6, EPHA7, EPHA8, EPHA10, EPHB1, EPHB2, EPHB3, EPHB4, EPHB6, HER2/neu, Her3, Her4, ALK, FGFR1, FGFR2, FGFR3, FGFR4, IGF1R, INSR, INSRR, VEGFR-1, VEGFR-2, VEGFR-3, FLT-3, FLT4, PDGFRA, PDGFRB, CSF1R, Axl, IRAK4, SCFR, Fyn, MuSK, Btk, CSK, PLK4, Fes, MER, c-MET, LMTK2, FRK, ILK, Lck, TIE1, FAK, PTK6, TNNI3, ROSCCK4, ZAP-70, c-Src, Tec, Lyn, TrkA, TrkB, TrkC, RET, ROR1, ROR2, ACK1, Syk, MDM2, HRas, KRas, NRas, ROCK, PI3K, BACE1, BACE2, CTSD, CTSE, NAPSA, PGC, Renin, MMSET, Aurora A kinase, Aurora B kinase, Aurora C kinase, farnesyltransferase, telomerase, adenylyly cyclase, cAMP phosphodiesterase, PARP1, PARP2, PARP4, PARP-5a, PARP-5b, PKM2, Keap1, Nrf2, TNF, TRAIL, OX40L Lymphotoxin-alpha, IFNAR1, IFNAR2, IFN-α, IFN-β, IFN-γ, IFNLR1, CCL3, CCL4, CCL5, IL1α, IL1β, IL-2, IL-2, IL-4, IL-5, IL-6, IL-7, IL-9, IL-9, IL-10, IL-11, IL-12, IL-13, IL-15, IL-17, Bcl-2, BclxL, Bax, HCV helicase, E1, E2, p7, NS2, NS3, NS4A, NS4B, NS5A, NS5B, NF-κB1, NF-κB2, RelA, RelB, c-Rel, RIP1, ACE, HIV protease, HIV integrase, Gag, Pol, gp160, Tat, Rev, Nef, Vpr, Vif, Vpu, RNA polymerase, GABA transaminase, Reverse transcriptase, DNA polymerase, prolactin, ACTH, ANP, insulin, PDE, AMPK, iNOS, HDAC1, HDAC2, HDAC3, HDAC4, HDAC5, HDAC6, HDAC7, HDAC8, HDAC9, HDAC10, HDAC11, lactase, amylase lysozyme, neuraminidase, invertase, chitinase, hyaluronidase, maltase, sucrase, phosphatase, phosphorylases, P, Histidine decarboxylase, PTEN, histone lysine demethylase (KDM), GCN5, PCAF, Hat1, ATF-2, Tip60, MOZ, MORF, HBO1, p300, CBP, SRC-1, SRC-3, ACTR, TIF-2, TAF1, TFIIIC, protein O-mannosyl-transferase 1 (POMT1), amyloid β and Tau.

Other non-limiting examples of target intracellular proteins that may be targeted by the target ligand of the PROTAC and PROTAC precursors of the invention and the diseases in which such compositions find utility are listed in the table below:

| Intracellular target protein | Disease |
| --- | --- |
| ERK1/2 | Cancer, including hepatocellular carcinoma, of leukemaia (for example, acute and chronic leukaemias, acute myeloid leukaemia (AML), and chronic lymphocytic leukaemia (CLL)), mesothelioma (for example, malignant peritoneal mesothelioma or malignant pleural mesothelioma), melanoma, oesophageal, renal, colon, colorectal, lung e.g. mesothelioma or lung adenocarcinoma, breast, bladder, gastrointestinal, ovarian and prostate cancers. |
| ERK5 | Cancer, including hepatocellular carcinoma, of leukemaia (for example, acute and chronic leukaemias, acute myeloid leukaemia (AML), and chronic lymphocytic leukaemia (CLL)), mesothelioma (for example, malignant peritoneal mesothelioma or malignant pleural mesothelioma), melanoma, oesophageal, renal, colon, colorectal, lung e.g. mesothelioma or lung adenocarcinoma, breast, bladder, gastrointestinal, ovarian and prostate cancers. |
| BRD4 | Cancer, including acute myeloid leukaemia (AML), breast cancer, carcinoma, lung cancer, and T-cell acute lymphoblastic leukemia (T-ALL). |
| HDACs | Cancer, including breast cancer, skin cancer, bone cancer, prostate cancer, liver cancer, lung cancer, brain cancer, cancer of the larynx, gall bladder, pancreas, rectum, parathyroid, thyroid, adrenal, neural tissue, head and neck, colon, stomach, bronchi, kidneys, basal cell carcinoma, squamous cell carcinoma of both ulcerating and papillary type, metastatic skin carcinoma, osteo sarcoma, Ewing's sarcoma, veticulum cell sarcoma, myeloma, giant cell tumor, small-cell lung tumor, gallstones, islet cell tumor, primary brain tumor, acute and chronic lymphocytic and granulocytic tumors, hairy-cell tumor, adenoma, hyperplasia, medullary carcinoma, pheochromocytoma, mucosal neuronms, intestinal ganglloneuromas, hyperplastic corneal nerve tumor, marfanoid habitus tumor, Wilm's tumor, seminoma, ovarian tumor, leiomyomater tumor, cervical dysplasia and in situ carcinoma, neuroblastoma, retinoblastoma, soft tissue sarcoma, malignant carcinoid, topical skin lesion, mycosis fungoide, rhabdomyosarcoma, Kaposi's sarcoma, osteogenic and other sarcoma, malignant hypercalcemia, renal cell tumor, polycythermia vera, adenocarcinoma, glioblastoma multiforma, leukemias, lymphomas, malignant melanomas, epidermoid carcinomas, and other carcinomas and sarcomas, and hematologic disorders (for example, acute myeloid leukemia (AML), acute promyelocytic leukemia (APML), acute lymphoblastic leukemia (ALL), chronic myelogenous leukemia (CML), the myelodysplastic syndromes, and sickle cell anemia) |
| HATs | Cancer including prostate cancer, gastric carcinomas, colorectal carcinomas, cervical dysplasias, endometrial stromal sarcomas, colon cancer, lung cancer, breast cancer, ovarian cancer, and pancreatic cancers. |
| KDMs | Cancer including breast cancer, prostate cancer, ovarian cancer, colorectal cancer, renal cancer, esophageal squamous cell carcinoma, medulloblastoma, metastatic lung sarcomatoid carcinoma, B-cell lymphoma, Hodgkin's lymphoma and acute myeloid leukemia. |
| MBTs | Cancer |
| PMTs | Cancer |
| Tau | Neurodegenerative disease, including Alzheimer's disease and Parkinson's disease |
| amyloid β | Neurodegenerative disease, including Alzheimer's disease |

Tau, an important pathological protein of Alzheimer's disease and can mediate the toxicity of amyloid β. This target has recently been validated as a PROTAC target by e.g. Chu et al. (2016) *Specific Knockdown of Endogenous Tau Protein by Peptide-Directed Ubiquitin-Proteasome Degradation* Cell Chemical Biology 23: 453-461.

E3 Ubiquitin Ligase Ligands

Any moiety capable of recruiting E3 ubiquitin ligase may be used in the CLIPTAC and CLIPTAC precursors of the invention. Preferably, the moiety is a ligand for an E3 ubiquitin ligase, for example ligases selected from cereblon, von-Hippel-Lindau (VHL), MDM2, cIAP1 or XIAP. The ligand is preferably non-peptidic, for example a small molecule moiety.

Particularly preferred E3 ubiquitin ligase ligands include thalidomide (a ligand for the E3 ubiquitin ligase cereblon) and the small-molecule ligands for the VHL E3 ubiquitin ligase described, for example in, WO2013/106643 and by Galdeano (Galdeano, et al. (2014) Structure-Guided Design and Optimization of Small Molecules Targeting the Protein-Protein Interaction between the von Hippel-Lindau (VHL) E3 Ubiquitin Ligase and the Hypoxia Inducible Factor (HIF) Alpha Subunit with in Vitro Nanomolar Affinities. *J. Med. Chem.* 57: 8657-8663) (the contents of which are hereby incorporated by reference).

Formulation

The compound of the invention may take any form. It may be synthesised using techniques described in the art.

Illustrative pharmaceutically acceptable salts are prepared from formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, cyclohexylaminosulfonic, algenic, hydroxybutyric, galactaric and galacturonic acids.

Suitable pharmaceutically-acceptable base addition salts include metallic ion salts and organic ion salts. Metallic ion salts include, but are not limited to, appropriate alkali metal (group Ia) salts, alkaline earth metal (group IIa) salts and other physiologically acceptable metal ions. Such salts can be made from the ions of aluminium, calcium, lithium, magnesium, potassium, sodium and zinc. Organic salts can be made from tertiary amines and quaternary ammonium salts, including in part, trimethylamine, diethylamine, N,N'-dibenzylethylenediamine, chloroprocaine, choline, diethanolamine, ethylenediamine, meglumine (N-methylglucamine) and procaine. All of the above salts can be prepared by those skilled in the art by conventional means from the corresponding compound.

Pharmaceutical compositions can include stabilizers, antioxidants, colorants and diluents. Pharmaceutically acceptable carriers and additives are chosen such that side effects from the pharmaceutical compound are minimized and the performance of the compound is not compromised to such an extent that treatment is ineffective.

The pharmaceutical compositions may be administered enterally and/or parenterally. Oral (intra-gastric) is a typical route of administration. Pharmaceutically acceptable carriers can be in solid dosage forms, including tablets, capsules, pills and granules, which can be prepared with coatings and shells, such as enteric coatings and others well known in the art. Liquid dosage forms for oral administration include pharmaceutically acceptable emulsions, solutions, suspensions, syrups and elixirs. Parenteral administration includes subcutaneous, intramuscular, intradermal, intravenous, and other routes known in the art. Enteral administration includes solution, tablets, sustained release capsules, enteric coated capsules, and syrups. When administered, the pharmaceutical composition can be at or near body temperature.

Compositions intended for oral use can be prepared according to any method known in the art for the manufacture of pharmaceutical compositions and such compositions can contain one or more agents selected from the group consisting of sweetening agents, flavouring agents, colouring agents and preserving agents in order to provide pharmaceutically elegant and palatable preparations. Tablets contain the active ingredient in admixture with non-toxic pharmaceutically acceptable excipients, which are suitable for the manufacture of tablets. These excipients may be, for example, inert diluents, such as calcium carbonate, sodium carbonate, lactose, calcium phosphate or sodium phosphate, granulating and disintegrating agents, for example, maize starch, or alginic acid, binding agents, for example starch, gelatin or acacia, and lubricating agents, for example magnesium stearate, stearic acid, or talc. Tablets can be uncoated or they can be coated by known techniques, for example to delay disintegration and absorption in the gastrointestinal tract and thereby provide sustained action over a longer period. For example, a time delay material such as glyceryl monostearate or glyceryl distearate can be employed. Formulations for oral use can also be presented as hard gelatin capsules wherein the active ingredients are mixed with an inert solid diluent, for example, calcium carbonate, calcium phosphate or kaolin, or as soft gelatin capsules wherein the active ingredients are present as such, or mixed with water or an oil medium, for example, peanut oil, liquid paraffin or olive oil.

Aqueous suspensions can be produced that contain the active materials in a mixture with excipients suitable for the manufacture of aqueous suspensions. Such excipients include suspending agents, for example, sodium carboxymethylcellulose, methylcellulose, hydroxypropylmethylcellulose, sodium alginate, polyvinylpyrrolidone, gum tragacanth and gum acacia; dispersing or wetting agents can be naturally-occurring phosphatides, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyoxyethylene sorbitan monooleate. Aqueous suspensions can also contain one or more preservatives, for example, ethyl or N-propyl p-hydroxybenzoate, one or more colouring agents, one or more flavouring-agents, or one or more sweetening agents, such as sucrose or saccharin. Suitable aqueous vehicles include Ringer's solution and isotonic sodium chloride. Aqueous suspensions according to the invention may include suspending agents such as cellulose derivatives, sodium alginate, polyvinylpyrrolidone and gum tragacanth, and a wetting agent such as lecithin. Suitable preservatives for aqueous suspensions include ethyl and N-propyl p-hydroxybenzoate.

Oily suspensions may be formulated by suspending the active ingredients in an omega-3 fatty acid, a vegetable oil, for example, *arachis* oil, olive oil, sesame oil or coconut oil, or in a mineral oil such as liquid paraffin. The oily suspensions can contain a thickening agent, for example beeswax, hard paraffin or cetyl alcohol.

Sweetening agents, such as those set forth above, and flavouring agents can be added to provide a palatable oral preparation. These compositions can be preserved by addition of an antioxidant such as ascorbic acid.

Dispersible powders and granules suitable for preparation of an aqueous suspension by addition of water provide the active ingredient in admixture with a dispersing or wetting agent, a suspending agent and one or more preservatives. Suitable dispersing or wetting agents and suspending agents are exemplified by those already mentioned above. Additional excipients, for example sweetening, flavouring and colouring agents, can also be present.

Syrups and elixirs containing the compound of the invention can be formulated with sweetening agents, for example glycerol, sorbitol, or sucrose. Such formulations can also contain a demulcent, a preservative and flavouring and colouring agents.

The compound of the invention can be administered parenterally, for example subcutaneously, intravenously, or intramuscularly, or by infusion techniques, in the form of sterile injectable aqueous or oleaginous suspensions. Such suspensions can be formulated according to known art using suitable dispersing or wetting agents and suspending agents such as those mentioned above or other acceptable agents. A sterile injectable preparation can be a sterile injectable solution or suspension in a non-toxic parenterally acceptable diluent or solvent, for example a solution in 1,3-butanediol. Among acceptable vehicles and solvents that can be employed are water, Ringer's solution and isotonic sodium chloride solution. In addition, sterile fixed oils are conventionally employed as a solvent or suspending medium. For this purpose, any bland fixed oil may be employed, including synthetic mono- or diglycerides. In addition, omega-3 polyunsaturated fatty acids can find use in preparation of injectables. Administration can also be by inhalation, in the form of aerosols or solutions for nebulizers, or rectally, in the form of suppositories prepared by mixing the drug with a suitable non-irritating excipient which is solid at ordinary temperature, but liquid at rectal temperature and will therefore, melt in the rectum to release the drug. Such materials are cocoa butter and polyethylene glycols. Also encompassed by the present invention is buccal and sub-lingual administration, including administration in the form of lozenges, pastilles or a chewable gum comprising the compounds set forth herein. The compounds can be deposited in a flavoured base, usually sucrose, and acacia or tragacanth.

Other methods for administration of the compounds of the invention include dermal patches that release the medicaments directly into and/or through a subject's skin.

Topical delivery systems are also encompassed by the present invention and include ointments, powders, sprays, creams, jellies, collyriums, solutions or suspensions.

Compositions of the present invention can optionally be supplemented with additional agents such as, for example, viscosity enhancers, preservatives and, surfactants and penetration enhancers. Viscosity-building agents include, for example, polyvinyl alcohol, polyvinyl pyrrolidone, methylcellulose, hydroxypropylmethylcellulose, hydroxyethylcellulose, carboxymethylcellulose, hydroxypropylcellulose or other agents known to those skilled in the art. Such agents are typically employed at a level of about 0.01% to about 2% by weight of a pharmaceutical composition.

Preservatives are optionally employed to prevent microbial growth prior to or during use. Suitable preservatives include polyquaternium-1, benzalkonium chloride, thimerosal, chlorobutanol, methylparaben, propylparaben, phenylethyl alcohol, edetate disodium, sorbic acid, or other agents known to those skilled in the art. Typically, such preservatives are employed at a level of about 0.001% to about 1.0% by weight of a pharmaceutical composition.

Solubility of components of the present compositions can be enhanced by a surfactant or other appropriate cosolvent in the composition. Such cosolvents include polysorbates 20, 60 and 80, polyoxyethylene/polyoxypropylene surfactants (e. g., Pluronic F-68, F-84 and P-103), cyclodextrin, or other agents known to those skilled in the art. Typically, such cosolvents are employed at a level of about 0.01% to about 2% by weight of a pharmaceutical composition.

Pharmaceutically acceptable excipients and carriers encompass all the foregoing and the like. The above considerations concerning effective formulations and administration procedures are well known in the art and are described in standard textbooks. See for example Remington: The Science and Practice of Pharmacy, 20th Edition (Lippincott, Williams and Wilkins), 2000; Lieberman et al., ed., Pharmaceutical Dosage Forms, Marcel Decker, New York, N.Y. (1980) and Kibbe et al., ed., Handbook of Pharmaceutical Excipients (3rd Edition), American Pharmaceutical Association, Washington (1999). Thus, in embodiments where the compound of the invention is formulated together with a pharmaceutically acceptable excipient, any suitable excipient may be used, including for example inert diluents, disintegrating agents, binding agents, lubricating agents, sweetening agents, flavouring agents, colouring agents and preservatives. Suitable inert diluents include sodium and calcium carbonate, sodium and calcium phosphate, and lactose, while cornstarch and alginic acid are suitable disintegrating agents. Binding agents may include starch and gelatin, while the lubricating agent, if present, will generally be magnesium stearate, stearic acid or talc. The pharmaceutical compositions may take any suitable form, and include for example tablets, elixirs, capsules, solutions, suspensions, powders, granules, nail lacquers, varnishes and veneers, skin patches and aerosols.

The pharmaceutical composition may take the form of a kit of parts, which kit may comprise the composition of the invention together with instructions for use and/or a plurality of different components in unit dosage form.

For oral administration the compound of the invention can be formulated into solid or liquid preparations such as capsules, pills, tablets, troches, lozenges, melts, powders, granules, solutions, suspensions, dispersions or emulsions (which solutions, suspensions dispersions or emulsions may be aqueous or non-aqueous). The solid unit dosage forms can be a capsule which can be of the ordinary hard- or soft-shelled gelatin type containing, for example, surfactants, lubricants, and inert fillers such as lactose, sucrose, calcium phosphate, and cornstarch. Tablets for oral use may include the compound of the invention, either alone or together with pharmaceutically acceptable excipients, such as inert diluents, disintegrating agents, binding agents, lubricating agents, sweetening agents, flavouring agents, colouring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract. Capsules for oral use include hard gelatin capsules in which the compound of the invention is mixed with a solid diluent, and soft gelatin capsules wherein the active ingredient is mixed with water or an oil such as peanut oil, liquid paraffin or olive oil. Formulations for rectal administration may be presented as a suppository with a suitable base comprising for example cocoa butter or a salicylate. Formulations suitable for vaginal administration may be presented as pessaries, tampons, creams, gels, pastes, foams or spray formulations containing in addition to the active ingredient such carriers as are known in the art to be appropriate. For intramuscular, intraperitoneal, subcutaneous and intravenous use, the compounds of the invention will generally be provided in sterile aqueous solutions or suspensions, buffered to an appropriate pH and isotonicity.

The compounds of the invention may also be presented as liposome formulations.

In another embodiment, the compounds of the invention are tableted with conventional tablet bases such as lactose, sucrose, and cornstarch in combination with binders such as acacia, cornstarch, or gelatin, disintegrating agents intended to assist the break-up and dissolution of the tablet following administration such as potato starch, alginic acid, corn starch, and guar gum, lubricants intended to improve the flow of tablet granulations and to prevent the adhesion of tablet material to the surfaces of the tablet dies and punches, for example, talc, stearic acid, or magnesium, calcium, or zinc stearate, dyes, colouring agents, and flavouring agents intended to enhance the aesthetic qualities of the tablets and make them more acceptable to the patient.

Suitable excipients for use in oral liquid dosage forms include diluents such as water and alcohols, for example, ethanol, benzyl alcohol, and the polyethylene alcohols, either with or without the addition of a pharmaceutically acceptably surfactant, suspending agent or emulsifying agent.

The compounds of the invention may also be administered parenterally, that is, subcutaneously, intravenously, intramuscularly, or interperitoneally. In such embodiments, the compound is provided as injectable doses in a physiologically acceptable diluent together with a pharmaceutical carrier (which can be a sterile liquid or mixture of liquids).

Suitable liquids include water, saline, aqueous dextrose and related compound solutions, an alcohol (such as ethanol, isopropanol, or hexadecyl alcohol), glycols (such as propylene glycol or polyethylene glycol), glycerol ketals (such as 2,2-dimethyl-1,3-dioxolane-4-methanol), ethers (such as poly(ethylene-glycol) 400), an oil, a fatty acid, a fatty acid ester or glyceride, or an acetylated fatty acid glyceride with or without the addition of a pharmaceutically acceptable surfactant (such as a soap or a detergent), suspending agent (such as pectin, carbomers, methylcellulose, hydroxypropylmethylcellulose, or carboxymethylcellulose), or emulsifying agent and other pharmaceutically adjuvants. Suitable oils which can be used in the parenteral formulations of this invention are those of petroleum, animal, vegetable, or synthetic origin, for example, peanut oil, soybean oil, sesame oil, cottonseed oil, corn oil, olive oil, petrolatum, and mineral oil.

Suitable fatty acids include oleic acid, stearic acid, and isostearic acid. Suitable fatty acid esters are, for example, ethyl oleate and isopropyl myristate. Suitable soaps include fatty alkali metal, ammonium, and triethanolamine salts and suitable detergents include cationic detergents, for example, dimethyl dialkyl ammonium halides, alkyl pyridinium halides, and alkylamines acetates; anionic detergents, for example, alkyl, aryl, and olefin sulphonates, alkyl, olefin, ether, and monoglyceride sulphates, and sulphosuccinates; nonionic detergents, for example, fatty amine oxides, fatty acid alkanolamides, and polyoxyethylenepolypropylene copolymers; and amphoteric detergents, for example, alkyl-beta-aminopropionates, and 2-alkylimidazoline quarternary ammonium salts, as well as mixtures.

The parenteral compositions of this invention will typically contain from about 0.5 to about 25% by weight of the compound of the invention in solution. Preservatives and buffers may also be used. In order to minimize or eliminate irritation at the site of injection, such compositions may contain a non-ionic surfactant having a hydrophile-lipophile balance (HLB) of from about 12 to about 17. The quantity of surfactant in such formulations ranges from about 5 to about 15% by weight. The surfactant can be a single component having the above HLB or can be a mixture of two or more components having the desired HLB. Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The compounds of the invention may also be administered topically, and when done so the carrier may suitably comprise a solution, ointment or gel base. The base, for example, may comprise one or more of the following: petrolatum, lanolin, polyethylene glycols, bee wax, mineral oil, diluents such as water and alcohol, and emulsifiers and stabilizers. Topical formulations may contain a concentration of the compound from about 0.1 to about 10% w/v (weight per unit volume).

Posology

The CLIPTAC and CLIPTAC precursors of the present invention can be administered by oral or parenteral routes, including intravenous, intramuscular, intraperitoneal, subcutaneous, transdermal, airway (aerosol), rectal, vaginal and topical (including buccal and sublingual) administration.

The amount of the composition administered can vary widely according to the particular dosage unit employed, the period of treatment, the age and sex of the patient treated, the nature and extent of the disorder treated, and the particular composition selected.

In general, the effective amount of the composition administered will generally range from about 0.01 mg/kg to 10000 mg/kg daily. A unit dosage may contain from 0.05 to 500 mg of the composition, and can be taken one or more times per day. The composition can be administered with a pharmaceutical carrier using conventional dosage unit forms either orally, parenterally or topically, as described below.

The preferred route of administration is oral administration. In general a suitable dose will be in the range of 0.01 to 500 mg per kilogram body weight of the recipient per day, preferably in the range of 0.1 to 1000 mg per kilogram body weight per day and most preferably in the range 1 to 5 mg per kilogram body weight per day.

The desired dose is preferably presented as a single dose for daily administration. However, two, three, four, five or six or more sub-doses administered at appropriate intervals throughout the day may also be employed. These sub-doses may be administered in unit dosage forms, for example, containing 0.001 to 100 mg, preferably 0.01 to 10 mg, and most preferably 0.5 to 1.0 mg of active ingredient per unit dosage form.

In determining an effective amount or dose, a number of factors are considered by the attending physician, including, but not limited to, the potency and duration of action of the CLIPTAC and CLIPTAC precursors used, the nature and severity of the illness to be treated, as well as the sex, age, weight, general health and individual responsiveness of the patient to be treated, and other relevant circumstances. Those skilled in the art will appreciate that dosages can also be determined with guidance from Goodman & Goldman's The Pharmacological Basis of Therapeutics, Ninth Edition (1996), Appendix II, pp. 1707-1711.

The amount of the composition that can be combined with carrier materials to produce a single dosage form varies depending upon the subject to be treated and the particular mode of administration. For example, a formulation intended for oral administration to humans can contain about 0.5 mg to about 7 g of active agent compounded optionally with an appropriate and convenient amount of carrier material which can vary from about 5 to about 95 percent of the total composition. Dosage unit forms for the PROTAC and PROTAC precursors of the invention generally contain about 1 mg to about 500 mg of the active ingredient(s), for example 5 mg, 10 mg, 20 mg, 25 mg, 50 mg, 100 mg, 200 mg, 300 mg, 400 mg, 500 mg, 600 mg, 800 mg or 1000 mg.

The effectiveness of a particular dosage of the composition of the invention can be determined by monitoring the effect of a given dosage on the progression of the disease or its prevention.

The CLIPTAC or CLIPTAC precursor composition may be dosed separately or as a unitary composition. Typically, they are administered sequentially. In such circumstances, the first component as herein defined may be introduced into the cell before the second component as herein defined, for example the second component may be introduced into the cell after a time sufficient for the first component to bind to the intracellular target protein has elapsed.

Combinations

Examples of therapeutic agents or treatments which may be administered in combination with the CLIPTAC and CLIPTAC precursors include but are not limited to: topoisomerase I inhibitors, antimetabolites, tubulin targeting agents, DNA binder and topoisomerase II inhibitors, alkylating agents, monoclonal antibodies, anti-hormones, signal transduction inhibitors, ubiquitin-proteasome pathway inhibitors, immunotherapies, regulators of cell death, DNA methyl transferase inhibitors, cytokines and retinoids, chromatin targeted therapies, radiotherapy and other therapeutic or prophylactic agents.

Particular examples of therapeutic agents or adjuvants (or salts thereof), include but are not limited to any one or more of the agents selected from groups below:

(i) Platinum compounds, for example cisplatin (optionally combined with amifostine), carboplatin or oxaliplatin;

(ii) Taxane compounds, for example paclitaxel, paclitaxel protein bound particles (Abraxane™), docetaxel, cabazitaxel or larotaxel;

(iii) Topoisomerase I inhibitors, for example camptothecin compounds, for example camptothecin, irinotecan (CPT11), SN-38, or topotecan;

(iv) Topoisomerase II inhibitors, for example anti-tumour epipodophyllotoxins or podophyllotoxin derivatives for example etoposide, or teniposide;

(v) Vinca alkaloids, for example vinblastine, vincristine, liposomal vincristine (Onco-TCS), vinorelbine, vindesine, vinflunine or vinvesir;

(vi) Nucleoside derivatives, for example 5-fluorouracil (5-FU, optionally in combination with leucovorin), gemcitabine, capecitabine, tegafur, UFT, S1, cladribine, cytarabine (Ara-C, cytosine arabinoside), fludarabine, clofarabine, or nelarabine;

(vii) Antimetabolites, for example clofarabine, aminopterin, or methotrexate, azacitidine, cytarabine, floxuridine, pentostatin, thioguanine, thiopurine, 6-mercaptopurine, or hydroxyurea (hydroxycarbamide);

(viii) Alkylating agents, such as nitrogen mustards or nitrosourea, for example cyclophosphamide, chlorambucil, carmustine (BCNU), bendamustine, thiotepa, melphalan, treosulfan, lomustine (CCNU), altretamine, busulfan, dacarbazine, estramustine, fotemustine, ifosfamide (optionally in combination with mesna), pipobroman, procarbazine, streptozocin, temozolomide, uracil, mechlorethamine, methylcyclohexylchloroethylnitrosurea, or nimustine (ACNU);

(ix) Anthracyclines, anthracenediones and related drugs, for example daunorubicin, doxorubicin (optionally in combination with dexrazoxane), liposomal formulations of doxorubicin (eg. Caelyx™, Myocet™, Doxil™), idarubicin, mitoxantrone, epirubicin, amsacrine, or valrubicin;

(x) Epothilones, for example ixabepilone, patupilone, BMS-310705, KOS-862 and ZK-EPO, epothilone A, epothilone B, desoxyepothilone B (also known as epothilone D or KOS-862), aza-epothilone B (also known as BMS-247550), aulimalide, isolaulimalide, or luetherobin;

(xi) DNA methyl transferase inhibitors, for example temozolomide, azacytidine, decitabine or guadecitabine (SGI-110);

(xii) Antifolates, for example methotrexate, pemetrexed disodium, or raltitrexed;

(xiii) Cytotoxic antibiotics, for example antinomycin D, bleomycin, mitomycin C, dactinomycin, carminomycin, daunomycin, levamisole, plicamycin, or mithramycin;

(xiv) Tubulin-binding agents, for example combrestatin, colchicines or nocodazole;

(xv) Signal Transduction inhibitors such as Kinase inhibitors for example receptor tyrosine kinase inhibitors (e.g. EGFR (epithelial growth factor receptor) inhibitors, VEGFR (vascular endothelial growth factor receptor) inhibitors, PDGFR (platelet-derived growth factor receptor) inhibitors, Axl inhibitors, MTKI (multi target kinase inhibitors), Raf inhibitors, ROCK inhibitors, mTOR inhibitors, MEK inhibitors or PI3K Inhibitors) for example imatinib mesylate, erlotinib, gefitinib, dasatinib, lapatinib, dovotinib, axitinib, nilotinib, vandetanib, vatalinib, pazopanib, sorafenib, sunitinib, temsirolimus, everolimus (RAD 001), vemurafenib (PLX4032 or RG7204), dabrafenib, encorafenib, selumetinib (AZD6244), trametinib (GSK121120212), dactolisib (BEZ235), buparlisib (BKM-120; NVP-BKM-120), BYL719, copanlisib (BAY-80-6946), ZSTK-474, CUDC-907, apitolisib (GDC-0980; RG-7422), pictilisib (pictrelisib, GDC-0941, RG-7321), GDC-0032, GDC-0068, GSK-2636771, idelalisib (formerly CAL-101, GS 1101, GS-1101), MLN1117 (INK1117), MLN0128 (INK128), IPI-145 (INK1197), LY-3023414, ipatasertib, afuresertib, MK-2206, MK-8156, LY-3023414, LY294002, SF1126 or PI-103, sonolisib (PX-866), or AT13148.

(xvi) Aurora kinase inhibitors for example AT9283, barasertib (AZD1152), TAK-901, MK0457 (VX680), cenisertib (R-763), danusertib (PHA-739358), alisertib (MLN-8237), or MP-470;

(xvii) CDK inhibitors for example AT7519, roscovitine, seliciclib, alvocidib (flavopiridol), dinaciclib (SCH-727965), 7-hydroxy-staurosporine (UCN-01), JNJ-7706621, BMS-387032 (a.k.a. SNS-032), PHA533533, ZK-304709, or AZD-5438 and including CDK4 inhibitors such as palbociclib (PD332991) and ribociclib (LEE-011);

(xviii) PKA/B inhibitors and PKB (akt) pathway inhibitors for example AT13148, AZ-5363, Semaphore, SF1126 and MTOR inhibitors such as rapamycin analogues, AP23841 and AP23573, calmodulin inhibitors (forkhead translocation inhibitors), API-2/TCN (triciribine), RX-0201, enzastaurin HCl (LY317615), NL-71-101, SR-13668, PX-316, or KRX-0401 (perifosine/NSC 639966);

(xix) Hsp90 inhibitors for example onalespib (AT13387), herbimycin, geldanamycin (GA), 17-allylamino-17-desmethoxygeldanamycin (17-AAG) e.g. NSC-330507, Kos-953 and CNF-1010, 17-dimethylaminoethylamino-17-demethoxygeldanamycin hydrochloride (17-DMAG) e.g. NSC-707545 and Kos-1022, NVP-AUY922 (VER-52296), NVP-BEP800, CNF-2024 (BIIB-021 an oral purine), ganetespib (STA-9090), SNX-5422 (SC-102112) or IPI-504;

(xx) Monoclonal Antibodies (unconjugated or conjugated to radioisotopes, toxins or other agents), antibody derivatives and related agents, such as anti-CD, anti-VEGFR, anti-HER2 or anti-EGFR antibodies, for example rituximab (CD20), ofatumumab (CD20), ibritumomab tiuxetan (CD20), GA101 (CD20), tositumomab (CD20), epratuzumab (CD22), lintuzumab (CD33), gemtuzumab ozogamicin (CD33), alemtuzumab (CD52), galiximab (CD80), trastuzumab (HER2 antibody), pertuzumab (HER2), trastuzumab-DM1 (HER2), ertumaxomab (HER2 and CD3), cetuximab (EGFR), panitumumab (EGFR), necitumumab (EGFR), nimotuzumab (EGFR), bevacizumab (VEGF), catumaxomab (EpCAM and CD3), abagovomab (CA125), farletuzumab (folate receptor), elotuzumab (CS1), denosumab (RANK ligand), figitumumab (IGF1R), CP751,871 (IGF1R), mapatumumab (TRAIL receptor), metMAB (met), mitumomab (GD3 ganglioside), naptumomab estafenatox (5T4), or siltuximab (IL6) or immunomodulating agents such as CTLA-4 blocking antibodies and/or antibodies against PD-1 and PD-L1 and/or PD-L2 for example ipilimumab (CTLA4), MK-3475 (pembrolizumab, formerly lambrolizumab, anti-PD-1), nivolumab (a anti-PD-1), BMS-936559 (anti-PD-L1), MPDL320A, AMP-514 or MEDI4736 (anti-PD-L1), or tremelimumab (formerly ticilimumab, CP-675,206, anti-CTLA-4);

(xxi) Estrogen receptor antagonists or selective estrogen receptor modulators (SERMs) or inhibitors of estrogen synthesis, for example tamoxifen, fulvestrant, toremifene, droloxifene, faslodex, or raloxifene;

(xxii) Aromatase inhibitors and related drugs, such as exemestane, anastrozole, letrazole, testolactone aminoglutethimide, mitotane or vorozole;

(xxiii) Antiandrogens (i.e. androgen receptor antagonists) and related agents for example bicalutamide, nilutamide, flutamide, cyproterone, or ketoconazole;

(xxiv) Hormones and analogues thereof such as medroxyprogesterone, diethylstilbestrol (a.k.a. diethylstilboestrol) or octreotide;

(xxv) Steroids for example dromostanolone propionate, megestrol acetate, nandrolone (decanoate, phenpropionate), fluoxymestrone or gossypol, (xxvi) Steroidal cytochrome P450 17alpha-hydroxylase-17,20-lyase inhibitor (CYP17), e.g. abiraterone;

(xxvii) Gonadotropin releasing hormone agonists or antagonists (GnRAs) for example abarelix, goserelin acetate, histrelin acetate, leuprolide acetate, triptorelin, buserelin, or deslorelin;

(xxviii) Glucocorticoids, for example prednisone, prednisolone, dexamethasone;

(xxix) Differentiating agents, such as retinoids, rexinoids, vitamin D or retinoic acid and retinoic acid metabolism blocking agents (RAMBA) for example accutane, alitretinoin, bexarotene, or tretinoin;

(xxx) Farnesyltransferase inhibitors for example tipifarnib;

(xxxi) Chromatin targeted therapies such as histone deacetylase (HDAC) inhibitors for example sodium butyrate, suberoylanilide hydroxamide acid (SAHA), depsipeptide (FR 901228), dacinostat (NVP-LAQ824), R306465/JNJ-16241199, JNJ-26481585, trichostatin A, vorinostat, chlamydocin, A-173, JNJ-MGCD-0103, PXD-101, or apicidin;

(xxxii) Drugs targeting the ubiquitin-proteasome pathway including proteasome Inhibitors for example bortezomib, carfilzomib, CEP-18770, MLN-9708, or ONX-0912; NEDD8 inhibitors; HDM2 antagonist and deubiquitinases (DUBs);

(xxxiii) Photodynamic drugs for example porfimer sodium or temoporfin;

(xxxiv) Marine organism-derived anticancer agents such as trabectidin;

(xxxv) Radiolabelled drugs for radioimmunotherapy for example with a beta particle-emitting isotope (e.g., Iodine-131, Yittrium-90) or an alpha particle-emitting isotope (e.g., Bismuth-213 or Actinium-225) for example ibritumomab, Iodine tositumomab or alpha radium;

(xxxvi) Telomerase inhibitors for example telomestatin;

(xxxvii) Matrix metalloproteinase inhibitors for example batimastat, marimastat, prinostat or metastat;

(xxxviii) Recombinant interferons (such as interferon-γ and interferon α) and interleukins (e.g. interleukin 2), for example aldesleukin, denileukin diftitox, interferon alfa 2a, interferon alfa 2b, or peginterferon alfa 2b;

(xxxix) Selective immunoresponse modulators for example thalidomide, or lenalidomide;

(xl) Therapeutic Vaccines such as sipuleucel-T (Provenge) or OncoVex;

(xli) Cytokine-activating agents include Picibanil, Romurtide, Sizofiran, Virulizin, or Thymosin;

(xlii) Arsenic trioxide;

(xliii) Inhibitors of G-protein coupled receptors (GPCR) for example atrasentan;

(xliv) Enzymes such as L-asparaginase, pegaspargase, rasburicase, or pegademase;

(xlv) DNA repair inhibitors such as PARP inhibitors for example, olaparib, velaparib, iniparib, INO-1001, AG-014699, or ONO-2231;

(xlvi) Agonists of Death receptor (e.g. TNF-related apoptosis inducing ligand (TRAIL) receptor), such as mapatumumab (formerly HGS-ETR1), conatumumab (formerly AMG 655), PRO95780, lexatumumab, dulanermin, CS-1008, apomab or recombinant TRAIL ligands such as recombinant Human TRAIL/Apo2 Ligand;

(xlvii) Immunotherapies such as immune checkpoint inhibitors; cancer vaccines and CAR-T cell therapy;

(xlviii) Regulators of Cell death (apoptosis) including Bcl-2 (B-cell lymphoma 2) antagonists such as venetoclax (ABT-199 or GDC-0199), ABT-737, ABT-263, TW-37, sabutoclax, obatoclax, and MIM1 and IAP antagonists including LCL-161 (Novartis), Debio-1143 (Debiopharma/Ascenta), AZD5582, Birinapant/TL-32711 (TetraLogic), CUDC-427/GDC-0917/RG-7459 (Genentech), JP1201 (Joyant), T-3256336 (Takeda), GDC-0152 (Genentech), HGS-1029/AEG-40826 (HGS/Aegera) or ASTX-660;

(xlix) Prophylactic agents (adjuncts); i.e. agents that reduce or alleviate some of the side effects associated with chemotherapy agents, for example anti-emetic agents, agents that prevent or decrease the duration of chemotherapy-associated neutropenia and prevent complications that arise from reduced levels of platelets, red blood cells or white blood cells, for example interleukin-11 (e.g. oprelvekin), erythropoietin (EPO) and analogues thereof (e.g. darbepoetin alfa), colony-stimulating factor analogs such as granulocyte macrophage-colony stimulating factor (GM-CSF) (e.g. sargramostim), and granulocyte-colony stimulating factor (G-CSF) and analogues thereof (e.g. filgrastim, pegfilgrastim), agents that inhibit bone resorption such as denosumab or bisphosphonates e.g. zoledronate, zoledronic acid, pamidronate and ibandronate, agents that suppress inflammatory responses such as dexamethasone, prednisone, and prednisolone, agents used to reduce blood levels of growth hormone and IGF-I (and other hormones) in patients with acromegaly or other rare hormone-producing tumours, such as synthetic forms of the hormone somatostatin e.g. octreotide acetate, antidote to drugs that decrease levels of folic acid such as leucovorin, or folinic acid, agents for pain e.g. opiates such as morphine, diamorphine and fentanyl, non-steroidal anti-inflammatory drugs (NSAID) such as COX-2 inhibitors for example celecoxib, etoricoxib and lumiracoxib, agents for mucositis e.g. palifermin, agents for the treatment of side-effects including anorexia, cachexia, oedema or thromboembolic episodes, such as megestrol acetate; and (I) radiotherapy for radical, palliative or prophylactic purposes.

Each of the compounds present in the combinations of the invention may be given in individually varying dose schedules and via different routes. As such, the posology of each of the two or more agents may differ: each may be administered at the same time or at different times. A person skilled in the art would know through his or her common general knowledge the dosing regimes and combination therapies to use. For example, the compound of the invention may be used in combination with one or more other agents which are administered according to their existing combination regimen. Examples of standard combination regimens are provided below.

The taxane compound is advantageously administered in a dosage of 50 to 400 mg per square meter ($mg/m^2$) of body surface area, for example 75 to 250 $mg/m^2$, particularly for paclitaxel in a dosage of about 175 to 250 $mg/m^2$ and for docetaxel in about 75 to 150 $mg/m^2$ per course of treatment.

The camptothecin compound is advantageously administered in a dosage of 0.1 to 400 mg per square meter ($mg/m^2$) of body surface area, for example 1 to 300 $mg/m^2$, particularly for irinotecan in a dosage of about 100 to 350 $mg/m^2$ and for topotecan in about 1 to 2 $mg/m^2$ per course of treatment.

The anti-tumour podophyllotoxin derivative is advantageously administered in a dosage of 30 to 300 mg per square meter ($mg/m^2$) of body surface area, for example 50 to 250 $mg/m^2$, particularly for etoposide in a dosage of about 35 to 100 $mg/m^2$ and for teniposide in about 50 to 250 $mg/m^2$ per course of treatment.

The anti-tumour *vinca* alkaloid is advantageously administered in a dosage of 2 to 30 mg per square meter ($mg/m^2$) of body surface area, particularly for vinblastine in a dosage of about 3 to 12 $mg/m^2$, for vincristine in a dosage of about 1 to 2 $mg/m^2$, and for vinorelbine in dosage of about 10 to 30 $mg/m^2$ per course of treatment.

The anti-tumour nucleoside derivative is advantageously administered in a dosage of 200 to 2500 mg per square meter ($mg/m^2$) of body surface area, for example 700 to 1500 $mg/m^2$, particularly for 5-FU in a dosage of 200 to 500 $mg/m^2$, for gemcitabine in a dosage of about 800 to 1200 $mg/m^2$ and for capecitabine in about 1000 to 2500 $mg/m^2$ per course of treatment.

The alkylating agents such as nitrogen mustard or nitrosourea is advantageously administered in a dosage of 100 to 500 mg per square meter ($mg/m^2$) of body surface area, for example 120 to 200 $mg/m^2$, particularly for cyclophosphamide in a dosage of about 100 to 500 $mg/m^2$, for chlorambucil in a dosage of about 0.1 to 0.2 mg/kg, for carmustine in a dosage of about 150 to 200 $mg/m^2$, and for lomustine in a dosage of about 100 to 150 $mg/m^2$ per course of treatment.

The anti-tumour anthracycline derivative is advantageously administered in a dosage of 10 to 75 mg per square meter ($mg/m^2$) of body surface area, for example 15 to 60 $mg/m^2$, particularly for doxorubicin in a dosage of about 40 to 75 $mg/m^2$, for daunorubicin in a dosage of about 25 to 45 $mg/m^2$, and for idarubicin in a dosage of about 10 to 15 $mg/m^2$ per course of treatment.

The antiestrogen agent is advantageously administered in a dosage of about 1 to 100 mg daily depending on the particular agent and the condition being treated. Tamoxifen is advantageously administered orally in a dosage of 5 to 50 mg, preferably 10 to 20 mg twice a day, continuing the therapy for sufficient time to achieve and maintain a therapeutic effect. Toremifene is advantageously administered orally in a dosage of about 60 mg once a day, continuing the therapy for sufficient time to achieve and maintain a therapeutic effect. Anastrozole is advantageously administered orally in a dosage of about 1 mg once a day. Droloxifene is advantageously administered orally in a dosage of about 20-100 mg once a day. Raloxifene is advantageously administered orally in a dosage of about 60 mg once a day. Exemestane is advantageously administered orally in a dosage of about 25 mg once a day.

Antibodies are advantageously administered in a dosage of about 1 to 5 mg per square meter ($mg/m^2$) of body surface area, or as known in the art, if different. Trastuzumab is advantageously administered in a dosage of 1 to 5 mg per square meter ($mg/m^2$) of body surface area, particularly 2 to 4 $mg/m^2$ per course of treatment.

EXEMPLIFICATION

The invention will now be described with reference to specific Examples. These are merely exemplary and for illustrative purposes only: they are not intended to be limiting in any way to the scope of the monopoly claimed or to the invention described. These examples constitute the best mode currently contemplated for practicing the invention.

Abbreviations m-CPBA, 3-chloroperoxybenzoic acid; Cu(I)I, copper iodide; DCM, dichloromethane; DIAD, diisopropyl azodicarboxylate; DMF, N,N-dimethylformamide; DMSO, dimethyl sulfoxide; DTT, dithiothreitol; EtOAc, ethyl acetate; HATU, N-[(dimethylamino)-1H-1,2,3-triazolo-[4,5-b]pyridin-1-ylmethylene]-N-methylmethanaminium hexafluorophosphate N-oxide; MeCN, acetonitrile; MeOH, methanol; $MgSO_4$, magnesium sulfate; NaH, sodium hydride; $NaHCO_3$, sodium bicarbonate; NaOH, sodium hydroxide; $Pd(dba)_2$, bis(dibenzylideneacetone) palladium(0); $Pd(PPh_3)_2Cl_2$, bis(triphenylphosphine)palladium(II) dichloride; Petrol, petroleum ether fraction with boiling point range 40-60° C.; TCO, trans-cyclooctene; TCO, trans-cyclooctene; THF, tetrahydrofuran; and Tz thalidomide, tetrazine tagged thalidomide.

ERK2 Bioassay

Activity of ERK2 enzyme (Life Technologies) was determined using a time-resolved fluorescence format measuring the phosphorylation of a truncated version of Activating transcription factor 2 labelled with green fluorescent protein (ATF2-GFP) (Life Technologies). Assay reactions containing 50 mM Tris pH 7.5, 10 mM $MgCl_2$, 1 mM EGTA, 0.01% Triton X-100, 1 mM DTT, 2.5% DMSO, 0.4 µM ATF2-GFP, 20 µM ATP and 0.25 nM ERK2 were set up in the presence of Tz-thalidomide and allowed to proceed for 30 min at room temperature. Reactions were then stopped using TR-FRET dilution buffer (Life Technologies), 25 mM EDTA and 2 nM Tb-Anti-pATF2 (Thr71) (Life Technologies). After a further incubation period of at least 30 minutes, fluorescence was read on a Pherastar reader (Lanthascreen optic module; excitation 340 nm, emission 520 nm (channel A), 495 nm (channel B)). The ratio between A and B counts was used to calculate signal. $IC_{50}$ values were calculated using a sigmoidal dose response equation (Prism GraphPad software, La Jolla, Calif., USA).

Bioorthogonal Reaction In Vitro

The compounds were solubilised in DMSO to generate a 10 mM solution. Pure and mixed samples (TCO ligand: Tz thalidomide 1:1) were then analysed by LC-MS (liquid chromatography mass spectrometry) on a Shimadzu Nexera UPLC coupled with a Shimadzu LCMS-2020 single-quadrupole MS using a YMC-Triart C18 column (50×2.0 mm, 1.9 μm) at 45° C. Gradient elution was performed from 3% acetonitrile to 99% acetonitrile in 10 mmoL ammonium bicarbonate pH 9.4 over 0.7 min.

Cell Culture

HeLa cells (purchased from ATCC) were cultured in Eagle's Minimum Essential Medium (EMEM) supplemented with 10% FBS (Gibco, Life Technologies), 0.1% NEAA (Non-Essential Amino Acid, Gibco, Life Technologies) and 2 mM glutamine and were grown at 37° C. with 5% $CO_2$. A375 and HCT116 cells (purchased from ATCC) were cultured in Dulbecco's Modified Eagle Medium (DMEM) supplemented with 10% FBS (Gibco, Life Technologies) and were grown at 37° C. with 5% $CO_2$.

Immunoblotting

The medium was removed and the cells were washed with PBS (2×). A375 and HCT116 cells were lysed with TG Lysis buffer (150 μL per well) and kept on ice for 20 min. The cell lysates were centrifuged at 14000 rpm for 10 min at 4° C. and the protein concentration was determined by a Pierce™ BCA Protein Assay Kit. Samples were normalised, separated on 4-12% NuPAGE gels (Life Technologies) and transferred onto a nitrocellulose membrane (Novex). The membrane was blocked in blocking buffer (Odyssey) at r.t. for 1 hour and subjected to immunodetection using a total ERK1/2 primary antibody (p44/42 MAPK ERK1/2, Cell Signaling Technologies®, 1:1000) and anti-actin antibody (Abcam ab6276, 1:10000) in blocking buffer, at r.t. for 1 hour. After washing 3× with a Tris-buffered saline (TBS) with 0.1% Tween-20 solution (TBST), the membrane was incubated with fluorescently labelled secondary antibody (IRDye800CW Donkey Anti-Rabbit, 1:10 000 and IRDye680RD Donkey Anti-Mouse, 1:10 000) for 1 hour at r.t. in the dark. After washing 2× with a TBS solution, the membrane was imaged on an Li-Cor Biosciences Odyssey system in the 800 nm and 700 nm channels.

The same procedure was followed with HeLa cells using RIPA Lysis buffer (150 μL per well) and 5% non-fat milk in TBST as blocking buffer. Immunodetection was performed using an anti-BRD4 antibody (Bethyl Laboratories, A301: 985A100, 1:1000) and anti-actin antibody (Abcam ab6276, 1:10000) in 5% non-fat milk in TBST, at 4° C. for 48 hours.

Cell Treatment with Self-Assembling CLIPTACs

HeLa, A375 and HCT116 cells were seeded in 6-well plates at $1.5.10^5$ cells/mL with 2 mL/well and allowed to attach overnight before being incubated with the appropriate compounds. TCO-ligand was added from a 1000× stock in DMSO-$d_6$ (2 μL) to the plates. The cells were incubated at 37° C. in an atmosphere of 5% $CO_2$ and air for 18 hours. Tz-Thalidomide was added from a 1000× stock in DMSO-$d_6$ (2 μL) to the plates. The cells were incubated at 37° C. in an atmosphere of 5% $CO_2$ and air for 18 hours.

When Carfilzomib was used, the compound was added from a 1000× stock in DMSO-$d_6$ (2 μL) 4 hours before the addition of Tz-thalidomide. For control experiments, untagged ligands were added instead of the TCO-compound and methyl-Tz-thalidomide was used instead of Tz-thalidomide. For the time course experiments, the cells were incubated for the indicated time after the addition of Tz-thalidomide and consequently lysed.

Synthetic Methods

Anhydrous solvents were purchased either from VWR or SeccoSolv and were stored under nitrogen. Other solvents were purchased from Fisher Chemicals. Commercially available reagents were used as received. TCO-Amine and TCO-NHS ester were purchased from Jena Bioscience. 'Flash' column chromatography was performed on pre-packed silica cartridges (Biotage SNAP cartridges, KP-Sil) on Biotage Isolera Four. All reactions were carried out under nitrogen.

The purity of the final probes was determined by LC-MS and $^1$H NMR and was always >95%.

NMR Data $^1$H NMR spectra were recorded on a Bruker 400 Ultra-Shield™ spectrometer. Chemical shifts are reported in parts per million (δ) referenced to the appropriate deuterated solvent employed and relative to TMS. Multiplicities are indicated by s (singlet), br s (broad singlet), d (doublet), t (triplet), q (quadruplet), m (multiplet). For NMR data, where the number of protons assigned is less than the theoretical number of protons in the molecule, it is assumed that the apparently missing signal(s) is/are obscured by solvent and/or water peaks.

Analytical LC-MS System

In the following examples, compounds were characterised by mass spectrometry using the systems and operating conditions set out below. Where atoms with different isotopes are present and a single mass quoted, the mass quoted for the compound is the monoisotopic mass (i.e. $^{35}$Cl; $^{79}$Br etc.).

Aqilent 12005L-6140 LC-MS System-RAPID:

HPLC System: Agilent 1200 series SL

Mass Spec Detector: Agilent 6120 or 6140 single quadrupole

Second Detector: Agilent 1200 MWD SL

Agilent MS conditions:

Capillary voltage: 4000V on ES positive (3500 on ES negative)

Fragmentor/Gain: 100

Gain: 1

Drying gas flow: 7.0 L/min

Nebuliser Pressure: 35 psig

Scan Range: 125-800 amu

Ionisation Mode: ElectroSpray Positive-Negative switching

Columns:

A range of commercially available columns—both achiral and chiral—may be used such that, in conjunction with the changes in mobile phase, organic modifier and pH, they enabled the greatest cover in terms of broad range of selectivity. All columns were used in accordance with the manufacturers recommended operating conditions. For example, columns from Waters (including but not limited to Xselect CSH C18, 2.5 μm, 4.6×30 mm; Xbridge BEH C18, 2.5 μm, 4.6×30).

SYNTHESIS OF INTERMEDIATES

Preparation 1: 1,2-Dimethyl 3-hydroxybenzene-1,2-dicarboxylate

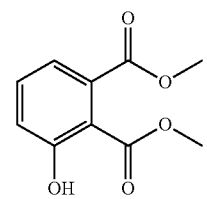

A mixture of 3-hydroxyphtalic anhydride (1.6 g, 9.8 mmol) in MeOH (25 mL) was refluxed for 3 hours. The mixture was cooled to room temperature and concentrated. The residue and NaHCO$_3$ (2.3 g, 27.3 mmol) were stirred in DMF (20 mL). Methyl iodide (1.46 mL, 23.4 mmol) was added and the reaction mixture was heated at 55° C. for 3 hours. The reaction was cooled to room temperature and diluted with EtOAc (80 mL) and water (40 mL). The mixture was acidified with an aqueous solution of HCl (4N) and the aqueous layer was extracted with EtOAc (2×40 mL). The combined organic layers were washed with water (2×100 mL), brine (2×100 mL) and dried over MgSO$_4$. The solvent was removed in vacuo and the crude product was purified by flash column chromatography with 3:7 EtOAc:Petrol to give 1,2-dimethyl 3-hydroxybenzene-1,2-dicarboxylate (1.9 g, 9.1 mmol, 94%) as a pale pink oil. $^1$H NMR (400 MHz, DMSO-d$_6$) δ ppm 10.28 (s, 1H), 7.44-7.30 (m, 2H), 7.17 (dd, J=7.1, 2.2 Hz, 1H), 3.80 (s, 3H), 3.77 (s, 3H). $^{13}$C NMR (101 MHz, DMSO-d$_6$) δ ppm 167.61, 166.10, 155.04, 130.96, 129.04, 122.99, 120.92, 120.42, 52.90, 52.53. LC-MS: [M+H]$^+$=211.

Preparation 2: 1,2-Dimethyl 3-{[6-(tert-butoxy)-6-oxohexyl]oxy}benzene-1,2-dicarboxylate

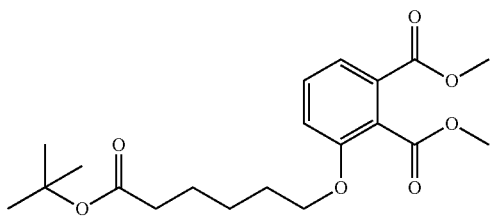 [SMILES: COC(=O)c1cccc(OCCCCCC(=O)OC(C)(C)C)c1C(=O)OC]

To a 0° C. mixture of tert-butyl 6-hydroxyhexanoate (Preparation 1) (0.90 g, 4.76 mmol), triphenylphosphine (0.75 g, 2.86 mmol) and 1,2-dimethyl 3-hydroxybenzene-1,2-dicarboxylate (0.5 g, 2.38 mmol) in THF (4 mL), was added DIAD (0.56 mL, 2.86 mmol) dropwise. The mixture was stirred at room temperature for 18 hours. The solvent was removed in vacuo and the crude product was partitioned between EtOAc (20 mL) and water (20 mL). The organic phase was washed with brine (2×20 mL), dried over MgSO$_4$ and the solvent was removed in vacuo. The crude product was used without further purification. $^1$H NMR (400 MHz, DMSO-d$_6$) δ ppm 7.58-7.45 (m, 2H), 7.40 (dd, J=7.0, 2.3 Hz, 1H), 4.04 (t, J=6.2 Hz, 2H), 3.82 (s, 3H), 3.79 (s, 3H), 2.19 (m, 2H), 1.71-1.62 (m, 2H), 1.58-1.50 (m, 2H), 1.44-1.37 (m, 11H). LC-MS: [M+H]$^+$=381.

Preparation 3: 3-{[6-(tert-Butoxy)-6-oxohexyl]oxy}-2-(methoxycarbonyl)benzoic acid

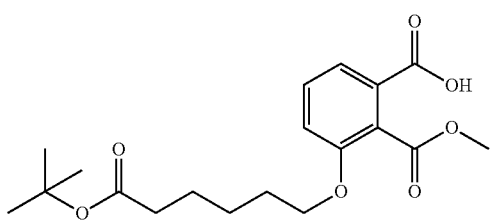 [SMILES: COC(=O)c1c(OCCCCCC(=O)OC(C)(C)C)cccc1C(=O)O]

1,2-Dimethyl 3-{[6-(tert-butoxy)-6-oxohexyl]oxy}benzene-1,2-dicarboxylate (Preparation 2) was solubilised in THF/MeOH (1:1, 15 mL) and NaOH (1M aqueous, 3.03 mL, 3.03 mmol, 3 eq) was added. The resulting solution was stirred at room temperature for 2 hours. The mixture was then acidified to pH 4-5 with a 1M HCl aqueous solution. The organic layer was extracted with DCM. The organic layers were combined, dried over MgSO$_4$ and the solvent was removed in vacuo. The crude product was carried forward without further purification. $^1$H NMR (400 MHz, DMSO-d$_6$) δ ppm 13.23 (br s, 1H), 7.53-7.44 (m, 2H), 7.35 (dd, J=5.2, 4.1 Hz, 1H), 4.03 (t, J=6.1 Hz, 2H), 3.75 (s, 3H), 2.20 (t, J=7.2 Hz, 2H), 1.73-1.61 (m, 2H), 1.61-1.50 (m, 2H), 1.44-1.33 (m, 11H). LC-MS: [M-H]$^-$=365.

Preparation 4: 6-{[2-(2,6-Dioxopiperidin-3-yl)-1,3-dioxo-2,3-dihydro-1H-isoindol-4-yl]oxy}hexanoic acid

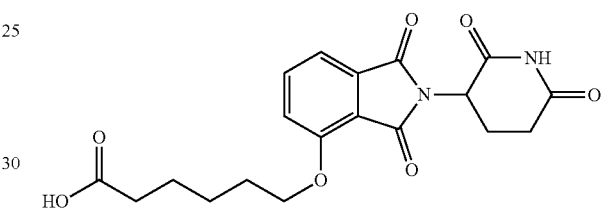

3-{[6-(tert-Butoxy)-6-oxohexyl]oxy}-2-(methoxycarbonyl)benzoic acid (Preparation 3) and 3-aminopiperidine-2,6-dione hydrochloride (0.12 g, 0.75 mmol, 1.1 eq) were dissolved in pyridine (2.7 mL) and heated to 110° C. for 17 hours. The mixture was cooled to room temperature. DCM (20 mL) and a 0.5 M HCl aqueous solution (10 mL) were added. The organic phase was extracted with DCM (3×20 mL). The organic phases were combined, dried over MgSO$_4$ and the solvent was removed in vacuo. The crude product was dissolved in TFA (4 mL) and the mixture was stirred at room temperature for 3 hours. The solvent was removed in vacuo and the crude material was dissolved in DCM (10 mL). The organic phase was extracted with a saturated solution of NaHCO$_3$ (4×20 mL). The aqueous phases were combined and acidified to pH 3 with a 1M HCl aqueous solution. The aqueous phase was then extracted with DCM (4×50 mL). The organic phases were combined, dried over MgSO$_4$ and the solvent was removed in vacuo to give 6-{[2-(2,6-dioxopiperidin-3-yl)-1,3-dioxo-2,3-dihydro-1H-isoindol-4-yl]oxy}hexanoic acid (0.16 g, 0.40 mmol, 58%) as a pale yellow foam. $^1$H NMR (400 MHz, DMSO-d$_6$) δ ppm 11.96 (br s, 1H), 11.08 (s, 1H), 7.81 (dd, J=8.5, 7.2 Hz, 1H), 7.52 (d, J=8.5 Hz, 1H), 7.45 (d, J=7.2 Hz, 1H), 5.08 (dd, J=12.8, 5.4 Hz, 1H), 4.21 (t, J=6.4 Hz, 2H), 2.95-2.82 (m, 1H), 2.64-2.52 (m, 2H), 2.24 (t, J=7.2 Hz, 2H), 2.11-1.96 (m, 1H), 1.83-1.72 (m, 2H), 1.62-1.54 (m, 2H), 1.52-1.42 (m, 2H). $^{13}$C NMR (101 MHz, DMSO-d$_6$) δ ppm 174.84, 173.23, 170.39, 167.30, 165.76, 156.49, 137.49, 133.76, 120.31, 116.74, 115.63, 69.22, 49.24, 34.12, 31.45, 28.66, 25.42, 24.65, 22.49. LC-MS: [M-H]$^-$=387.

Preparation 5: 2-[(9S)-7-(4-Chlorophenyl)-4,5,13-trimethyl-3-thia-1,8,11,12-tetraazatricyclo[8.3.0.0²,⁶]trideca-2(6),4,7,10,12-pentaen-9-yl]acetic acid, TFA salt

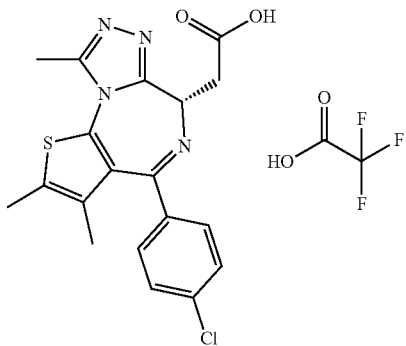 [SMILES: Cc1sc2c(c1C)C(c1ccc(Cl)cc1)=N[C@@H](CC(=O)O)c1nnc(C)n1-2 ; O=C(O)C(F)(F)F]

(+)-JQ-1 (0.10 g, 0.22 mmol) was dissolved in DCM (1.1 mL) and TFA (1.1 mL). The solution was stirred at room temperature for 3 hours. The solvent was removed in vacuo to give 2-[(9S)-7-(4-chlorophenyl)-4,5,13-trimethyl-3-thia-1,8,11,12-tetraazatricyclo[8.3.0.0²,⁶] trideca-2(6),4,7,10,12-pentaen-9-yl]acetic acid, TFA salt (0.11 g, 0.22 mmol, quant.) as a yellow foam which was used without further purification. $^1$H NMR (400 MHz, DMSO-d$_6$) δ ppm 10.12-8.20 (br s, 2H), 7.50 (d, J=8.3 Hz, 2H), 7.45 (d, J=8.3 Hz, 2H), 4.46 (dd, J=7.0, 7.0 Hz, 1H), 3.43 (dd, J=16.7, 7.0 Hz, 1H), 3.34 (dd, J=16.7, 7.0 Hz, 1H), 2.62 (s, 3H), 2.42 (s, 3H), 1.64 (s, 3H). $^{13}$C NMR (101 MHz, DMSO-d$_6$) δ ppm 172.41, 163.69, 158.74 (q, J=39 Hz), 155.27, 150.46, 137.08, 135.81, 132.63, 131.39, 130.66, 130.39, 130.09, 128.98, 115.76 (q, J=288 Hz), 54.03, 36.98, 14.52, 13.16, 11.74. LC-MS: [M+H]$^+$=401.

Preparation 6: 2-[(9R)-7-(4-Chlorophenyl)-4,5,13-trimethyl-3-thia-1,8,11,12-tetraazatricyclo[8.3.0.0²,⁶]trideca-2(6),4,7,10,12-pentaen-9-yl]acetic acid, TFA salt

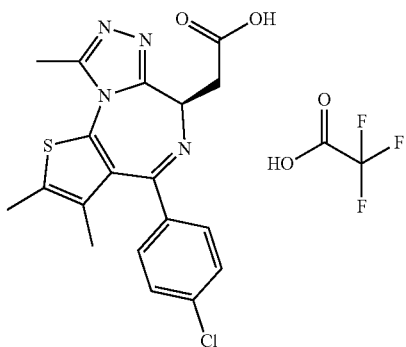 [SMILES: Cc1sc2c(c1C)C(c1ccc(Cl)cc1)=N[C@H](CC(=O)O)c1nnc(C)n1-2 ; O=C(O)C(F)(F)F]

(−)-JQ-1 (0.05 g, 0.11 mmol) was dissolved in DCM (0.6 mL) and TFA (0.6 mL). The solution was stirred at room temperature for 3 hours. The solvent was removed in vacuo to give 2-[(9R)-7-(4-chlorophenyl)-4,5,13-trimethyl-3-thia-1,8,11,12-tetraazatricyclo[8.3.0.0²,⁶] trideca-2(6),4,7,10,12-pentaen-9-yl]acetic acid, TFA salt (0.06 g, 0.11 mmol, quant.) as a yellow foam which was used without further purification. $^1$H NMR (400 MHz, DMSO-d$_6$) δ ppm 7.80-6.85 (br s, 2H), 7.50 (d, J=8.4 Hz, 2H), 7.45 (d, J=8.4 Hz, 2H), 4.46 (dd, J=6.9, 6.9 Hz, 1H), 3.43 (dd, J=16.7, 6.9 Hz, 1H), 3.33 (dd, J=16.7, 6.9 Hz, 1H), 2.62 (s, 3H), 2.42 (s, 3H), 1.64 (s, 3H). $^{13}$C NMR (101 MHz, DMSO-d$_6$) δ ppm 172.40, 163.73, 158.76 (q, J=38 Hz), 155.28, 150.53, 137.06, 135.83, 132.59, 131.44, 130.67, 130.40, 130.12, 128.98, 115.74 (q, J=289 Hz), 54.00, 36.97, 14.50, 13.18, 11.72. LC-MS: [M+H]$^+$=401.

Preparation 7: N1-[5-Chloro-2-(methylsulfanyl)pyrimidin-4-yl]benzene-1,2-diamine

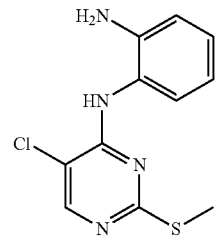 [SMILES: CSc1ncc(Cl)c(Nc2ccccc2N)n1]

N,N-Diisopropylethylamine (0.89 mL, 5.13 mmol) was added to 4,5-dichloro-2-(methylsulfanyl)pyrimidine (0.50 g, 2.56 mmol) and benzene-1,2-diamine (0.28 g, 2.56 mmol) in n-butanol (12 mL). The resulting solution was stirred at 110° C. for 3 hours. The reaction mixture was evaporated and the residue was stirred with aqueous HCl (0.1M, 10 mL) for 30 minutes. The solid was collected by filtration and dried under vacuum. The crude solid was triturated with DCM and filtrated. The filtrate was evaporated to give N1-[5-chloro-2-(methylsulfanyl)pyrimidin-4-yl]benzene-1,2-diamine (0.46 g, 1.73 mmol, 67%) as a pale orange solid. $^1$H NMR (400 MHz, DMSO-d6) δ ppm 8.58 (br s, 1H), 8.18 (s, 1H), 7.08 (dd, J=8.0, 1.5 Hz, 1H), 7.03-6.95 (m, 1H), 6.78 (dd, J=8.0, 1.5 Hz, 1H), 6.62-6.55 (m, 1H), 4.84 (br s, 2H), 2.27 (s, 3H). LC-MS: [M+H]$^+$=267.

Preparation 8: 2-(trimethylsilyl)ethyl N-(2-{[5-chloro-2-(methylsulfanyl) pyrimidin-4-yl]amino}phenyl) carbamate

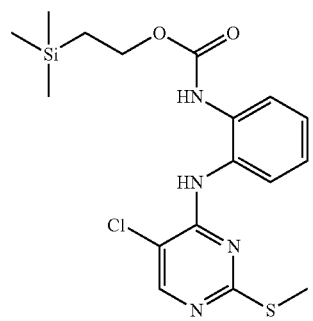

Triethylamine (0.48 mL, 3.46 mmol) and 1-[2-(trimethylsilyl) ethoxycarbonyloxy]pyrrolidin-2,5-dione (0.58 g, 2.26 mmol) were added to a stirred solution of N1-[5-chloro-2-(methylsulfanyl)pyrimidin-4-yl]benzene-1,2-diamine (Preparation 7) (0.46 g, 1.73 mmol) in MeCN/DMF (1:1, 5 mL). The reaction was stirred at 70° C. for 5 hours. The reaction was diluted with EtOAc (20 mL) and washed with a saturated solution of sodium bicarbonate (3×20 mL) and brine (3×20 mL). The organic phase was dried over MgSO$_4$ and the solvent was removed in vacuo. The crude product was purified by flash column chromatography with 3:7 EtOAc:Petrol to give 2-(trimethylsilyl)ethyl N-(2-{[5-chloro-2-(methylsulfanyl) pyrimidin-4-yl)amino]phenyl} carbamate (0.50 g, 1.21 mmol, 80%) as a colourless oil. $^1$H NMR (400 MHz, DMSO-d$_6$) δ ppm 9.13 (br s, 1H), 8.69 (br s, 1H), 8.27 (s, 1H), 7.63-7.54 (m, 1H), 7.44 (m, 1H), 7.27-7.13 (m, 2H), 4.19 (t, J=8.4 Hz, 2H), 2.30 (s, 3H), 1.01 (t, J=8.4 Hz, 2H), 0.03 (s, 9H). LC-MS: [M+H]$^+$=411.

Preparation 9: 2-(Trimethylsilyl)ethyl N-{2-[(5-chloro-2-methanesulfonylpyrimidin-4-yl)amino]phenyl} carbamate

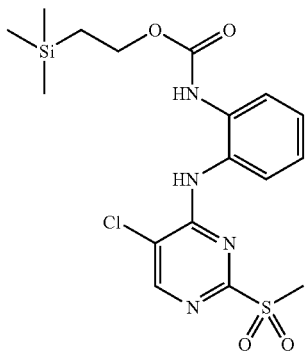

m-CPBA (0.59 g, 2.63 mmol) was added to a solution of N-(2-{[5-chloro-2-(methylsulfanyl)pyrimidin-4-yl]amino}phenyl) carbamate (Preparation 8) (0.49 g, 1.21 mmol) in DCM (24 mL) at 0° C. The reaction was stirred for 2 hours at room temperature. The mixture was washed with a saturated solution of sodium thiosulfate (20 mL) and the organic phase was dried over MgSO$_4$. The solvent was removed in vacuo and the crude was purified by flash column chromatography with 2:3 EtOAc:Petrol to give 2-(trimethylsilyl)ethyl N-{2-[(5-chloro-2-methanesulfonylpyrimidin-4-yl)amino]phenyl} carbamate (0.50 g, 1.13 mmol, 95%) as an orange oil. $^1$H NMR (400 MHz, DMSO-d$_6$) δ ppm 9.33 (br s, 1H), 9.21 (br s, 1H), 8.64 (s, 1H), 7.59-7.49 (m, 2H), 7.32-7.24 (m, 1H), 7.24-7.16 (m, 1H), 4.23-4.13 (m, 2H), 3.14 (s, 3H), 1.04-0.93 (m, 2H), 0.04 (s, 9H). LC-MS: [M+H]$^+$=443.

Preparation 10: 2-(Trimethylsilyl)ethyl N-{2-[(2-amino-5-chloropyrimidin-4-yl)amino]phenyl} carbamate

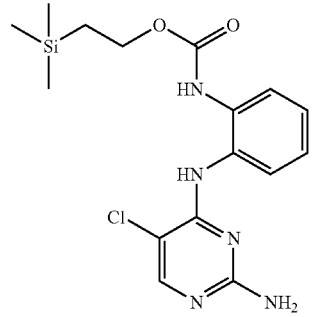 [SMILES: C[Si](C)(C)CCOC(=O)Nc1ccccc1Nc1nc(N)ncc1Cl]

2-(Trimethylsilyl)ethyl N-{2-[(5-chloro-2-methanesulfonylpyrimidin-4-yl)amino]phenyl}carbamate (Preparation 9) (0.45 g, 1.01 mmol) was dissolved in dioxane (1.3 mL) and ammonium hydroxide (5.1 mL) in a 8 mL MW vial. The reaction was sealed and stirred at 80° C. for 20 hours. The reaction was then cooled down, partitioned with EtOAc (10 mL) and water (10 mL). The organic phase was washed with brine (10 mL), dried with MgSO$_4$ and the solvent was removed in vacuo. The crude product was purified by flash column chromatography with 1:9 MeOH:DCM to give 2-(trimethylsilyl)ethyl N-{2-[(2-amino-5-chloropyrimidin-4-yl)amino]phenyl} carbamate (0.22 g, 0.59 mmol, 58%) as a white foam. $^1$H NMR (400 MHz, DMSO-d$_6$) δ ppm 9.00 (br s, 1H), 8.12 (br s, 1H), 7.92 (s, 1H), 7.75-7.68 (m, 1H), 7.35 (dd, J=7.4, 2.1 Hz, 1H), 7.22-7.12 (m, 2H), 6.33 (br s, 2H), 4.19 (t, J=8.2 Hz, 2H), 1.01 (t, J=8.2 Hz, 2H), 0.03 (s, 9H). LC-MS: [M+H]$^+$=380.

Preparation 11: tert-Butyl N-[4-(4-bromopyridin-2-yl)but-3-yn-1-yl]carbamate

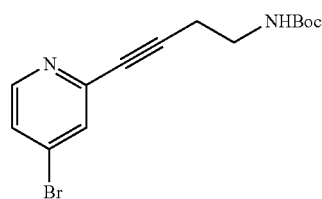 [SMILES: CC(C)(C)OC(=O)NCCC#Cc1cc(Br)ccn1]

2,4-Dibromopyridine (0.50 g, 2.11 mmol), Pd(PPh$_3$)$_2$Cl$_2$ (0.10 g, 0.15 mmol) and Cu(I)I (0.03 g, 0.15 mmol) were solubilised in THF (12 mL). Tert-Butyl but-3-ynylcarbamate (0.39 g, 2.32 mmol) and N,N-diisopropylethylamine (0.74 mL, 4.22 mmol) were added. The resulting suspension was purged with N$_2$ for 15 min. The reaction was stirred at room temperature for 24 hours. The suspension was portioned with a saturated solution of ammonium chloride (20 mL) and EtOAc (20 mL). The organic phase was extracted with EtOAc (3×20 mL), dried over MgSO$_4$ and the solvent was removed in vacuo. The crude product was purified by flash column chromatography with 3:7 EtOAc:Petrol to give tert-butyl N-[4-(4-bromopyridin-2-yl)but-3-yn-1-yl]carbamate (0.33 g, 1.00 mmol, 48%) as an orange solid. $^1$H NMR (400 MHz, DMSO-d$_6$) δ ppm 8.40 (d, J=5.4 Hz, 1H), 7.75 (d, J=2.1 Hz, 1H), 7.64 (dd, J=5.4, 2.1 Hz, 1H), 7.09-6.99 (m, 1H), 3.17 (td, J=6.5 and 6.5 Hz, 2H), 2.57 (t, J=6.5 Hz, 2H), 1.39 (s, 9H). LC-MS: [M+H]$^+$=325.

Preparation 12: tert-Butyl N-(4-{4-[(5-chloro-4-{[2-({[2-(trimethylsilyl)ethoxy]carbonyl}amino) phenyl]amino}pyrimidin-2-yl)amino] pyridin-2-yl}but-3-yn-1-yl)carbamate

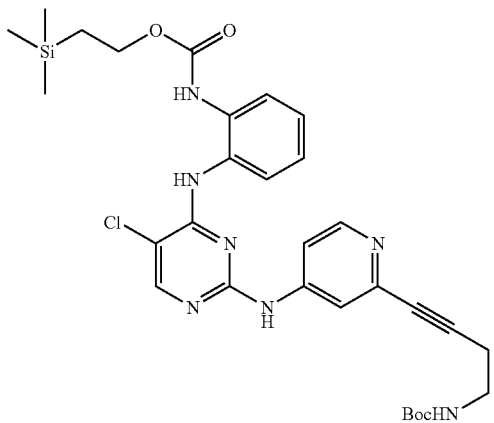 [SMILES: CC(C)(C)OC(=O)NCCC#Cc1cc(Nc2ncc(Cl)c(Nc3ccccc3NC(=O)OCC[Si](C)(C)C)n2)ccn1]

In a round bottom flask fitted with a condenser, tert-butyl N-[4-(4-bromopyridin-2-yl)but-3-yn-1-yl]carbamate (Preparation 11) (0.15 g, 0.46 mmol), 2-(trimethylsilyl)ethyl N-{2-[(2-amino-5-chloropyrimidin-4-yl)amino]phenyl}carbamate (Preparation 10) (0.22 g, 0.59 mmol), potassium carbonate (0.13 g, 0.93 mmol), XPhos (11 mg, 0.02 mmol) and Pd(dba)$_2$ (13 mg, 0.02 mmol) were mixed in MeCN (4.6 mL). The reaction was purged with N$_2$ for 5 min and heated at 80° C. for 18 hours. The crude mixture was filtered and the solvent was removed in vacuo. The crude product was purified by flash column chromatography with 4:1 EtOAc:Petrol to give tert-butyl N-(4-{4-[(5-chloro-4-{[2-({[2-(trimethylsilyl)ethoxy]carbonyl}amino) phenyl]amino}pyrimidin-2-yl)amino]pyridin-2-yl}but-3-yn-1-yl) carbamate (0.12 g, 0.19 mmol, 43%) as an orange oil. $^1$H NMR (400 MHz, DMSO-d$_6$) δ ppm 9.78 (s, 1H), 9.12 (br s, 1H), 8.59 (br s, 1H), 8.25 (s, 1H), 8.06 (d, J=5.7 Hz, 1H), 7.63-7.58 (m, 2H), 7.53-7.47 (m, 1H), 7.41 (dd, J=5.7, 2.3 Hz, 1H), 7.35-7.24 (m, 2H), 7.01 (t, J=6.2 Hz, 1H), 4.18 (t, J=8.3 Hz, 2H), 3.19-3.10 (m, 2H), 2.57-2.52 (m, 2H), 1.39 (s, 9H), 0.99 (t, J=8.3 Hz, 2H), 0.02 (s, 9H). LC-MS: [M+H]$^+$=624.

Preparation 13: tert-Butyl N-{4-[4-({4-[(2-aminophenyl)amino]-5-chloropyrimidin-2-yl}amino)pyridin-2-yl]but-3-yn-1-yl}carbamate

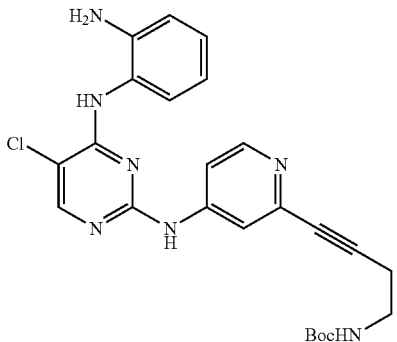 [SMILES: CC(C)(C)OC(=O)NCCC#Cc1cc(Nc2ncc(Cl)c(Nc3ccccc3N)n2)ccn1]

TBAF (1M in THF, 0.5 mL) was added to a stirred solution of tert-butyl N-(4-{4-[(5-chloro-4-{[2-({[2-(trimethylsilyl)ethoxy]carbonyl}amino) phenyl]amino}pyrimidin-2-yl)amino] pyridin-2-yl}but-3-yn-1-yl) carbamate (preparation 12) (0.08 g, 0.12 mmol) in THF (1.25 mL). The reaction was stirred at 40° C. for 2 hours. The reaction was cooled down to room temperature and the solvent was removed in vacuo. The crude residue was dissolved in EtOAc (10 mL) and water (10 mL). The organic phase was extracted with EtOAc (2×10 mL) and DCM (2×10 mL). The organic layers were combined, dried over MgSO$_4$ and the solvent was removed in vacuo. The crude product was purified by flash column chromatography with 1:9 MeOH:DCM to give tert-butyl N-{4-[4-({4-[(2-aminophenyl)amino]-5-chloropyrimidin-2-yl}amino)pyridin-2-yl]but-3-yn-1-yl}carbamate (0.05 g, 0.10 mmol, 83%) as a yellow oil. $^1$H NMR (400 MHz, DMSO-d$_6$) δ ppm 9.68 (br s, 1H), 8.53 (br s, 1H), 8.14 (s, 1H), 7.99-7.94 (m, 1H), 7.52-7.45 (m, 2H), 7.12-7.04 (m, 2H), 7.00 (t, J=6.4 Hz 1H), 6.87-6.81 (m, 1H), 6.68-6.60 (m, 1H), 4.86 (br s, 2H), 3.14 (td, J=6.8 and 6.8 Hz, 2H), 2.59-2.53 (m, 2H), 1.39 (s, 9H). LC-MS: [M+H]$^+$=480.

Preparation 14: (4E)-Cyclooct-4-en-1-yl N-{4-[4-({4-[(2-aminophenyl)amino]-5-chloropyrimidin-2-yl}amino)pyridin-2-yl]but-3-yn-1-yl}carbamate

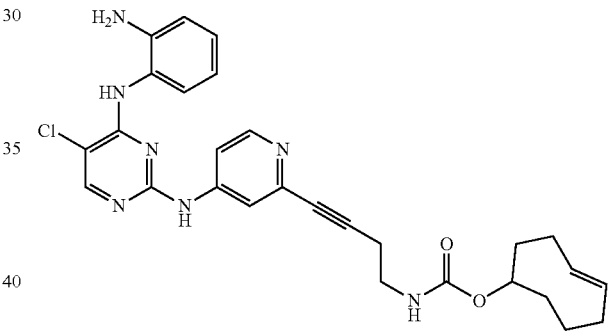

HCl in dioxane (4M, 0.26 mL) was added to a stirred solution of tert-butyl N-{4-[4-({4-[(2-aminophenyl)amino]-5-chloropyrimidin-2-yl}amino)pyridin-2-yl]but-3-yn-1-yl}carbamate (Preparation 13) (0.05 g, 0.10 mmol) in DCM (0.50 mL). As the compound was not soluble, MeOH was added (0.1 mL). The reaction was stirred at room temperature for 18 hours. The solvent was removed in vacuo. The crude product was dissolved in DMF (2.6 mL) and N,N-diisopropylethylamine (45 μL, 0.26 mmol) and TCO-NHS ester (0.03 g, 0.10 mmol) were added. The reaction was stirred at room temperature for 30 min. The solvent was removed in vacuo and the crude was purified by flash column chromatography with EtOAc to give (4E)-cyclooct-4-en-1-yl N-{4-[4-({4-[(2-aminophenyl)amino]-5-chloropyrimidin-2-yl}amino) pyridin-2-yl]but-3-yn-1-yl}carbamate (0.05 g, 0.09 mmol, 91%). $^1$H NMR (400 MHz, DMSO-d$_6$) δ ppm 9.67 (s, 1H), 8.52 (s, 1H), 8.14 (s, 1H), 7.98-7.96 (m, 1H), 7.52-7.44 (m, 2H), 7.16 (t, J=6.9 Hz, 1H), 7.12-7.03 (m, 2H), 6.84 (dd, J=8.0, 1.6 Hz, 1H), 6.68-6.60 (m, 1H), 5.63-5.52 (m, 1H), 5.49-5.38 (m, 1H), 4.86 (s, 2H), 4.27-4.19 (m, 1H), 3.17 (m, 2H), 2.56-2.53 (m, 2H), 2.30-2.23 (m, 3H), 1.96-1.89 (m, 2H), 1.89-1.84 (m, 1H), 1.84-1.79 (m, 1H), 1.68-1.62 (m, 1H), 1.61-1.51 (m, 2H). LC-MS: [M+H]$^+$=532.

Preparation 15: 1,2-Dimethyl 3-[4-(tert-butoxy)-4-oxobutoxy] benzene-1,2-dicarboxylate

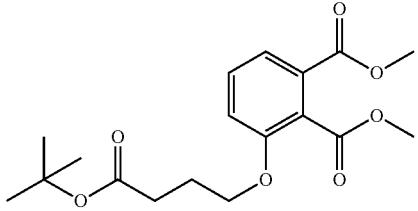 [SMILES: COC(=O)c1cccc(OCCCC(=O)OC(C)(C)C)c1C(=O)OC]

Tert-butyl 4-bromobutanoate (0.81 mL, 4.57 mmol) was added to a suspension of 1,2-dimethyl 3-hydroxybenzene-1,2-dicarboxylate (Preparation 1) (0.80 g, 3.81 mmol) and potassium carbonate (1.58 g, 11.43 mmol) in DMF (15 mL). The reaction was stirred at 50° C. for 18 hours. The solvent was removed in vacuo and the crude product was dissolved in EtOAc. The organic layer was washed with brine (3×) and dried over MgSO$_4$. The solvent was removed in vacuo and the crude product was purified by column chromatography using 1:4 EtOAc:PE to give 1,2-dimethyl 3-[4-(tert-butoxy)-4-oxobutoxy]benzene-1,2-dicarboxylate (1.29 g, 3.66 mmol, 96%) as a pale yellow solid. $^1$H NMR (400 MHz, DMSO-d$_6$) δ ppm 7.58-7.51 (m, 2H), 7.41 (dd, J=7.1, 2.3 Hz, 1H), 4.07 (t, J=6.2 Hz, 2H), 3.82 (s, 3H), 3.80 (s, 3H), 2.33 (t, J=7.4 Hz, 2H), 1.92-1.83 (m, 2H), 1.40 (s, 9H). LCMS: [M+NH$_4$]$^+$=370.

Preparation 16: 3-[4-(Tert-butoxy)-4-oxobutoxy]-2-(methoxycarbonyl)benzoic acid

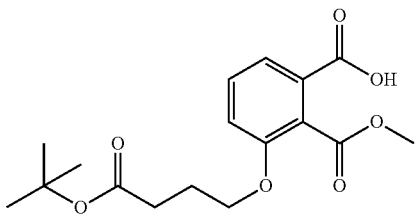 [SMILES: COC(=O)c1c(OCCCC(=O)OC(C)(C)C)cccc1C(=O)O]

NaOH (1M aqueous solution, 11 mL) was added to a stirred solution of 1,2-dimethyl 3-[4-(tert-butoxy)-4-oxobutoxy]benzene-1,2-dicarboxylate (Preparation 15) (1.29 g, 3.66 mmol) in 1:1 THF:MeOH (52 mL). The resulting solution was stirred at r.t. for 2 hours. The mixture was then acidified to pH 4-5 with a 1M HCl aqueous solution. The organic layer was extracted with EtOAc. The organic layers were combined, dried over MgSO$_4$ and the solvent was removed in vacuo. The crude product was purified by column chromatography using 1:1 EtOAc:PE to give 3-[4-(tert-butoxy)-4-oxobutoxy]-2-(methoxycarbonyl)benzoic acid (1.00 g, 2.96 mmol, 81%) as a white solid. $^1$H NMR (400 MHz, DMSO-d$_6$) δ ppm 13.17 (br s, 1H), 7.53-7.49 (m, 2H), 7.35 (dd, J=6.1, 3.2 Hz, 1H), 4.05 (t, J=5.8 Hz, 2H), 3.76 (s, 3H), 2.33 (t, J=7.4 Hz, 2H), 1.91-1.83 (m, 2H), 1.40 (s, 9H). LCMS: =337.

Preparation 17: 4-{[2-(2,6-Dioxopiperidin-3-yl)-1,3-dioxo-2,3-dihydro-1H-isoindol-4-yl]oxy}butanoic acid

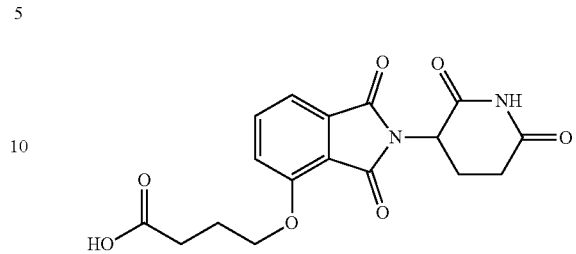

3-[4-(Tert-butoxy)-4-oxobutoxy]-2-(methoxycarbonyl)benzoic acid (Preparation 16) (1.00 g, 2.96 mmol) and 3-aminopiperidine-2,6-dione hydrochloride (0.53 g, 3.25 mmol) were dissolved in pyridine (12 mL) and heated to 110° C. for 17 hours. The mixture was cooled to r.t. DCM (20 mL) and a 0.5 M HCl aqueous solution (20 mL) were added and the organic phase was extracted with DCM (3×). The organic phases were combined, dried over MgSO$_4$ and the solvent was removed in vacuo. The crude product was dissolved in TFA (20 mL) and the mixture was stirred at r.t. for 3 hours. The solvent was removed in vacuo and the crude material was dissolved in DCM (10 mL). The organic phase was extracted with a saturated solution of NaHCO$_3$ (4×20 mL). The aqueous phases were combined and acidified to pH 3 with a 1M HCl aqueous solution. The aqueous phase was then extracted with DCM (4×50 mL). The organic phases were combined, dried over MgSO$_4$ and the solvent was removed in vacuo. The crude product was purified by column chromatography using 1:9 MeOH:DCM to give 4-{[2-(2,6-dioxopiperidin-3-yl)-1,3-dioxo-2,3-dihydro-1H-isoindol-4-yl]oxy}butanoic acid (0.38 g, 1.06 mmol, 36%) as a yellow foam. $^1$H NMR (400 MHz, DMSO-d$_6$) δ ppm 12.40 (br s, 1H), 11.09 (s, 1H), 7.82 (dd, J=8.5, 7.2 Hz, 1H), 7.56-7.49 (m, 2H), 5.09 (dd, J=12.8, 5.3 Hz, 1H), 4.24 (t, J=6.3 Hz, 2H), 2.98-2.81 (m, 1H), 2.62-2.57 (m, 1H), 2.56-2.53 (m, 1H), 2.46 (t, J=7.3 Hz, 2H), 2.09-2.03 (m, 1H), 2.03-1.94 (m, 2H). LCMS: [M+H]$^+$=361.

Preparation 18: 1,2-Dimethyl 3-{[5-(tert-butoxy)-5-oxopentyl]oxy}benzene-1,2-dicarboxylate

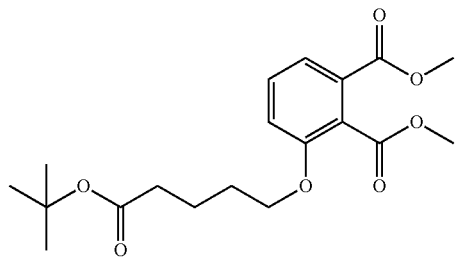

Tert-butyl 5-bromopentanoate (1.08 g, 4.57 mmol) was added to a suspension of 1,2-dimethyl 3-hydroxybenzene-1,2-dicarboxylate (Preparation 1) (0.80 g, 3.81 mmol) and potassium carbonate (1.58 g, 11.43 mmol) in DMF (15 mL). The reaction was stirred at 50° C. for 18 hours. The solvent was removed in vacuo and the crude product was dissolved in DCM (50 mL). Water (50 mL) was added and the mixture was extracted with DCM (3×). The organic phase was then washed with brine (3×) and dried over MgSO₄. The solvent was removed in vacuo and the crude product was purified by column chromatography using 1:1 EtOAc:PE to give 1,2-dimethyl 3-{[5-(tert-butoxy)-5-oxopentyl]oxy} benzene-1,2-dicarboxylate (1.4 g, 3.80 mmol, quant.) as an orange oil. ¹H NMR (400 MHz, DMSO-d₆) δ ppm 7.59-7.49 (m, 2H), 7.40 (dd, J=7.2, 2.2 Hz, 1H), 4.06 (t, J=5.7 Hz, 2H), 3.82 (s, 3H), 3.79 (s, 3H), 2.27-2.21 (m, 2H), 1.72-1.55 (m, 4H), 1.40 (s, 9H). LCMS: [M+H]⁺=367.

Preparation 19: 3-{[5-(Tert-butoxy)-5-oxopentyl]oxy}-2-(methoxycarbonyl)benzoic acid

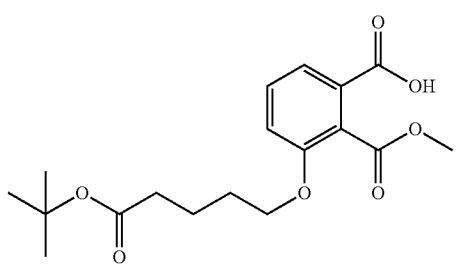

NaOH (1M aqueous solution, 12 mL) was added to a stirred solution of 1,2-dimethyl 3-{[5-(tert-butoxy)-5-oxopentyl]oxy}benzene-1,2-dicarboxylate (Preparation 18) (1.4 g, 3.80 mmol) in 1:1 THF:MeOH (56 mL). The resulting solution was stirred at r.t. for 2 hours. The mixture was then acidified to pH 4-5 with a 1M HCl aqueous solution. The organic layer was extracted with EtOAc. The organic layers were combined, dried over MgSO₄ and the solvent was removed in vacuo. The crude product was purified by column chromatography using 1:1 EtOAc:PE to give 3-{[5-(tert-butoxy)-5-oxopentyl]oxy}-2-(methoxycarbonyl)benzoic acid (1.15 g, 3.27 mmol, 86%) as a colourless oil. ¹H NMR (400 MHz, DMSO-d₆) δ ppm 13.20 (br s, 1H), 7.52-7.48 (m, 2H), 7.35 (dd, J=5.4, 4.0 Hz, 1H), 4.04 (t, J=5.8 Hz, 2H), 3.76 (s, 3H), 2.27-2.21 (m, 2H), 1.72-1.54 (m, 4H), 1.40 (s, 9H). LCMS: =351.

Preparation 20: 5-{[2-(2,6-Dioxopiperidin-3-yl)-1,3-dioxo-2,3-dihydro-1H-isoindol-4-yl]oxy}pentanoic acid

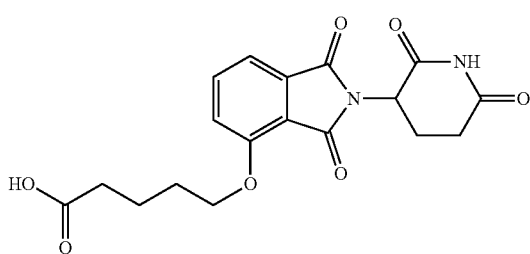

3-{[5-(Tert-butoxy)-5-oxopentyl]oxy}-2-(methoxycarbonyl)benzoic acid (Preparation 19) (0.87 g, 2.47 mmol) and 3-aminopiperidine-2,6-dione hydrochloride (0.45 g, 2.72 mmol) were dissolved in pyridine (10 mL) and heated to 110° C. for 17 hours. The mixture was cooled to r.t. and DCM (20 mL) and a 0.5 M HCl aqueous solution (20 mL) was added. The organic phase was extracted with DCM (3×). The organic phases were combined, dried over MgSO₄ and the solvent was removed in vacuo. The crude product was dissolved in TFA (16.5 mL) and the mixture was stirred at r.t. for 3 hours. The solvent was removed in vacuo and the crude material was dissolved in DCM (10 mL). The organic phase was extracted with a saturated solution of NaHCO₃ (4×20 mL). The aqueous phases were combined and acidified to pH 3 with a 1M HCl aqueous solution. The aqueous phase was then extracted with DCM (4×50 mL). The organic phases were combined, dried over MgSO₄ and the solvent was removed in vacuo to give 5-{[2-(2,6-dioxopiperidin-3-yl)-1,3-dioxo-2,3-dihydro-1H-isoindol-4-yl]oxy}pentanoic acid (0.44 g, 1.17 mmol, 47%) as a yellow solid. ¹H NMR (400 MHz, DMSO-d₆) δ ppm 12.08 (br s, 1H), 11.09 (s, 1H), 7.81 (dd, J=8.6, 7.2 Hz, 1H), 7.52 (d, J=8.6 Hz, 1H), 7.45 (d, J=7.2 Hz, 1H), 5.08 (dd, J=12.7, 5.3 Hz, 1H), 4.22 (t, J=6.1 Hz, 2H), 2.96-2.81 (m, 1H), 2.63-2.57 (m, 1H), 2.55-2.52 (m, 1H), 2.32 (t, J=7.1 Hz, 2H), 2.08-1.98 (m, 1H), 1.84-1.75 (m, 2H), 1.75-1.67 (m, 2H). LCMS: [M−H]⁻=373.

Preparation 21: 7-(Teri-butoxy)-7-oxoheptanoic acid

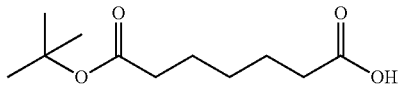

Pimelic acid (1.56 mL, 12.5 mmol), 2-methyl-2-propanol (14.9 mL, 156.3 mmol), EDCl (2.4 g, 12.5 mmol) and DMAP (1.53 g, 12.5 mmol) were dissolved in DCM (15 mL). The reaction was stirred at r.t. for 18 hours. The reaction mixture was diluted with ether (60 mL) and washed with 0.01 N aqueous HCl and water. The organic phase was then dried over MgSO₄ and the solvent was removed in vacuo. The crude product was purified by column chromatography using 1:1 EtOAc:PE to give 7-(tert-butoxy)-7-oxoheptanoic acid (0.52 g, 2.42 mmol, 19%) as a colourless oil. ¹H NMR (400 MHz, DMSO-d₆) δ ppm 12.42 (br s, 1H), 2.18 (q, J=7.4 Hz, 4H), 1.54-1.43 (m, 4H), 1.40 (s, 9H), 1.32-1.22 (m, 2H).

Preparation 22: Tert-butyl 7-hydroxyheptanoate

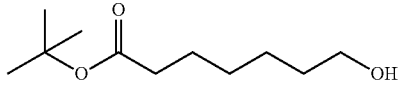

BH₃·Me₂S (2M in THF, 1.33 mL, 2.66 mmol) was added dropwise to a solution of 7-(tert-butoxy)-7-oxoheptanoic acid (Preparation 21) (0.52 g, 2.42 mmol) in dry THF (4 mL) cooled to 0° C. The solution was allowed to warm to r.t. and stirred for 24 hours. EtOAc (20 mL) was added and the organic layer was separated. The organic layer was then washed with water (20 mL) and brine (20 mL), dried over MgSO₄, filtered and the solvent removed in vacuo. The crude product was purified by column chromatography using 2:3 EtOAc:PE to give tert-butyl 7-hydroxyheptanoate (0.46 g, 2.27 mmol, 94%) as a colourless oil. ¹H NMR (400 MHz, DMSO-d₆) δ ppm 4.31 (t, J=5.3 Hz, 1H), 3.37 (dd, J=12.3, 6.3 Hz, 2H), 2.17 (t, J=7.4 Hz, 2H), 1.54-1.44 (m, 2H), 1.44-1.33 (m, 11H), 1.33-1.20 (m, 4H).

Preparation 23: 3-{[7-(Tert-butoxy)-7-oxoheptyl]oxy}-2-(methoxycarbonyl)benzoic acid

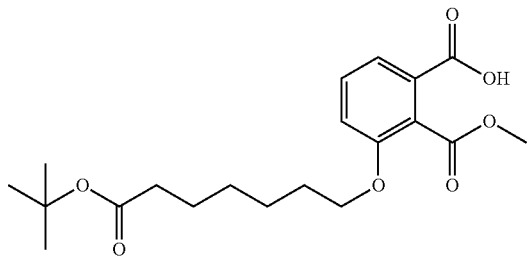 [SMILES: COC(=O)c1c(OCCCCCCC(=O)OC(C)(C)C)cccc1C(=O)O]

To a 0° C. mixture of tert-butyl 7-hydroxyheptanoate (Preparation 22) (0.46 g, 2.27 mmol), triphenylphosphine (0.52 g, 2.0 mmol) and 1,2-dimethyl 3-hydroxybenzene-1,2-dicarboxylate (0.35 g, 1.67 mmol) in THF (3 mL), was added DIAD (0.39 mL, 2.00 mmol) dropwise. The mixture was stirred at r.t. for 18 hours. The solvent was removed in vacuo and the crude product was partitioned between EtOAc (20 mL) and water (20 mL). The organic phase was washed with brine, dried over MgSO$_4$ and the solvent was removed in vacuo. The crude product solubilised in 1:1 THF:MeOH (24 mL). NaOH (1M aqueous solution, 5 mL) was added and the resulting solution was stirred at r.t. for 2 hours. The mixture was then acidified to pH 4-5 with a 1M HCl aqueous solution. The organic layer was extracted with EtOAc. The organic layers were combined, dried over MgSO$_4$ and the solvent was removed in vacuo. The crude product was purified by column chromatography using 1:1 EtOAc:PE to give 3-{[7-(tert-butoxy)-7-oxoheptyl]oxy}-2-(methoxycarbonyl)benzoic acid (0.47 g, 1.24 mmol, 75%) as a colourless oil. $^1$H NMR (400 MHz, DMSO-d$_6$) δ ppm 13.23 (br s, 1H), 7.51-7.47 (m, 2H), 7.35 (dd, J=5.3, 4.0 Hz, 1H), 4.02 (t, J=6.1 Hz, 2H), 3.75 (s, 3H), 2.18 (t, J=7.2 Hz, 2H), 1.70-1.61 (m, 2H), 1.56-1.45 (m, 2H), 1.45-1.35 (m, 2H), 1.34-1.24 (m, 2H). LCMS: [M–H]$^-$=379.

Preparation 24: 7-{[2-(2,6-Dioxopiperidin-3-yl)-1,3-dioxo-2,3-dihydro-1H-isoindol-4-yl]oxy}heptanoic acid

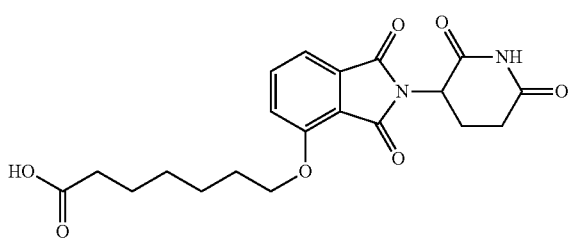 [SMILES: O=C(O)CCCCCCOc1cccc2c1C(=O)N(C1CCC(=O)NC1=O)C2=O]

3-{[7-(Tert-butoxy)-7-oxoheptyl]oxy}-2-(methoxycarbonyl)benzoic acid (Preparation 23) (0.47 g, 1.24 mmol) and 3-aminopiperidine-2,6-dione hydrochloride (0.22 g, 1.36 mmol) were dissolved in pyridine (5 mL) and heated to 110° C. for 17 hours. The mixture was cooled to r.t. DCM (20 mL) and a 0.5 M HCl aqueous solution (20 mL) was added. The organic phase was extracted with DCM (3×). The organic phases were combined, dried over MgSO$_4$ and the solvent was removed in vacuo. The crude product was dissolved in TFA (8 mL) and the mixture was stirred at r.t. for 3 hours. The solvent was removed in vacuo and the crude material was dissolved in DCM (10 mL). The organic phase was extracted with a saturated solution of NaHCO$_3$ (4×20 mL). The aqueous phases were combined and acidified to pH 3 with a 1M HCl aqueous solution. The aqueous phase was then extracted with DCM (4×50 mL). The organic phases were combined, dried over MgSO$_4$ and the solvent was removed in vacuo to give 7-{[2-(2,6-dioxopiperidin-3-yl)-1,3-dioxo-2,3-dihydro-1H-isoindol-4-yl]oxy}heptanoic acid (0.23 g, 0.56 mmol, 45%) as a yellow foam. $^1$H NMR (400 MHz, DMSO-d$_6$) δ ppm 11.99 (br s, 1H), 11.09 (s, 1H), 7.81 (dd, J=8.6, 7.2 Hz, 1H), 7.52 (d, J=8.6 Hz, 1H), 7.44 (d, J=7.2 Hz, 1H), 5.08 (dd, J=12.9, 5.3 Hz, 1H), 4.21 (t, J=6.3 Hz, 2H), 2.95-2.82 (m, 1H), 2.64-2.57 (m, 1H), 2.57-2.53 (m, 1H), 2.22 (t, J=7.3 Hz, 2H), 2.09-1.97 (m, 1H), 1.82-1.71 (m, 2H), 1.58-1.42 (m, 4H), 1.42-1.30 (m, 2H). LCMS: [M–H]$^-$=401.

Preparation 25: 8-(tert-Butoxy)-8-oxooctanoic acid

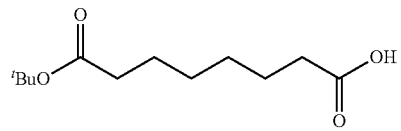 [SMILES: CC(C)(C)OC(=O)CCCCCCC(=O)O]

Octanedioic acid (1.00 g, 5.75 mmol), 2-methyl-2-propanol (6.9 mL, 71.8 mmol), EDCl (1.1 g, 5.74 mmol) and DMAP (0.7 g, 5.74 mmol) were dissolved in DCM (6.8 mL). The reaction was stirred at room temperature for 5 hours. The reaction mixture was diluted with diethyl ether (60 mL) and washed with 0.01N HCl (50 mL) and water (50 mL). The organic phase was then dried over MgSO$_4$ and the solvent was removed in vacuo. The crude product was purified by flash column chromatography with 1:1 EtOAc:Petrol to give 8-(tert-butoxy)-8-oxooctanoic acid (0.41 g, 1.77 mmol, 31%) as colourless oil. $^1$H NMR (400 MHz, DMSO-d$_6$) δ ppm 11.94 (br s, 1H), 2.18 (dd, J=14.6, 7.3 Hz, 4H), 1.54-1.42 (m, 4H), 1.40 (s, 9H), 1.34-1.20 (m, 4H).

Preparation 26: tert-Butyl 8-hydroxyoctanoate

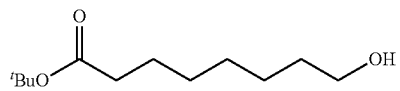 [SMILES: CC(C)(C)OC(=O)CCCCCCCO]

BH$_3$·Me$_2$S in THF (2M, 0.97 mL, 1.95 mmol) was added dropwise to a solution of 8-(tert-butoxy)-8-oxooctanoic acid (Preparation 25) (0.41 g, 1.77 mmol) in THF, cooled to 0° C. The solution was allowed to warm to room temperature and stirred for 24 hours. EtOAc (20 mL) was added and the organic layer separated and washed with water (20 mL) and brine (20 mL), dried over MgSO$_4$ and the solvent removed in vacuo. The crude product was purified by flash column chromatography with 1:4 EtOAc:Petrol to give tert-butyl 8-hydroxyoctanoate (0.28 g, 1.32 mmol, 74%) as colourless oil. $^1$H NMR (400 MHz, DMSO-d$_6$) δ ppm 4.29 (t, J=5.2 Hz, 1H), 3.43-3.33 (m, 2H), 2.17 (t, J=7.3 Hz, 2H), 1.59-1.44 (m, 2H), 1.44-1.36 (m, 11H), 1.31-1.22 (m, 6H).

Preparation 27: 8-{[2-(2,6-Dioxopiperidin-3-yl)-1,3-dioxo-2,3-dihydro-1H-isoindol-4-yl]oxy} octanoic acid

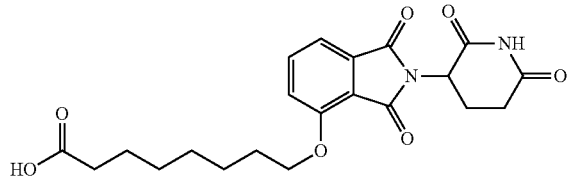 [SMILES: O=C(O)CCCCCCCOc1cccc2c1C(=O)N(C1CCC(=O)NC1=O)C2=O]

To a 0° C. mixture of 1,2-dimethyl 3-hydroxybenzene-1,2-dicarboxylate (0.15 g, 0.71 mmol), triphenylphosphine (0.23 g, 0.86 mmol) and tert-butyl 8-hydroxyoctanoate (Preparation 26) (0.19 g, 0.86 mmol) in THF (1.2 mL), was added DIAD (0.17 mL, 0.86 mmol) dropwise. The mixture was stirred at room temperature for 4 days. The solvent was removed in vacuo and the crude product was partitioned between EtOAc (20 mL) and water (20 mL). The organic phase was washed with brine (20 mL), dried over MgSO$_4$ and the solvent was removed in vacuo. The crude product was purified by flash column chromatography with 1:4 EtOAc:Petrol to give 1,2-dimethyl 3-{[8-(tert-butoxy)-8-oxooctyl]oxy}benzene-1,2-dicarboxylate (0.24 g, 0.59 mmol, 82%) as colourless oil. Not pure after purification. $^1$H NMR (400 MHz, DMSO-d$_6$) δ ppm 7.57-7.47 (m, 2H), 7.40 (dd, J=7.2, 2.0 Hz, 1H), 4.07-4.04 (m, 2H), 3.82 (s, 3H), 3.78 (s, 3H), 2.18 (t, J=7.3 Hz, 2H), 1.71-1.60 (m, 2H), 1.60-1.45 (m, 2H), 1.39 (s, 9H), 1.38-1.33 (m, 2H), 1.32-1.24 (m, 4H). LCMS: [M+H]$^+$=409.

The impure product was used in the next step without further purification. NaOH (1M aqueous, 2.4 mL, 2.4 mmol, 3 eq) was added to a stirred solution of the impure product in THF/MeOH (1:1, 11 mL). The resulting solution was stirred at room temperature for 2 hours. The mixture was then acidified to pH 4-5 with a 1M HCl aqueous solution. The organic layer was extracted with DCM (3×30 mL). The organic layers were combined, dried over MgSO$_4$ and the solvent was removed in vacuo. The crude product was carried forward without further purification. $^1$H NMR (400 MHz, DMSO-d$_6$) δ ppm 13.23 (br s, 1H), 7.53-7.44 (m, 2H), 7.39-7.28 (m, 1H), 4.03 (t, J=6.0 Hz, 2H), 3.75 (s, 3H), 2.18 (t, J=7.3 Hz, 2H), 1.73-1.59 (m, 2H), 1.58-1.44 (m, 2H), 1.39 (s, 9H), 1.38-1.26 (m, 6H). LCMS: [M−H]$^−$=393.

The crude material and 3-aminopiperidine-2,6-dione hydrochloride (0.08 g, 0.48 mmol) were dissolved in pyridine (1.7 mL) and heated to 110° C. for 17 hours. The mixture was cooled to room temperature and DCM (15 mL) and a 0.5 M HCl aqueous solution (8 mL) were added. The organic phase was extracted with DCM (3×20 mL). The organic phases were combined, dried over MgSO$_4$ and the solvent was removed in vacuo. The crude product was dissolved in TFA (2.9 mL) and the mixture was stirred at room temperature for 3 hours. The solvent was removed in vacuo and the crude material was dissolved in DCM (10 mL). The organic phase was extracted with a saturated solution of NaHCO$_3$ (4×20 mL). The aqueous phases were combined and acidified to pH 3 with a 1M HCl aqueous solution. The aqueous phase was then extracted with DCM (4×50 mL). The organic phases were combined, dried over MgSO$_4$ and the solvent was removed in vacuo to give 8-{[2-(2,6-dioxopiperidin-3-yl)-1,3-dioxo-2,3-dihydro-1H-isoindol-4-yl]oxy}octanoic acid (0.11 g, 0.27 mmol, 63%) as a pale yellow foam. $^1$H NMR (400 MHz, DMSO-d$_6$) δ ppm 11.95 (br s, 1H), 11.07 (s, 1H), 7.81 (dd, J=8.6, 7.2 Hz, 1H), 7.52 (d, J=8.6 Hz, 1H), 7.44 (d, J=7.2 Hz, 1H), 5.08 (dd, J=12.8, 5.4 Hz, 1H), 4.21 (t, J=6.3 Hz, 2H), 2.95-2.82 (m, 1H), 2.65-2.52 (m, 2H), 2.20 (t, J=7.3 Hz, 2H), 2.11-1.96 (m, 1H), 1.82-1.71 (m, 2H), 1.56-1.41 (m, 4H), 1.37-1.27 (m, 4H). LCMS: [M−H]$^−$=393.

Example 1: 6-{[2-(2,6-Dioxopiperidin-3-yl)-1,3-dioxo-2,3-dihydro-1H-isoindol-4-yl]oxy}-N-{[4-(6-methyl-1,2,4,5-tetrazin-3-yl)phenyl]methyl}hexanamide

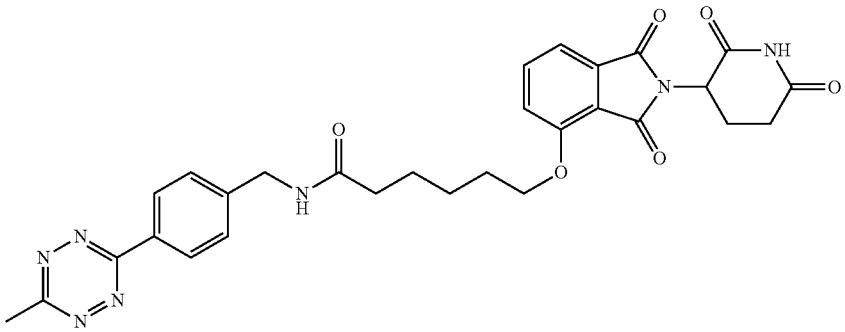 [SMILES: Cc1nnc(-c2ccc(CNC(=O)CCCCCOc3cccc4c3C(=O)N(C3CCC(=O)NC3=O)C4=O)cc2)nn1]

6-{[2-(2,6-Dioxopiperidin-3-yl)-1,3-dioxo-2,3-dihydro-1H-isoindol-4-yl]oxy}hexanoic acid (Preparation 4) (0.16 g, 0.40 mmol), tetrazine amine (0.09 g, 0.4 mmol), DI PEA (0.2 mL, 1.2 mmol) and HATU (0.15 g, 0.40 mmol) were mixed in DMF (4 mL) and the reaction was stirred at room temperature for 2 hours. The reaction was diluted with DCM (20 mL) and washed with brine (3×20 mL). The organic phase was dried over MgSO$_4$ and the solvent was removed in vacuo. The crude product was purified by flash column chromatography with 9:1 EtOAc:Petrol. The compound was then solubilised in MeCN (20 mL) and water (15 mL) and was dried on the freeze dryer to give 6-{[2-(2,6-dioxopiperidin-3-yl)-1,3-dioxo-2,3-dihydro-1H-isoindol-4-yl]oxy}-N-{[4-(6-methyl-1,2,4,5-tetrazin-3-yl)phenyl]methyl}hexanamide (0.13 g, 0.23 mmol, 57%) as a pink solid. $^1$H NMR (400 MHz, DMSO-d$_6$) δ ppm 11.07 (s, 1H), 8.46-8.38 (m, 3H), 7.80 (dd, J=8.6, 7.2 Hz, 1H), 7.55-7.49 (m, 3H), 7.44 (d, J=7.2 Hz, 1H), 5.07 (dd, J=12.7, 5.4 Hz, 1H), 4.40 (d, J=5.8 Hz, 2H), 4.21 (t, J=6.3 Hz, 2H), 3.00 (s, 3H), 2.89-2.82 (m, 1H), 2.63-2.53 (m, 2H), 2.23 (t, J=7.3 Hz, 2H), 2.09-1.98 (m, 1H), 1.84-1.74 (m, 2H), 1.70-1.59 (m, 2H), 1.54-1.43 (m, 2H). $^{13}$C NMR (101 MHz, DMSO-d$_6$) δ ppm 173.20, 172.69, 170.38, 167.52, 167.31, 165.78, 163.67, 156.50, 145.04, 137.48, 133.73, 130.80, 128.52, 127.90, 120.30, 116.73, 115.63, 69.25, 49.23, 42.32, 35.79, 31.44, 28.69, 25.50, 25.46, 22.49, 21.29. LC-MS: [M−H]$^−$=570.

Example 2: N-{[4-(6-Methyl-1,2,4,5-tetrazin-3-yl)phenyl]methyl}-6-{[2-(1-methyl-2,6-dioxo piperidin-3-yl)-1,3-dioxo-2,3-dihydro-1H-isoindol-4-yl]oxy}hexanamide

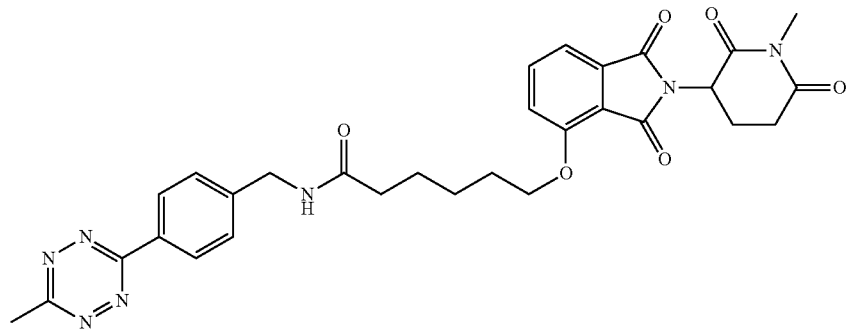 [SMILES: Cc1nnc(-c2ccc(CNC(=O)CCCCCOc3cccc4c3C(=O)N(C3CCC(=O)N(C)C3=O)C4=O)cc2)nn1]

NaH (60% dispersion, 9 mg, 0.23 mmol) was added to a stirred solution of 6-{[2-(2,6-dioxopiperidin-3-yl)-1,3-dioxo-2,3-dihydro-1H-isoindol-4-yl]oxy}-N-{[4-(6-methyl-1,2,4,5-tetrazin-3-yl)phenyl]methyl}hexanamide (Example 1) (50 mg, 0.19 mmol) in dry THF (2 mL) at 0° C. The suspension was stirred at room temperature for 30 min, then methyl iodide (14 μL, 0.23 mmol) was added. The reaction was stirred at room temperature for 18 hours. The reaction was quenched and diluted with water (10 mL). The aqueous phase was extracted with DCM. The combined organic phases were dried over MgSO$_4$ and the solvent was removed in vacuo. The product was purified by flash column chromatography with 100 EtOAc to give N-{[4-(6-Methyl-1,2,4,5-tetrazin-3-yl)phenyl]methyl}-6-{[2-(1-methyl-2,6-dioxo piperidin-3-yl)-1,3-dioxo-2,3-dihydro-1H-isoindol-4-yl]oxy}hexanamide (45 mg, 0.13 mmol, 69%) as a pink solid. $^1$H NMR (400 MHz, DMSO-d$_6$) δ ppm 8.48-8.34 (m, 3H), 7.81 (dd, J=8.8, 7.0 Hz, 1H), 7.59-7.47 (m, 3H), 7.44 (d, J=7.0 Hz, 1H), 5.14 (dd, J=12.9, 5.4 Hz, 1H), 4.39 (d, J=5.9 Hz, 2H), 4.21 (t, J=6.5 Hz, 2H), 3.01 (s, 3H), 3.00 (s, 3H), 2.97-2.87 (m, 1H), 2.81-2.71 (m, 1H), 2.61-2.54 (m, 1H), 2.22 (t, J=7.5 Hz, 2H), 2.09-2.00 (m, 1H), 1.85-1.73 (m, 2H), 1.70-1.60 (m, 2H), 1.54-1.43 (m, 2H). $^{13}$C NMR (101 MHz, DMSO-d$_6$) δ ppm 172.69, 172.21, 170.13, 167.51, 167.28, 165.77, 163.66, 156.53, 145.04, 137.51, 133.71, 130.79, 128.52, 127.89, 120.31, 116.70, 115.63, 69.24, 49.79, 42.31, 35.7, 31.57, 28.68, 27.05, 25.49, 25.44, 21.68, 21.27. LC-MS: [M−H]$^-$=584.2.

Example 3: (4E)-Cyclooct-4-en-1-yl N-(3-{2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]acetamido}propyl)carbamate

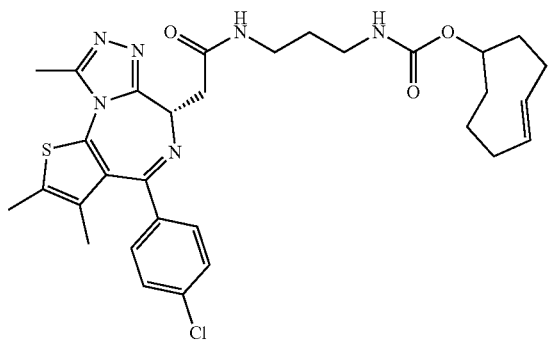 [SMILES: Cc1sc2c(c1C)C(c1ccc(Cl)cc1)=N[C@@H](CC(=O)NCCCNC(=O)OC1CC/C=C/CCC1)c1nnc(C)n1-2]

2-[(9S)-7-(4-Chlorophenyl)-4,5,13-trimethyl-3-thia-1,8,11,12-tetraazatricyclo[8.3.0.0$^{2,6}$] trideca-2(6),4,7,10,12-pentaen-9-yl]acetic acid. TFA salt (Preparation 5) (40 mg, 0.08 mmol), N,N-diisopropylethylamine (41 μL, 0.23 mmol), HATU (30 mg, 0.08 mmol) and TCO-amine (18 mg, 0.08 mmol) were mixed in DMF (1 mL) and the reaction was stirred at room temperature for 16 hours. The solvent was removed in vacuo and the crude product was solubilised in diethyl ether (10 mL) and washed with a cold saturated solution of NaHCO$_3$ (3×10 mL). The organic phase was dried over MgSO$_4$ and the solvent was removed in vacuo. The crude product was purified by flash column chromatography with 1:9 MeOH:DCM to give (4E)-cyclooct-4-en-1-yl N-(3-{2-[(9S)-7-(4-chlorophenyl)-4,5,13-trimethyl-3-thia-1,8,11,12-tetraazatricyclo[8.3.0.0$^{2,6}$]trideca-2 (6), 4,7, 10,12-pentaen-9-yl]acetamido}propyl) carbamate (33 mg, 0.05 mmol, 70%) as a white solid. $^1$H NMR (400 MHz, CDCl$_3$) δ ppm 7.41 (d, J=8.2 Hz, 2H), 7.35 (d, J=8.2 Hz, 2H), 6.98 (t, J=6.9 Hz, 1H), 5.66-5.46 (m, 2H), 5.40-5.32 (m, 1H), 4.66 (dd, J=6.8 Hz, 1H), 4.41-4.29 (m, 1H), 3.56 (ddd, J=14.4 Hz, 7.5 Hz, 2.1 Hz, 1H), 3.46-3.32 (m, 3H), 3.24-3.12 (m, 2H), 2.70 (s, 3H), 2.43 (s, 3H), 2.41-2.31 (m, 3H), 2.06-2.00 (m, 1H), 2.00-1.88 (m, 3H), 1.80-1.66 (m, 7H), 1.59-1.51 (m, 1H). $^{13}$C NMR (101 MHz, CDCl$_3$) δ ppm 170.97, 163.87, 156.46, 155.91, 149.82, 136.80, 136.58, 134.90, 132.93, 130.88, 129.82, 128.70, 80.49, 54.42, 41.40, 39.24, 38.96, 37.36, 36.23, 34.21, 32.52, 30.92, 29.94, 14.29, 13.02, 11.56. LC-MS: [M+H]$^+$=609.

Example 4: (4E)-Cyclooct-4-en-1-yl N-(3-{2-[(9R)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]acetamido}propyl)carbamate

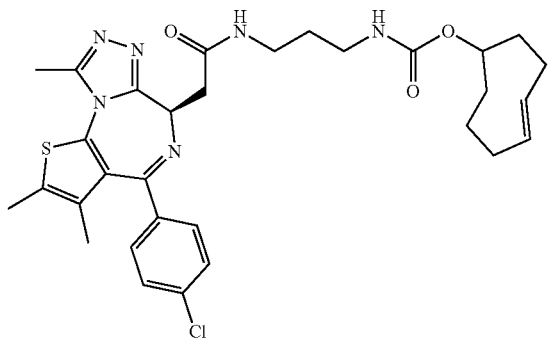 [SMILES: Cc1sc2c(c1C)C(c1ccc(Cl)cc1)=N[C@H](CC(=O)NCCCNC(=O)OC1CC/C=C/CCC1)c1nnc(C)n1-2]

2-[(9R)-7-(4-Chlorophenyl)-4,5,13-trimethyl-3-thia-1,8,11,12-tetraazatricyclo[8.3.0.0$^{2,6}$] trideca-2(6),4,7,10,12-pentaen-9-yl]acetic acid. TFA salt (Preparation 6) (40 mg, 0.08 mmol), N,N-diisopropylethylamine (41 µL, 0.23 mmol), HATU (30 mg, 0.08 mmol) and TCO-amine (18 mg, 0.08 mmol) were mixed in DMF (1 mL) and the reaction was stirred at room temperature for 16 hours. The solvent was removed in vacuo and the crude product was solubilised in diethyl ether (10 mL) and washed with a cold saturated solution of NaHCO$_3$ (3×10 mL). The organic phase was dried over MgSO$_4$ and the solvent was removed in vacuo. The crude product was purified by flash column chromatography with 1:9 MeOH:DCM to give (4E)-cyclooct-4-en-1-yl N-(3-{2-[(9R)-7-(4-chlorophenyl)-4,5,13-trimethyl-3-thia-1,8,11,12-tetraazatricyclo[8.3.0.0$^{2,6}$]trideca-2(6), 4,7, 10,12-pentaen-9-yl]acetamido}propyl)carbamate (23 mg, 0.04 mmol, 48%) as a pale yellow solid. $^1$H NMR (400 MHz, DMSO-d$_6$) δ ppm 8.16 (t, J=5.3 Hz, 1H), 7.49 (d, J=8.5 Hz, 2H), 7.42 (d, J=8.5 Hz, 2H), 6.92-6.89 (m, 1H), 5.62-5.54 (m, 1H), 5.47-5.40 (m, 1H), 4.50 (dd, J=8.5, 5.7 Hz, 1H), 4.24-4.19 (m, 1H), 3.27-3.24 (m, 1H), 3.20-3.13 (m, 2H), 3.08-2.98 (m, 3H), 2.60 (s, 3H), 2.42 (s, 3H), 2.29-2.21 (m, 3H), 1.94-1.80 (m, 4H), 1.67-1.60 (m, 4H), 1.59-1.52 (m, 4H). $^{13}$C NMR (101 MHz, DMSO-d$_6$) δ ppm 169.94, 163.43, 155.54, 151.90, 150.51, 137.22, 135.70, 135.31, 132.91, 130.92, 130.69, 130.46, 128.99, 79.42, 54.41, 41.20, 38.68, 38.46, 38.12, 36.72, 34.22, 32.70, 31.11, 30.04, 14.54, 13.17, 11.80. LC-MS: [M+H]$^+$=609.

Example 5: (4E)-Cyclooct-4-en-1-yl N-(4-{4-[(5-chloro-4-{[2-(prop-2-enamido)phenyl]amino}pyrimidin-2-yl)amino]pyridin-2-yl}but-3-yn-1-yl) carbamate

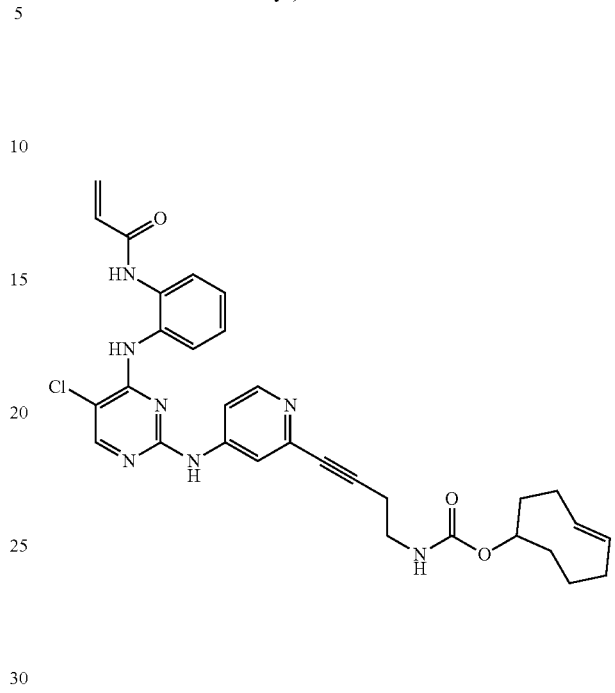

A solution of acryloyl chloride (8 µL, 0.1 mmol) in THF (0.2 mL) was added to a stirred solution of (4E)-cyclooct-4-en-1-yl N-{4-[4-({4-[(2-aminophenyl)amino]-5-chloropyrimidin-2-yl}amino)pyridin-2-yl]but-3-yn-1-yl}carbamate (Preparation 14) (0.05 g, 0.09 mmol) and N,N-diisopropylethylamine (41 µL, 0.24 mmol) in THF at 0° C. The reaction was stirred at 0° C. for 30 minutes. The solvent was removed in vacuo and the crude was purified by flash column chromatography with EtOAc to give (4E)-cyclooct-4-en-1-yl N-(4-{4-[(5-chloro-4-{[2-(prop-2-enamido)phenyl] amino}pyrimidin-2-yl)amino]pyridin-2-yl}but-3-yn-1-yl) carbamate (24 mg, 0.04 mmol, 44%) as an off white solid. $^1$H NMR (400 MHz, DMSO-d$_6$) δ ppm 10.19 (s, 1H), 9.82 (s, 1H), 8.72 (s, 1H), 8.24 (s, 1H), 8.08 (d, J=5.8 Hz, 1H), 7.70 (d, J=7.8 Hz, 1H), 7.63 (s, 1H), 7.52 (d, J=7.7 Hz, 1H), 7.44-7.38 (m, 1H), 7.38-7.29 (m, 2H), 7.21 (t, J=6.0 Hz, 1H), 6.51 (dd, J=17.0, 10.2 Hz, 1H), 6.38-6.26 (m, 1H), 5.80 (d, J=10.1 Hz, 1H), 5.56 (ddd, J=15.4, 10.4, 4.4 Hz, 1H), 5.43 (ddd, J=15.6, 11.0, 3.6 Hz, 1H), 4.22 (dt, J=9.0, 4.5 Hz, 1H), 3.25-3.08 (m, 2H), 2.54 (t, J=6.9 Hz, 2H), 2.33-2.15 (m, 3H), 1.99-1.88 (m, 2H), 1.88-1.84 (m, 1H), 1.85-1.78 (m, 1H), 1.71-1.56 (m, 2H), 1.56-1.46 (m, 1H). $^{13}$C NMR (101 MHz, DMSO-d$_6$) δ ppm 164.19, 157.11, 156.42, 155.67, 154.26, 149.45, 147.15, 142.75, 134.75, 132.39, 131.64, 131.12, 130.84, 127.64, 127.12, 125.69, 124.32, 114.80, 111.55, 106.00, 86.58, 81.71, 79.02, 40.47, 39.08, 37.98, 33.53, 31.92, 30.32, 19.76. HRMS m/z calc. for C$_{31}$H$_{32}$ClN$_7$O$_3$ [M+H]$^+$ 586.2328; found 586.2324.

Example 6: 4-{[2-(2,6-Dioxopiperidin-3-yl)-1,3-dioxo-2,3-dihydro-1H-isoindol-4-yl]oxy}-N-{[4-(6-methyl-1,2,4,5-tetrazin-3-yl)phenyl]methyl}butanamide

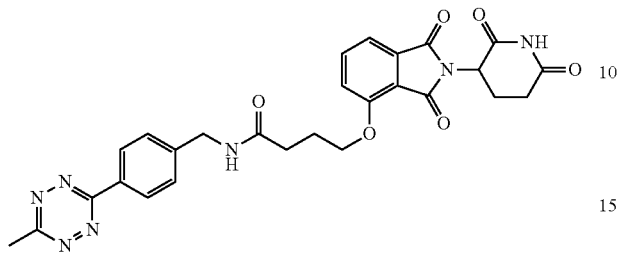

4-{[2-(2,6-Dioxopiperidin-3-yl)-1,3-dioxo-2,3-dihydro-1H-isoindol-4-yl]oxy}butanoic acid (0.15 g, 0.42 mmol) (Preparation 17), [4-(6-methyl-1,2,4,5-tetrazin-3-yl)phenyl]methanamine (0.09 g, 0.42 mmol), HATU (0.16 g, 0.42 mmol) and N,N-diisopropylethylamine (0.22 mL, 1.25 mmol) were mixed in DMF (4 mL) and the reaction was stirred at r.t. for 1 hour. The reaction was diluted with DCM (10 mL) and washed with brine (3×). The organic phase was dried over MgSO₄ and the solvent was removed in vacuo. The crude product was purified by column chromatography using 100EtOAc to give 4-{[2-(2,6-dioxopiperidin-3-yl)-1,3-dioxo-2,3-dihydro-1H-isoindol-4-yl]oxy}-N-{[4-(6-methyl-1,2,4,5-tetrazin-3-yl)phenyl]methyl}butanamide (0.06 g, 0.11 mmol, 27%) as a pink solid. $^1$H NMR (400 MHz, DMSO-$d_6$) δ ppm 11.09 (s, 1H), 8.52 (t, J=6.0 Hz, 1H), 8.41 (d, J=7.9 Hz, 2H), 7.81 (dd, J=8.7, 7.1 Hz, 1H), 7.56-7.50 (m, 3H), 7.45 (d, J=7.1 Hz, 1H), 5.08 (dd, J=12.7, 5.3 Hz, 1H), 4.41 (d, J=5.9 Hz, 2H), 4.25 (t, J=6.3 Hz, 2H), 3.00 (s, 3H), 2.95-2.83 (m, 1H), 2.62-2.58 (m, 1H), 2.55-2.52 (m, 1H), 2.44 (t, J=7.4 Hz, 2H), 2.05 (m, 3H). $^{13}$C NMR (101 MHz, DMSO-$d_6$) δ ppm 173.1, 172.0, 170.3, 167.3, 167.2, 165.5, 163.5, 156.0, 146.9, 137.6, 134.3, 130.7, 128.6, 128.6, 127.8, 127.8, 120.2, 116.8, 115.7, 68.7, 49.3, 42.1, 31.6, 31.4, 24.9, 22.3, 21.4. LCMS: [M+H]$^+$=544.2.

Example 7: 5-{[2-(2,6-Dioxopiperidin-3-yl)-1,3-dioxo-2,3-dihydro-1H-isoindol-4-yl]oxy}-N-{[4-(6-methyl-1,2,4,5-tetrazin-3-yl)phenyl]methyl}pentanamide

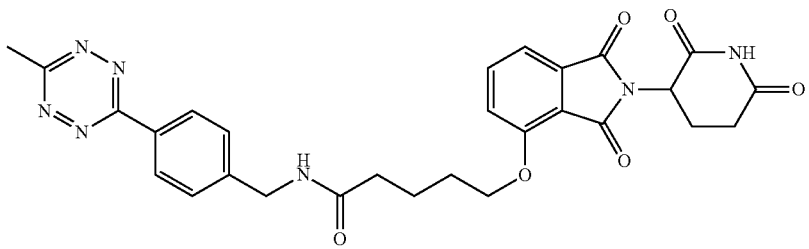 [SMILES: Cc1nnc(-c2ccc(CNC(=O)CCCCOc3cccc4c3C(=O)N(C3CCC(=O)NC3=O)C4=O)cc2)nn1]

5-{[2-(2,6-Dioxopiperidin-3-yl)-1,3-dioxo-2,3-dihydro-1H-isoindol-4-yl]oxy}pentanoic acid (Preparation 20) (0.10 g, 0.27 mmol), [4-(6-methyl-1,2,4,5-tetrazin-3-yl)phenyl]methanamine (0.06 g, 0.27 mmol), HATU (0.10 g, 0.27 mmol) and N,N-diisopropylethylamine (0.14 mL, 0.80 mmol) were mixed in DMF (3 mL) and the reaction was stirred at r.t. for 1 hour. The reaction was diluted with DCM (10 mL) and washed with brine (3×). The organic phase was dried over MgSO₄ and the solvent was removed in vacuo. The crude product was purified by column chromatography using 100 EtOAc to give 5-{[2-(2,6-dioxopiperidin-3-yl)-1,3-dioxo-2,3-dihydro-1H-isoindol-4-yl]oxy}-N-{[4-(6-methyl-1,2,4,5-tetrazin-3-yl)phenyl]methyl}pentanamide (0.07 g, 0.13 mmol, 48%) as a pink solid. $^1$H NMR (400 MHz, DMSO-$d_6$) δ ppm 11.08 (s, 1H), 8.47 (t, J=6.1 Hz, 1H), 8.42 (d, J=8.0 Hz, 2H), 7.81 (dd, J=8.5, 7.2 Hz, 1H), 7.55-7.50 (m, 3H), 7.44 (d, J=7.2 Hz, 1H), 5.08 (dd, J=12.9, 5.3 Hz, 1H), 4.41 (d, J=5.9 Hz, 2H), 4.24 (t, J=5.8 Hz, 2H), 3.00 (s, 3H), 2.95-2.82 (m, 1H), 2.62-2.57 (m, 1H), 2.56-2.52 (m, 1H), 2.29 (t, J=6.6 Hz, 2H), 2.09-2.00 (m, 1H), 1.84-1.73 (m, 4H). $^{13}$C NMR (101 MHz, DMSO-$d_6$) δ ppm 172.4, 170.6, 170.3, 167.4, 167.2, 165.5, 163.5, 156.3, 145.0, 137.4, 133.5, 130.8, 128.8, 128.4, 127.9, 127.9, 120.2, 116.0, 115.5, 69.0, 49.1, 42.3, 35.3, 31.4, 28.4, 22.3, 22.1, 21.1. LCMS: [M+H]$^+$=558.2.

Example 8: 7-{[2-(2,6-Dioxopiperidin-3-yl)-1,3-dioxo-2,3-dihydro-1H-isoindol-4-yl]oxy}-N-{[4-(6-methyl-1,2,4,5-tetrazin-3-yl)phenyl]methyl}heptanamide

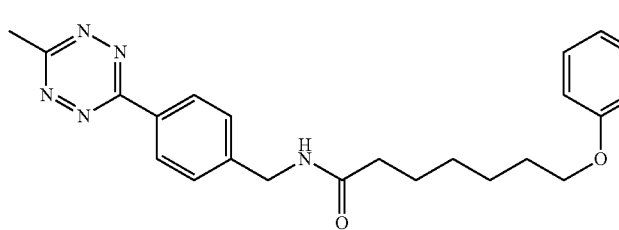

7-{[2-(2,6-dioxopiperidin-3-yl)-1,3-dioxo-2,3-dihydro-1H-isoindol-4-yl]oxy}heptanoic acid (Preparation 24) (0.10 g, 0.25 mmol), [4-(6-methyl-1,2,4,5-tetrazin-3-yl)phenyl]methanamine (0.06 g, 0.25 mmol), HATU (0.10 g, 0.25 mmol) and N,N-diisopropylethylamine (0.13 mL, 0.75 mmol) were mixed in DMF (3 mL) and the reaction was stirred at r.t. for 1 hour. The reaction was diluted with DCM (10 mL) and washed with brine (3×). The organic phase was dried over MgSO$_4$ and the solvent was removed in vacuo. The crude product was purified by column chromatography using 100 EtOAc to give 7-{[2-(2,6-dioxopiperidin-3-yl)-1,3-dioxo-2,3-dihydro-1H-isoindol-4-yl]oxy}-N-{[4-(6-methyl-1,2,4,5-tetrazin-3-yl)phenyl]methyl}heptanamide (0.06 g, 0.06 mmol, 38%) as a pink solid. $^1$H NMR (400 MHz, DMSO-d$_6$) δ ppm 11.09 (s, 1H), 8.46-8.38 (m, 3H), 7.80 (dd, J=8.5, 7.1 Hz, 1H), 7.56-7.47 (m, 3H), 7.44 (d, J=7.3 Hz, 1H), 5.08 (dd, J=12.7, 5.3 Hz, 1H), 4.39 (d, J=5.9 Hz, 2H), 4.20 (t, J=6.4 Hz, 2H), 2.99 (s, 3H), 2.95-2.82 (m, 1H), 2.64-2.57 (m, 1H), 2.57-2.53 (m, 1H), 2.20 (t, J=7.4 Hz, 2H), 2.08-2.00 (m, 1H), 1.82-1.71 (m, 2H), 1.65-1.53 (m, 2H), 1.53-1.42 (m, 2H), 1.42-1.32 (m, 2H). $^{13}$C NMR (101 MHz, DMSO-d$_6$) δ ppm 173.2, 172.3, 170.4, 167.4, 167.2, 165.5, 163.4, 156.3, 144.8, 137.5, 133.5, 130.6, 128.5, 128.5, 127.9, 127.9, 120.2, 116.5, 115.6, 69.2, 49.2, 42.2, 35.9, 31.3, 28.8, 28.7, 25.7, 25.5, 22.4, 21.3. LCMS: [M+H]$^+$=586.2.

Example 9: 8-{[2-(2,6-Dioxopiperidin-3-yl)-1,3-dioxo-2,3-dihydro-1H-isoindol-4-yl]oxy}-N-{[4-(6-methyl-1,2,4,5-tetrazin-3-yl)phenyl]methyl}octanamide 8-{[2-(2,6-Dioxopiperidin-3-yl)-1,3-dioxo-2,3-dihydro-1H-isoindol-4-yl]oxy}octanoic acid (Preparation 27) (0.11 g, 0.27 mmol), [4-(6-methyl-1,2,4,5-tetrazin-3-yl)phenyl]methanamine (0.06 g, 0.27 mmol), DIPEA (0.14 mL, 0.81 mmol) and HATU (0.10 g, 0.27 mmol) were mixed in DMF (2.7 mL) and the reaction was stirred at room temperature for 2 hours. The reaction was diluted with DCM (20 mL) and washed with brine (3×20 mL). The organic phase was dried over MgSO$_4$ and the solvent was removed in vacuo. The crude product was purified by flash column chromatography with 4:1 EtOAc:Petrol. The compound was then solubilised in MeCN (20 mL) and water (15 mL) and was dried on the freeze dryer to give 8-{[2-(2,6-dioxopiperidin-3-yl)-1,3-dioxo-2,3-dihydro-1H-isoindol-4-yl]oxy}-N-{[4-(6-methyl-1,2,4,5-tetrazin-3-yl)phenyl]methyl}octanamide (0.08 g, 0.12 mmol, 46%) as a pink solid. $^1$H NMR (400 MHz, DMSO-d$_6$) δ ppm 11.07 (s, 1H), 8.45-8.37 (m, 3H), 7.80 (dd, J=8.6, 7.3 Hz, 1H), 7.55-7.47 (m, 3H), 7.44 (d, J=7.3 Hz, 1H), 5.07 (dd, J=12.9, 5.4 Hz, 1H), 4.39 (d, J=5.9 Hz, 2H), 4.20 (t, J=6.4 Hz, 2H), 2.99 (s, 3H), 2.94-2.82 (m, 1H), 2.63-2.53 (m, 2H), 2.19 (t, J=7.4 Hz, 2H), 2.06-1.99 (m, 1H), 1.80-1.72 (m, 2H), 1.60-1.53 (m, 2H), 1.50-1.42 (m, 2H), 1.39-1.29 (m, 4H). LCMS: =598.

FIGURE LEGENDS

FIG. 1: Schematic illustration of CLIPTACs.

FIG. 2: LC-MS profile of the click reaction between JQ1-TCO and Tz-thalidomide. LC-MS analysis of JQ1-TCO (right hand peak), Tz-thalidomide (left hand peak) and the reaction mixture after 15 min (middle peak).

FIG. 3: (a) Affinity of JQ1 (n=1), JQ1-TCO (n=2), JQ1-CLICK (n=2) and (−)JQ1-TCO (n=2) for BRD4-1 and BRD4-2 as determined by AlphaScreen histone peptide displacement assays. (b) Selectivity of JQ1-TCO (10 μM, duplicate, thermal shift) across the bromodomain family. (c) Immunoblot for BRD4 and Actin showing JQ1-TCO concentration dependent downregulation of BRD4 protein lev-

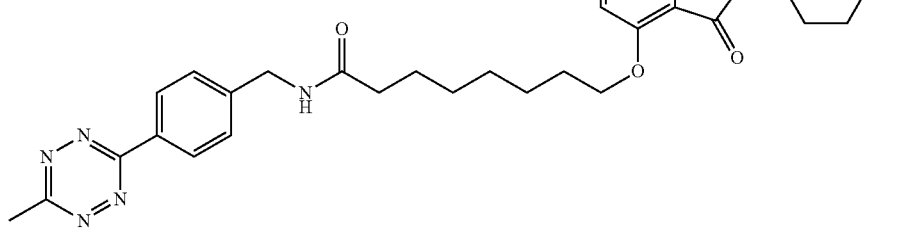

els. HeLa cells were treated with JQ1-TCO for 18 hours followed by treatment with Tz-thalidomide (10 μM) for 18 hours. (d) Immunoblot for BRD4 and Actin showing Tz-thalidomide concentration dependent downregulation of BRD4 protein levels. HeLa cells were treated with JQ1-TCO (10 μM) for 18 hours followed by treatment with Tz-thalidomide for 18 hours. (e) Immunoblot for BRD4 and Actin showing time-dependent downregulation of BRD4 protein levels. HeLa cells were treated with JQ1-TCO (10 μM) for 18 hours followed by treatment with Tz-thalidomide (10 μM) for the indicated time. (f) Immunoblot for BRD4 and Actin showing no BRD4 degradation when the interaction between JQ1 and BRD4 is perturbed. HeLa cells were treated with (−)JQ1-TCO for 18 hours followed by treatment with Tz-thalidomide for 18 hours. (g) Immunoblot for BRD4 and Actin showing no BRD4 degradation when the interaction between thalidomide and CRBN is perturbed. HeLa cells were treated with JQ1-TCO for 18 hours followed by treatment with Methyl-Tz-thalidomide for 18 hours. (h) Immunoblot for BRD4 and Actin showing the effects of JQ1-TCO and Tz-thalidomide alone, the effects of preventing the click reaction using JQ1 and the effects of a 4-hour pre-treatment with Carfilzomib (1 μM) on BRD4 protein levels. Experiments performed on HeLa cells.

FIG. 4: Biological evaluation of Tz-thalidomide against both domains of BRD4, BRD4-1 and BRD4-2. Biological evaluation of Tz-thalidomide (n=2) by AlphaScreen (performed by Reaction Biology).

Figure 5:
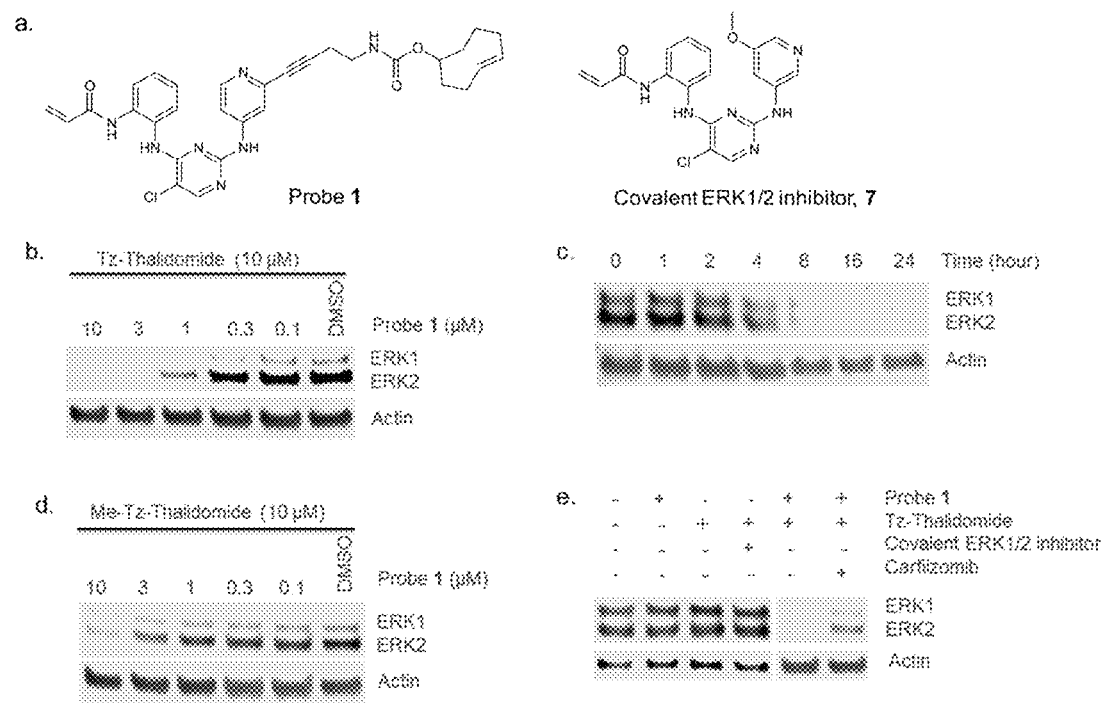
Figure 6:
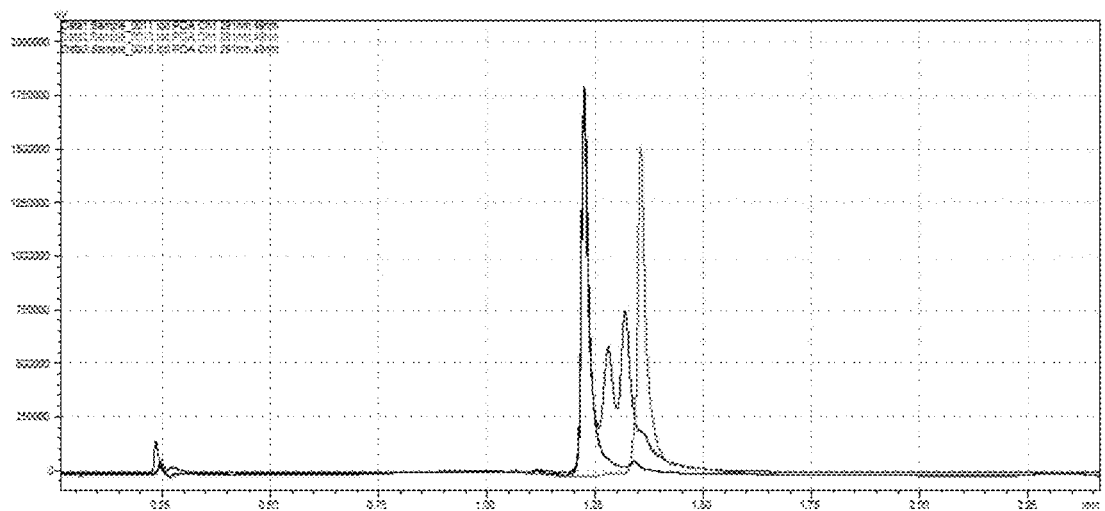

FIG. 5: (a) Chemical structures of Probe 1 and a covalent ERK1/2 inhibitor. (b) Immunoblot for ERK1/2 and Actin showing Probe 1 concentration dependent downregulation of ERK1/2 protein levels. A375 cells were treated with Probe 1 for 18 hours followed by Tz-thalidomide (10 μM) for 18 hours. (c) Immunoblot for ERK1/2 and Actin showing time dependent downregulation of ERK1/2 protein levels. A375 cells were treated with Probe 1 (10 μM) for 18 hours followed by Tz-thalidomide (10 μM) for the indicated time. (d) Immunoblot for ERK1/2 and Actin showing reduced ERK1/2 degradation when the interaction between thalidomide and CRBN is perturbed. A375 cells were treated with Probe 1 for 18 hours followed by methyl-Tz-thalidomide (10 μM) for 18 hours. (e) Immunoblot for ERK1/2 and Actin showing the effects of Probe 1 and Tz-thalidomide alone, the effects of preventing the click reaction using a covalent ERK1/2 inhibitor and the effects of a 4-hour pre-treatment with Carfilzomib (1 μM) on ERK1/2 protein levels. Experiments performed on A375 cells.

FIG. 6: LC-MS profile of the click reaction between Probe 1 and Tz-thalidomide. LC-MS analysis of Probe 1 (right hand peak), Tz-thalidomide (left hand peak) and the reaction mixture after 15 min (middle peaks).

FIG. 7: Immunoblot for ERK2 and Actin showing Probe 1 dose-dependent downregulation of ERK2 protein levels. HCT116 cells were treated with Probe 1 for 18 hours followed by Tz-thalidomide (10 μM) for 18 hours.

FIG. 8: Immunoblot for ERK2 and Actin showing a reduced ERK1/2 degradation with methyl-Tz-thalidomide. HCT116 cells were treated with Probe 1 for 18 hours followed by methyl-Tz-thalidomide (10 μM) for 18 hours.

FIG. 9: (a) Immunoblot for BRD4 and Actin showing no BRD4 degradation when pre-clicked CLIPTAC1 was used. HeLa cells were treated with CLIPTAC1 for 18 h. (b) Immunoblot for ERK1/2 and Actin showing no ERK1/2 degradation when pre-clicked CLIPTAC2 was used. A375 cells were treated with CLIPTAC2 for 18 h.

FIG. 10: Influence of Probe 1 incubation time on ERK1/2 degradation. A375 cells were treated with Probe 1 for 24 h (A), 8 h (B) or 4 h (C) before the addition of Tz-thalidomide (10 μM, 18 h). Following cell lysis, the levels of ERK1/2 were studied by Western Blots.

FIG. 11: Influence of Tz-thalidomide concentration on ERK1/2 degradation. A375 cells were treated with Probe 1 for 4 h followed by Tz-thalidomide (10 μM (A), 3 μM (B), 1 μM (C)) for 18 h. Following cell lysis, the levels of ERK1/2 were studied by Western Blots.

FIG. 12: Influence of linker length on ERK1/2 degradation. A375 cells were treated with Probe 1 for 8 h followed by Tz-thalidomide (10 μM) for 18 h. Following cell lysis, the levels of ERK1/2 were studied by Western Blots.

EQUIVALENTS

The foregoing description details presently preferred embodiments of the present invention. Numerous modifications and variations in practice thereof are expected to occur to those skilled in the art upon consideration of these descriptions. Those modifications and variations are intended to be encompassed within the claims appended hereto.

The invention claimed is:

1. A Clickable Proteolysis Targeting Chimera (CLIPTAC) comprising:
   (a) a first portion comprising a target ligand for an intracellular target protein;
   (b) a second portion comprising a ligand for an E3 ubiquitin ligase; and
   (c) a linker portion covalently coupling the first and second portions;
wherein the linker comprises a covalent bond produced by a bioorthogonal click reaction between a compatible pair of reactive moieties;
wherein:
   the compatible pair of reactive moieties is a diene group and a dienophile group and the bioorthogonal click reaction is an inverse electron demand Diels-Alder (IEDDA) reaction; or
   the compatible pair of reactive moieties is an azide group and a strained alkyne group and the bioorthogonal click reaction is a strain-promoted alkyne azide cycloaddition (SPAAC); or
   the compatible pair of reactive moieties is an azide group and a phosphane group, and the bioorthogonal click reaction is a Staudinger ligation.

2. The CLIPTAC of claim 1 wherein the compatible pair of reactive moieties is a diene group and a dienophile group and the bioorthogonal click reaction is an inverse electron demand Diels-Alder (IEDDA) reaction, and wherein:
   the diene group:
      comprises a heteroaromatic ring system possessing at least two adjacent nitrogens; and
   the dienophile group:
      comprises an alkene; or
      comprises an alkyne; or
      comprises a strained alkene or stained alkyne.

3. The CLIPTAC of claim 1 wherein the compatible pair of reactive moieties is an azide group and a strained alkyne group and the bioorthogonal click reaction is a strain-promoted alkyne azide cycloaddition (SPAAC), wherein the strained alkyne group comprises a cyclooctyne; and the cyclooctyne is selected from: azadibenzocyclooctyne (ADIBO, DIBAC or DBCO), tetramethyldibenzocyclooctyne (TMDIBO), cyclooctyne (OCT), aryl-less cyclooctyne (ALO), monofluorocyclooctyne (MOFO), difluorocyclooctyne (DIFO), dibenzocyclooctyne (DIBO), dimethoxyazacyclooctyne (DIMAC), biarylazacyclooctynone (BARAC), bicyclononyne (BCN), tetramethylthiepinium (TMTI, TMTH), difluorobenzocyclooctyne (DIFBO), oxa-dib enzo-cyclooctyne (ODIBO), carboxymethylmonobenzocyclooc-tyne (COMBO) and benzocyclononyne.

4. The CLIPTAC of claim 1 wherein the compatible pair of reactive moieties is an azide group and a phosphane group, and the bioorthogonal click reaction is a Staudinger ligation.

5. The CLIPTAC of claim 1 wherein the target ligand is an inhibitor of the target protein.

6. The CLIPTAC of claim 1 wherein the target ligand:
  (i) comprises a peptide; or
  (ii) is non-peptidic; or
  (iii) is for an intracellular target protein selected from:
    (a) kinases;
    (b) epigenetic proteins (BRDs);
    (c) an oncoprotein; and
    (d) Tau and amyloid β.

7. The CLIPTAC of claim 1 wherein the E3 ubiquitin ligase is selected from: cereblon, Von Hippel Lindau ligase and XIAP; or the E3 ligand
  (a) comprises a peptide; or
  (b) comprises an antibody against E3 ubiquitin ligase; or
  (c) is non-peptidic.

8. The CLIPTAC of claim 1 wherein the linker portion
  (i) is of a length: (a) sufficient to physically separate the first and second portions to an extent whereby binding of the ligands with their respective targets is not mutually exclusive as a result of steric inhibition; or (b) such that E3 ubiquitin ligase bound to the ligand of the second portion is sufficiently close to target protein bound to the ligand of the first portion to trigger ubiquitination of the target protein; or
  (ii) comprises a series of stable covalent bonds incorporating one or more non-hydrogen atoms selected from the group consisting of C, N, O, S and P; or
  (iii) comprises groups selected from: amino, alkylamino, sulfoxide, sulfonyl, carbonyl and imine; or
  (iv) comprises a saturated or unsaturated alkane.

9. The CLIPTAC of claim 1 which is capable of eliciting ubiquitination and consequent proteasomal degradation of the target protein when delivered intracellularly.

10. A pharmaceutical composition comprising the CLIPTAC of claim 1 and optionally a pharmaceutically-acceptable excipient.

11. A method for delivering a CLIPTAC to an intracellular target protein comprising introducing into a cell:
  (a) a first component comprising a ligand for an intracellular target protein and a first reactive moiety;
  (b) a separate second component comprising a ligand for an E3 ubiquitin ligase and a second reactive moiety;
wherein the first and second reactive moieties constitute a compatible pair of bioorthogonal click reactants, whereby intracellular contact between the first and second components triggers a bioorthogonal click reaction whereby the components self-assemble to form a CLIPTAC as defined in claim 1.

12. A method which optionally comprises activity-based protein profiling (ABPP):
  for selectively inducing the degradation of a target protein within a cell via the endogenous ubiquitin proteasome system (UPS), comprising the step of delivering a CLIPTAC to the intracellular target protein; or
  for selectively inhibiting the activity of a target protein within a cell, comprising the step of delivering a CLIPTAC to the intracellular target protein; or
  for selectively ubiquitinating a target protein within a cell, comprising the step of delivering a CLIPTAC to the intracellular target protein; or
  for selectively targeting a protein within a cell for degradation by the endogenous ubiquitin proteasome system (UPS), comprising the step of delivering a CLIPTAC to the intracellular target protein by a method comprising introducing into a cell:
    (a) a first component comprising a ligand for an intracellular target protein and a first reactive moiety; and
    (b) a separate second component comprising a ligand for an E3 ubiquitin ligase and a second reactive moiety;
  wherein the first and second reactive moieties constitute a compatible pair of bioorthogonal click reactants, whereby intracellular contact between the first and second components triggers a bioorthogonal click reaction whereby the components self-assemble to form a CLIPTAC as defined in claim 1.

13. The method of claim 12 wherein:
the cell is an isolated cell; or
the cell is comprised in an organism; or
the cell is comprised in tissue or in an organ; or
the cell is selected from: human, non-human mammal, rodent, rabbit, pig, sheep, goat, cow, rat, mouse, non-human primate and hamster cells.

14. The method of claim 12, wherein:
the first and second components are introduced into the cell sequentially, wherein the first component is introduced into the cell before the second component; or
the second component is introduced into the cell after a time sufficient for the first component to bind to the intracellular target protein has elapsed.

15. A method of treating a subject comprising:
treating cancer;
treating neurological disorders;
treating proteostatic disease;
selectively inducing the degradation of an intracellular target protein in vivo;
selectively inhibiting the activity of an intracellular target protein in vivo;
selectively ubiquitinating an intracellular target protein in vivo; or
selectively targeting an intracellular protein for degradation by the endogenous ubiquitin proteasome system (UPS) in vivo;
said method comprising administering an effective amount of the CLIPTAC of claim 1, or a pharmaceutical composition comprising the CLIPTAC.

16. The method of claim 15 wherein the method is a method of treating cancer, a neurological disorder, or a proteostatic disease, and comprises: (a) selectively inducing the degradation of an intracellular target protein in the subject; or (b) selectively inhibiting the activity of an intracellular target protein in the subject; or (c) selectively ubiquitinating an intracellular target protein in the subject; or (d) selectively targeting an intracellular protein for degradation by the endogenous ubiquitin proteasome system (UPS) in the subject.

17. The CLIPTAC of claim 2 wherein the diene group:
comprises a heteroaromatic ring system possessing at least two adjacent nitrogens.

18. The CLIPTAC of claim 2 wherein the dienophile group:
  (iv) comprises a straight chain alkene; or
  (v) comprises an internal alkyne, terminal alkyne or cyclic alkyne; or
  (vi) comprises a strained alkene or strained alkyne.

19. The CLIPTAC of claim 18 wherein the dienophile group:
(iv) comprises a straight chain alkene selected from ethylene and propylene; or
(v) comprises an internal alkyne, terminal alkyne or cyclic alkyne; or
(vi) comprises a strained alkene selected from a norbornene, a trans-cyclooctene (TCO), methyl cyclopropane, and a vinyl; or
comprises bicyclo[6.1.0]non-4-yn-9-ylmethanol (BCN).

20. The CLIPTAC of claim 6 wherein the target ligand:
(i) comprises a peptide that is an oligopeptide; or
(ii) is non-peptidic and is a small molecule; or
(iii) is for an intracellular target protein selected from:
(a) kinases ERK1/2 and ERK5;
(b) epigenetic proteins BRD4, HDACs, HATs, KDMs, MBTs and PMTs;
(c) an oncoprotein; and
(d) Tau and amyloid β.

21. The CLIPTAC of claim 1 wherein the compatible pair of reactive moieties is a diene group and a dienophile group and the bioorthogonal click reaction is an inverse electron demand Diels-Alder (IEDDA) reaction, and wherein:
the diene group:
is selected from: pyridazines, substituted or unsubstituted 1,2-diazines, pyrido[3,4-d]pyridazines, pyridazino[4,5-d]pyridazines, triazines, imidazo[4,5-d]pyridazines and 1,2,3-triazolo[4,5-d]pyridazines; or
comprises a tetrazine; and
the dienophile group:
comprises a strained alkene selected from a norbornene, a trans-cyclooctene (TCO), a cyclopropane and a vinyl; or
comprises bicyclo[6.1.0]non-4-yn-9-ylmethanol (BCN).

22. The CLIPTAC of claim 1 wherein the target ligand: comprises an antibody against the target protein.

23. The CLIPTAC of claim 1 wherein the E3 ligand is a non-peptidic small molecule.

24. The CLIPTAC of claim 2 wherein the diene group:
is selected from: pyridazines, substituted or unsubstituted 1,2-diazines, pyrido[3,4-d]pyridazines, pyridazino[4,5-d]pyridazines, triazines, imidazo[4,5-d]pyridazines and 1,2,3-triazolo[4,5-d]pyridazines; or
comprises a tetrazine selected from 3-(p-Benzylamino)-1,2,4,5-tetrazine, another asymmetrical tetrazine, and a functionalized 1,2,4,5-tetrazine.

25. The CLIPTAC of claim 6 wherein the target ligand comprises an antibody against the target protein.

* * * * *